US012186210B2

(12) United States Patent
Galloway et al.

(10) Patent No.: US 12,186,210 B2
(45) Date of Patent: Jan. 7, 2025

(54) WEARABLE DEVICE INCLUDING A SENSOR-ACTUATED SOFT ACTUATOR AND METHOD FOR ACTUATION

(71) Applicant: President and Fellows of Harvard College, Cambridge, MA (US)

(72) Inventors: Kevin Galloway, Somerville, MA (US); Conor Walsh, Cambridge, MA (US); Donal Holland, Athgarvan (IE); Panagiotis Polygerinos, Mesa, AZ (US); Tyler Clites, Natick, MA (US); Paxton Maeder-York, Cambridge, MA (US); Ryan Neff, Lincoln Park, NJ (US); Emily Marie Boggs, Charleston, WV (US); Zivthan Dubrovsky, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1077 days.

(21) Appl. No.: 17/016,066

(22) Filed: Sep. 9, 2020

(65) Prior Publication Data
US 2021/0079935 A1    Mar. 18, 2021

Related U.S. Application Data

(63) Continuation of application No. 16/186,823, filed on Nov. 12, 2018, now Pat. No. 10,788,058, which is a
(Continued)

(51) Int. Cl.
*A61F 2/68*      (2006.01)
*A61B 17/02*   (2006.01)
(Continued)

(52) U.S. Cl.
CPC ............. *A61F 2/68* (2013.01); *A61B 17/02* (2013.01); *A61B 17/0218* (2013.01);
(Continued)

(58) Field of Classification Search
CPC   A61F 5/013; A61F 2/72; A61H 1/024; A61H 1/0288; A61H 3/00;
(Continued)

(56) References Cited

U.S. PATENT DOCUMENTS

| 4,751,868 A | 6/1988 | Paynter |
| 4,784,042 A | 11/1988 | Paynter |

(Continued)

OTHER PUBLICATIONS

T. Noritsugu, et al., "Power Assist Wear Driven with Pneumatic Rubber Artificial Muscles," 15th Int. Conf. on Mechanatronics and Machine Vision in Practice, Auckland, NZ (2008).

*Primary Examiner* — Bruce E Snow
(74) *Attorney, Agent, or Firm* — Modern Times Legal; Robert J. Sayre

(57) ABSTRACT

A multi-segment reinforced actuator includes (a) a soft actuator body that defines a chamber and (b) a plurality of distinct reinforcement structures on or in respective segments of the soft actuator body. First and second reinforcement structures are respectively configured to produce a first and second actuation motions, respectively, in first and second segments of the soft actuator body when fluid flows into or out of the chamber. The actuation motions are selected bending, extending, expansion, contraction, twisting, and combinations thereof; and the first actuation motion differs from the second actuation motion. The actuator can be used, e.g., to facilitate bending of the thumb with corresponding bending, extending, expansion, contraction, and twisting actuation motions.

21 Claims, 51 Drawing Sheets

Related U.S. Application Data continuation of application No. 15/033,270, filed as application No. PCT/US2014/062844 on Oct. 29, 2014, now Pat. No. 10,184,500.

(60) Provisional application No. 61/896,984, filed on Oct. 29, 2013.

(51) Int. Cl.

| | | |
|---|---|---|
| *A61B 34/00* | (2016.01) | |
| *A61F 2/70* | (2006.01) | |
| *A61F 2/74* | (2006.01) | |
| *A61F 5/01* | (2006.01) | |
| *A61H 1/02* | (2006.01) | |
| *A61H 3/00* | (2006.01) | |
| *F15B 15/10* | (2006.01) | |
| *A61B 17/00* | (2006.01) | |
| *A61B 17/11* | (2006.01) | |
| *A61B 90/00* | (2016.01) | |
| *A61F 2/72* | (2006.01) | |
| *B25J 9/16* | (2006.01) | |
| *B25J 13/00* | (2006.01) | |

(52) U.S. Cl.
 CPC ............ *A61B 34/70* (2016.02); *A61F 2/70* (2013.01); *A61F 5/013* (2013.01); *A61H 1/024* (2013.01); *A61H 1/0288* (2013.01); *A61H 3/00* (2013.01); *F15B 15/103* (2013.01); *A61B 2017/00535* (2013.01); *A61B 2017/00539* (2013.01); *A61B 2017/00544* (2013.01); *A61B 2017/0225* (2013.01); *A61B 2017/1103* (2013.01); *A61B 2017/1132* (2013.01); *A61B 2090/065* (2016.02); *A61B 2090/0807* (2016.02); *A61F 2/72* (2013.01); *A61F 2/74* (2021.08); *A61H 2201/1238* (2013.01); *A61H 2201/165* (2013.01); *A61H 2201/5061* (2013.01); *A61H 2201/5071* (2013.01); *A61H 2230/105* (2013.01); *A61H 2230/605* (2013.01); *B25J 9/1612* (2013.01); *B25J 13/00* (2013.01); *F15B 15/10* (2013.01)

(58) Field of Classification Search
 CPC ...... A61H 2201/1238; A61H 2201/165; A61H 2201/5061; A61H 2201/5071; F15B 15/103

See application file for complete search history.

(56) References Cited

U.S. PATENT DOCUMENTS

| | | | |
|---|---|---|---|
| 7,331,273 B2* | 2/2008 | Kerekes | B62D 35/007 |
| | | | 92/92 |
| 10,788,058 B2* | 9/2020 | Galloway | A61F 2/68 |
| 2003/0110938 A1 | 6/2003 | Seto et al. | |
| 2006/0161220 A1 | 7/2006 | Kobayashi et al. | |
| 2007/0179339 A1 | 8/2007 | Gorini et al. | |
| 2010/0249675 A1* | 9/2010 | Fujimoto | G06F 3/014 |
| | | | 601/40 |
| 2011/0118635 A1 | 5/2011 | Yamamoto | |
| 2014/0314976 A1 | 10/2014 | Niiyama et al. | |
| 2016/0252110 A1 | 9/2016 | Galloway et al. | |
| 2019/0145435 A1 | 5/2019 | Galloway et al. | |

* cited by examiner 33 psi 33 psi

WEARABLE DEVICE INCLUDING A SENSOR-ACTUATED SOFT ACTUATOR AND METHOD FOR ACTUATION

RELATED APPLICATIONS

This application is a continuation of U.S. application Ser. No. 16/186,823, filed on 12 Nov. 2018, which is a continuation of U.S. application Ser. No. 15/033,270, which is the National Stage of International Application No. PCT/US14/62844, filed on 29 Oct. 2014, the entire contents of which are incorporated herein by reference.

This application also claims the benefit of U.S. Provisional Application No. 61/896,984, filed 29 Oct. 2013, the entire content of which is incorporated herein by reference.

BACKGROUND

Over 795,000 people have a stroke each year in the United States (according to the Center for Disease Control), of which 76% result in disability, costing the nation over $54 billion in lost work and medical fees. Of those that suffered from a stroke last year, two thirds of them survived but were left with any number of disabilities including upper extremity hemiplegia, which occurs amongst approximately 50% of stroke sufferers. If the patient's hand and arm don't receive therapy immediately after a stroke, they can lose function in terms of muscle control and strength.

Research has shown that repetitive motor intensive and function activities can help stroke patients reach partial or full recovery by inducing neural plasticity. Hand therapists work with these patients to perform tasks, such as grasping an object. Patients are expected to continue therapy exercises at home; however, monitoring patient compliance out of the office is difficult, which in turn makes difficult quantifying and evaluating the effectiveness of these therapies.

Actuators can assist patients recovering from strokes and other ailments. A variety of other applications also exist in which the use of actuators can provide assistive benefits.

SUMMARY

A multi-segment reinforced actuator and methods for making and using the actuators are described herein. Various embodiments of the apparatus and methods may include some or all of the elements, features and steps described below.

A multi-segment reinforced actuator includes (a) a soft actuator body that defines a chamber and (b) a plurality of distinct reinforcement structures on or in respective segments of the soft actuator body. First and second reinforcement structures are respectively configured to produce first and second actuation motions, respectively, in first and second segments of the soft actuator body when pressurized fluid flows into or out of the chamber. The actuation motions are selected from bending, extending (longitudinally), expansion (radially), contraction, twisting, and combinations thereof (by pumping fluid into or out of the actuator); and the first actuation motion differs from the second actuation motion. Together, the reinforcement structures generate a plurality of motions selected from bending, extending, expansion, contraction, twisting, and combinations thereof, where the actuated motion in the first segment is different from and non-canceling of the actuated motion in the second segment. The actuator can be used, e.g., to facilitate bending of the thumb with corresponding bending, twisting, and extending actuation motions.

A particular embodiment of a reinforced actuator includes a lower-durometer actuator body and a pneumatic or hydraulic pump coupled with the lower-durometer actuator body and configured to pump fluid into or out of the lower-durometer actuator body. The reinforced actuator also includes a higher-durometer (i.e., a durometer higher than that of the lower-durometer actuator body) reinforcement layer encircling the lower-durometer actuator body, wherein the higher-durometer reinforcement layer includes a strain-limiting band extending longitudinally along at least one side of at least segment of the lower-durometer actuator body and a series of radial bands mutually separated by gaps extending at least partially around the lower-durometer body, wherein segments with different configurations of at least one of the radial band and the strain-limiting band cause the actuator to produce an actuation selected from bending, extending, expansion, contraction, twisting, and combinations thereof by altering the gaps when the lower-durometer body expands or contracts with a change in the fluid pressure in the lower-durometer actuator body.

Embodiments of the actuator can be programmed during the manufacturing phase to achieve a wide range of motions, such as bending, extending, expansion, contraction, twisting, and combinations thereof. The design of the actuator allows complex motions to be built into the body of the actuator, which can reduce control-input complexity and mechanical complexity. Accordingly, the actuator can be designed to safely interact with the user, such as by assisting joint movements and in surgical applications where soft materials, large force displacement, and the ability to squeeze through small openings are desired.

Figure 1:
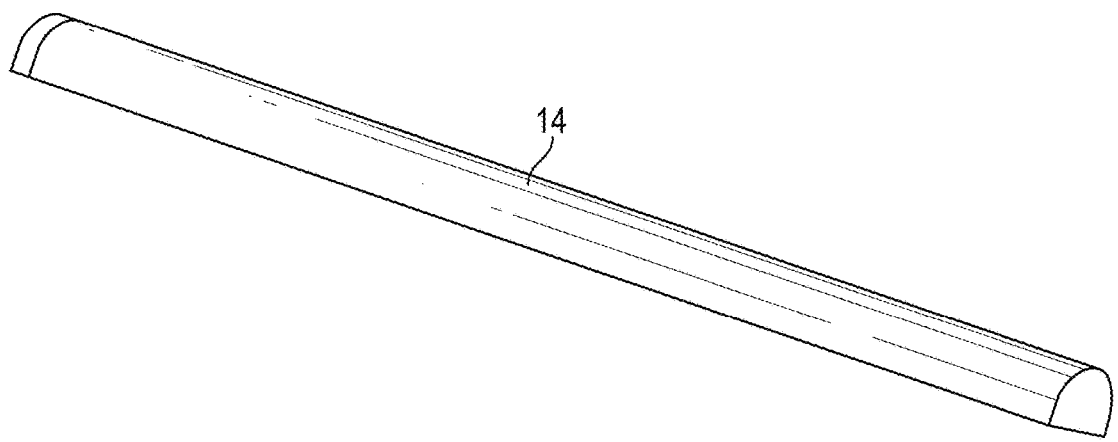
FIG. 1 is an illustration of a half-round soft actuator body 14 with no fiber reinforcements.

In the accompanying drawings, like reference characters refer to the same or similar parts throughout the different views; and apostrophes are used to differentiate multiple instances of the same or similar items sharing the same reference numeral. The drawings are not necessarily to scale, emphasis instead being placed upon illustrating particular principles, discussed below.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially, though not perfectly pure, as practical and imperfect realities may apply; e.g., the potential presence of at least trace impurities (e.g., at less than 1 or 2%) can be understood as being within the scope of the description; likewise, if a particular shape is referenced, the shape is intended to include imperfect variations from ideal shapes, e.g., due to manufacturing tolerances. Percentages or concentrations expressed herein can represent either by weight or by volume.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly.

Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

A soft actuator body 14, as shown in FIG. 1, without any reinforcement can essentially be a balloon that expands in all directions, both radially and in length. For example, the soft actuator body 14 can be a long, narrow half-round, elastomeric chamber that can be inflated through a small opening. In other embodiments, the soft-actuator body can have any of a variety of other cross-sectional shapes, such as rectangular (e.g., with a width of 20 mm and a height of 7 mm along the two shorter axes). Soft actuator bodies 14 of this disclosure can be formed of, e.g., hyper-elastic silicone, rubber, elastic polyurethane, polyethylene, or other material that has a durometer or mechanical stiffness lower than that of the reinforcement 18; the soft actuator body 14 can be designed to expand its dimensions, e.g., to 200% of its original dimensions before failure. In particular embodiments where the actuator is used for medical applications, both the soft actuator body 14 and reinforcements 18 incorporated into or around the soft actuator body can be formed of a biocompatible material.

Figure 2:
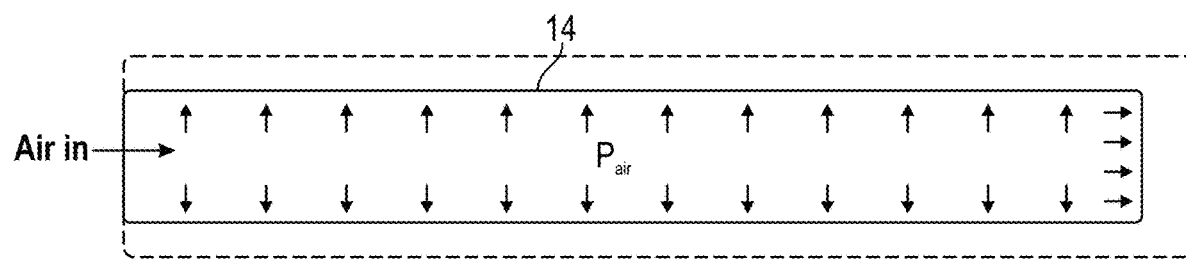
FIG. 2 is a schematic illustration of the soft actuator body 14 of FIG. 1 under fluid pressurization, showing how it expands in all directions.

A schematic illustration of an embodiment of this actuator 12 under fluid pressurization is shown in FIGS. 1 and 2. The expansion of the actuator 12 can be converted to bending, extending, shortening, twisting, and combinations of these actions by reinforcing the actuator 12 in different configurations, such as by adding strain-limiting layers 20 or radial wrapping, which will be discussed below.

Figure 3:
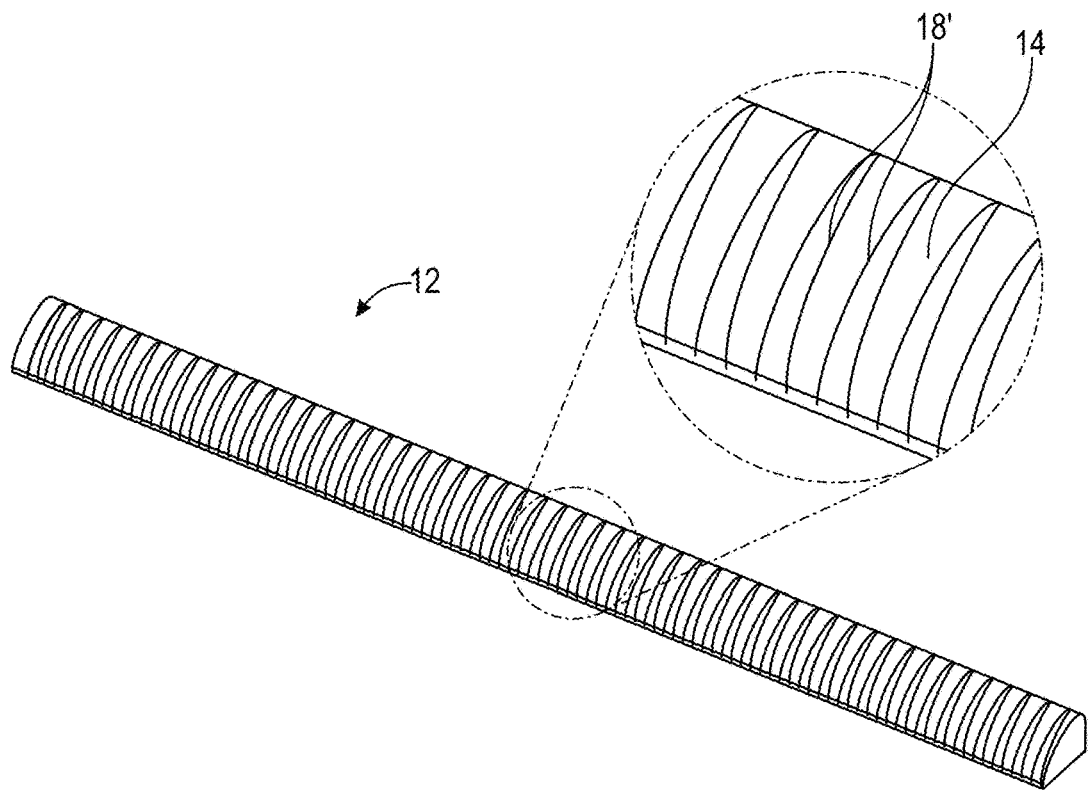
FIG. 3 is an illustration of a soft actuator 12 with symmetric fiber 18' reinforcements (i.e., clockwise and counter clockwise helical fiber reinforcements) in a soft actuator body 14, where the fibers 18' restrict radial expansion and promote linear growth of the actuator 12 upon fluid pressurization.
Figure 4:
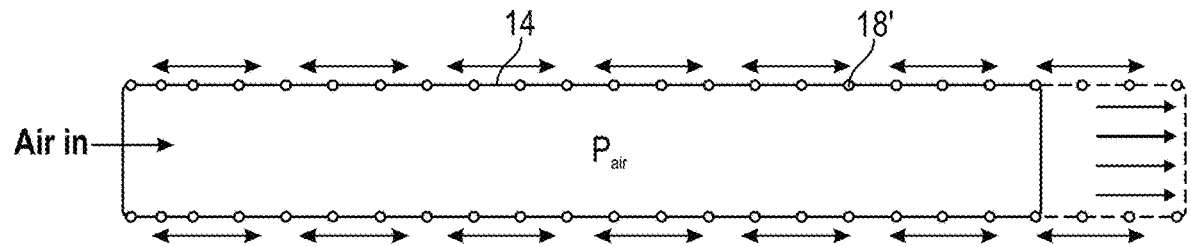
FIG. 4 is a schematic illustration of the linear actuator 12 of FIG. 3 under fluid pressurization.

In an extending actuator, symmetrically wound fiber reinforcements 18' (e.g., with a first fiber wound clockwise into a coil shape and a second fiber wound counter-clockwise into a coil shape) restrict radial expansion and therefore create soft linear actuators that change in length upon pressurization, as shown in FIGS. 3 and 4. A fiber-reinforced actuator 12 with a low-pitch winding grows in length with pressurized fluid. Radial fiber reinforcements 18' with a larger pitch [e.g., oriented at an angle, a, greater than 54° with respect to a plane that is orthogonal to the length (or longest dimension) of the actuator 12] can create a linear actuator 12 that shrinks in length. The fiber is flexible yet substantially non-expanding [e.g., with substantially lower elasticity than the soft actuator body 14 (e.g., with no more than ¹⁄₁₀th of the elasticity of the soft actuator body 14)].

Figure 5:
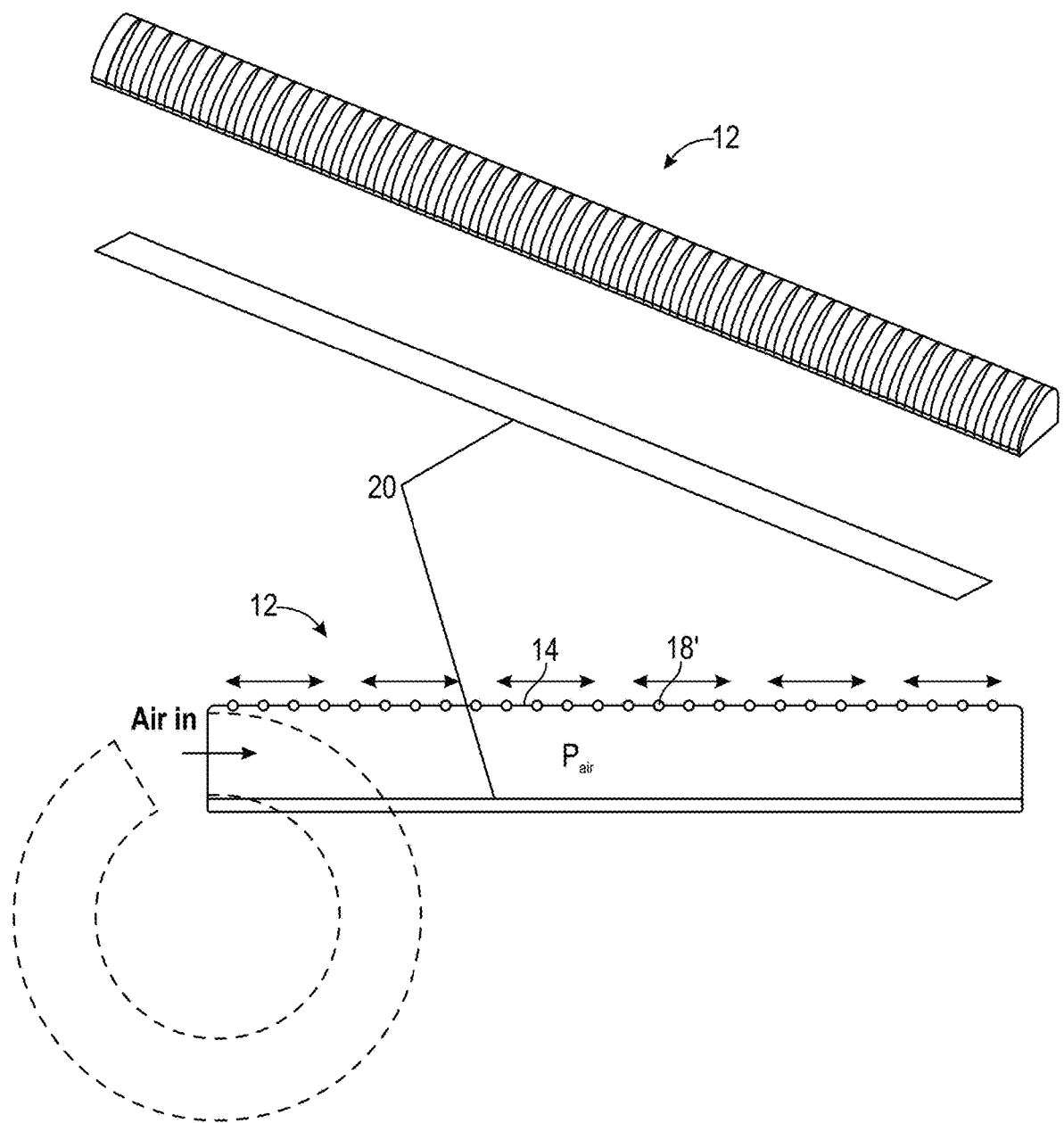
FIG. 5 is a schematic illustration of a bending actuator 12 depicting the placement of a strain-limiting layer 20 along the flat face of the half round.
Figure 6:
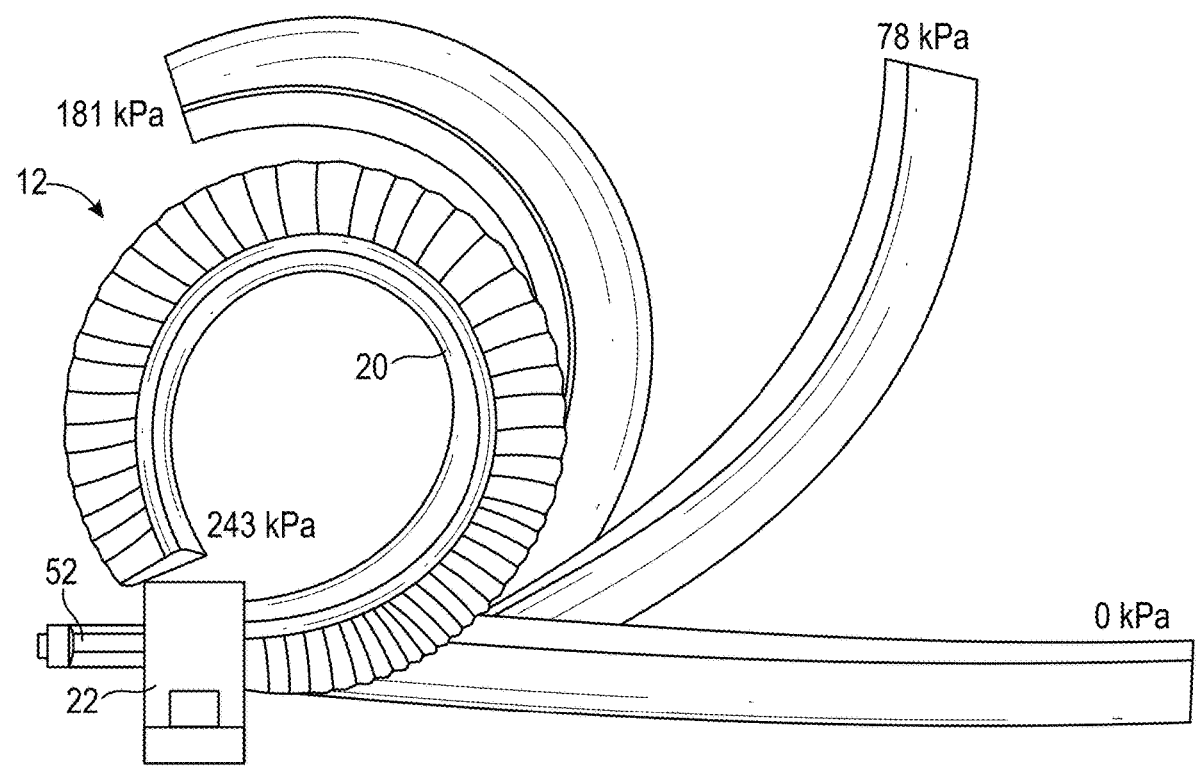
FIG. 6 depicts the bending range of motion of the actuator 12 at different fluid pressurization levels.

A bending actuator 12 can incorporate a strain-limiting layer 20 along one side of the actuator (in this case the flat face 16 of the half round), as shown in FIGS. 5 and 6. The strain-limiting layer 20 can be a higher durometer rubber (i.e., with a durometer higher than that of the soft actuator body 14) or an inextensible but flexible material, such as a woven or non-woven fabric. Upon pressurization, bending motions are generated from the competition between the top portion of the actuator that expands while the bottom portion resists expansion. Also shown in FIG. 6 is a fixture 22 to which the actuator 12 is attached and a connector 52 to which a conduit for pumping fluid into and out of the actuator 12 is attached.

Figure 7:
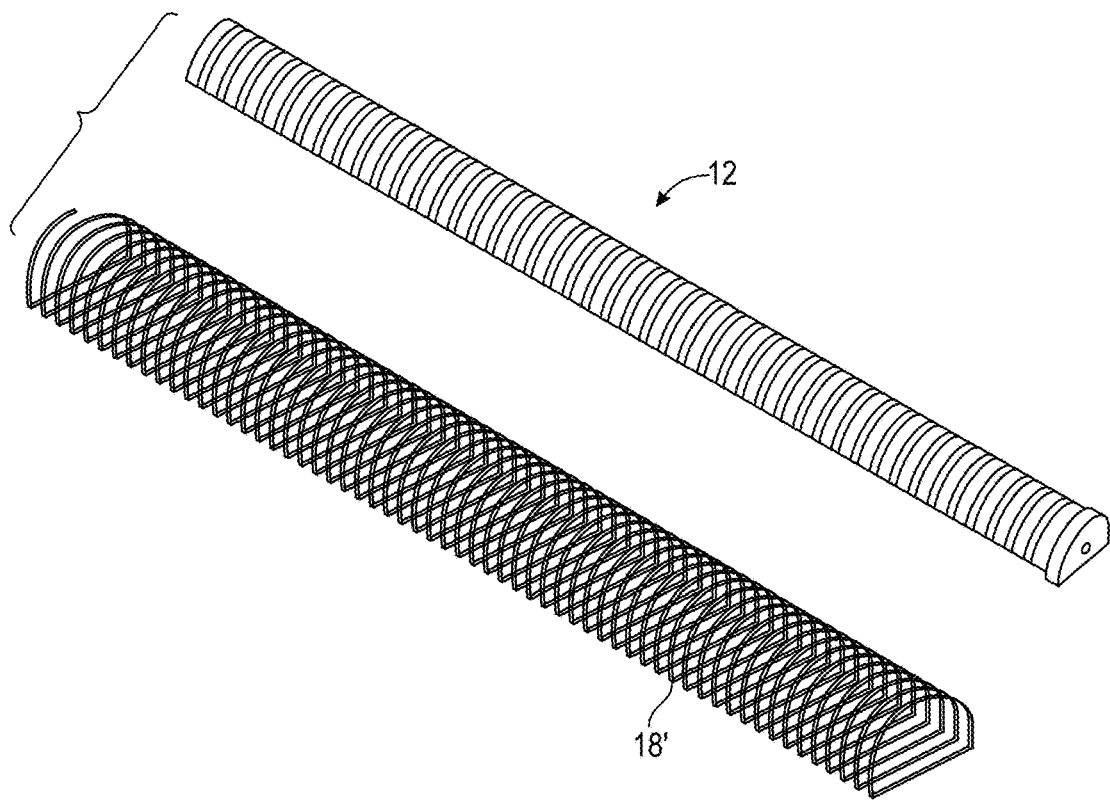
FIG. 7 is a schematic illustration of the fiber reinforcement 18' for a twisting actuator alongside the soft actuator 12.
Figure 8:
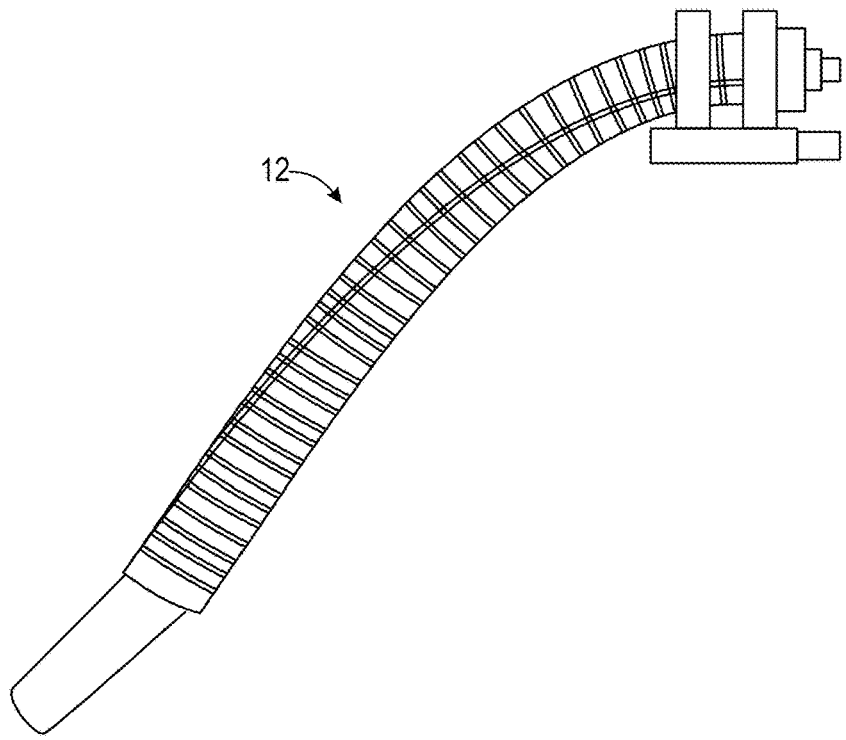
FIG. 8 is an image of an actuated twisting actuator 12.
Figure 9:
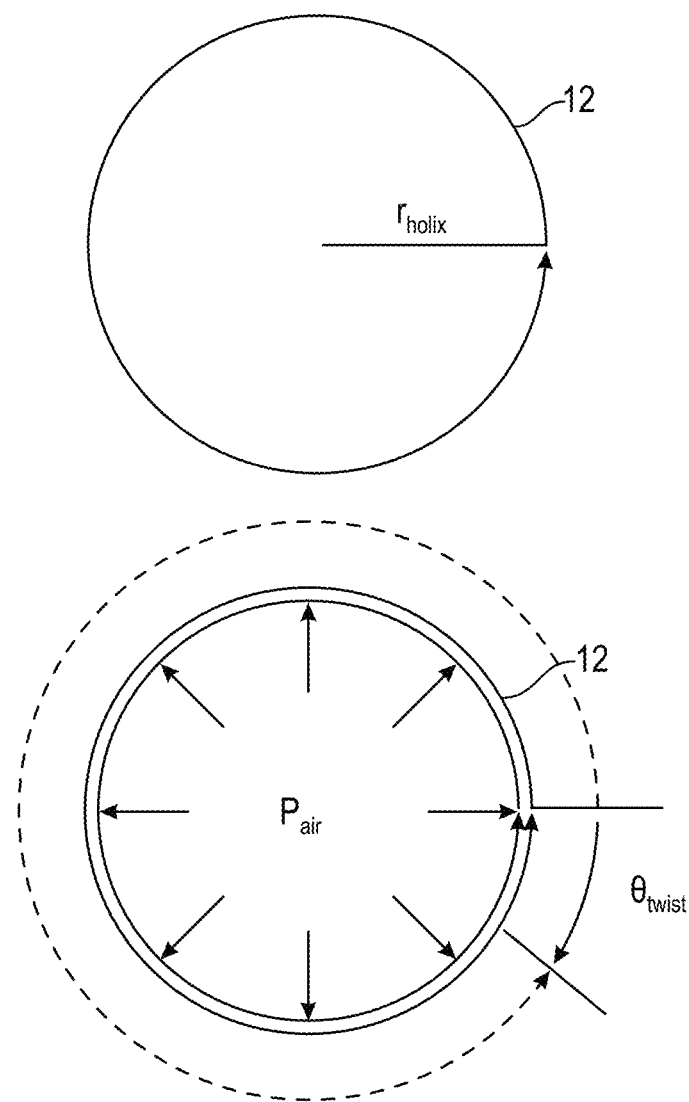
FIG. 9 depicts the bending range of motion of the twisting actuator 12 at different fluid pressurization levels.

In a twisting and extending actuator, as shown in FIGS. 7 and 8, radial fiber reinforcements 18' that are not symmetric (e.g., with only clockwise or counter-clockwise thread winding) produce a twisting motion, as shown in FIGS. 8 and 9, around the long axis of the actuator 12. For example, wrapping fiber 18' clockwise around the actuator 12 causes the actuator 12 to twist counterclockwise and extend when inflated. A single wrapping allows some radial expansion; however, because the fiber 18' (in thread form) is a fixed length, the number of coil windings of thread decrease to accommodate the larger radius. Therefore, in order to decrease the number of complete coil windings, the tip of the actuator 12 must twist in the opposite direction of wrapping. As the number of initial coil windings increases, the amount of twisting increases, while the force of twisting decreases.

Figure 10:
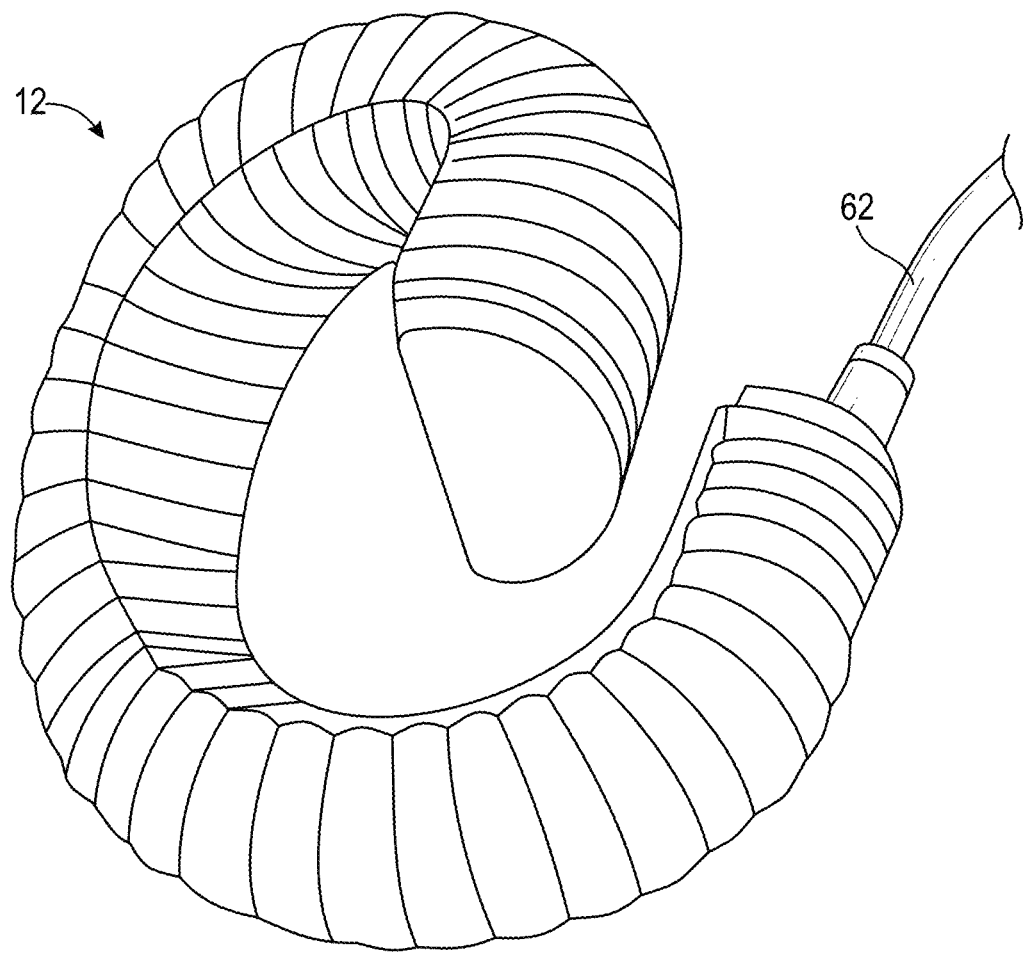
FIG. 10 is an image of a physical prototype of a pressurized bend-and-twist actuator 12.

Bend and twist actuators 12 can be combined into one actuator 12 where the final actuator 12 forms a helical shape upon pressurization, as shown in FIG. 10.

Figure 11:
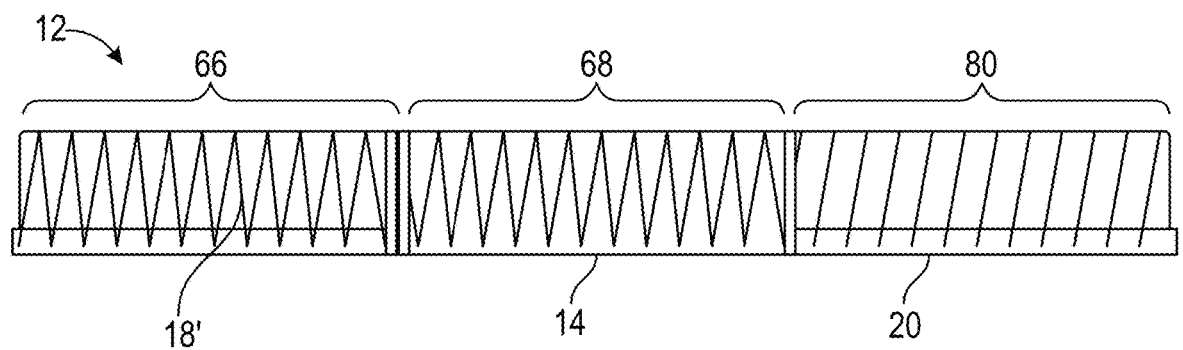
FIG. 11 is a schematic illustration of a multi-segment actuator 12 that will perform three motions simultaneously—bend 66, extend 68, and bend-twist 80—upon fluid pressurization.
Figure 12:
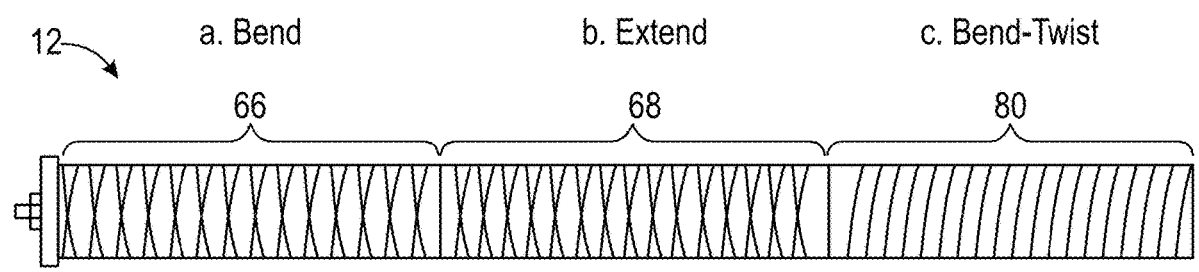
FIG. 12 is a proof-of-concept multi-segment actuator 12 that is not pressurized (unactuated); the actuator includes bend 66, extend 68, and bend-and-twist 80 sections.
Figure 13:
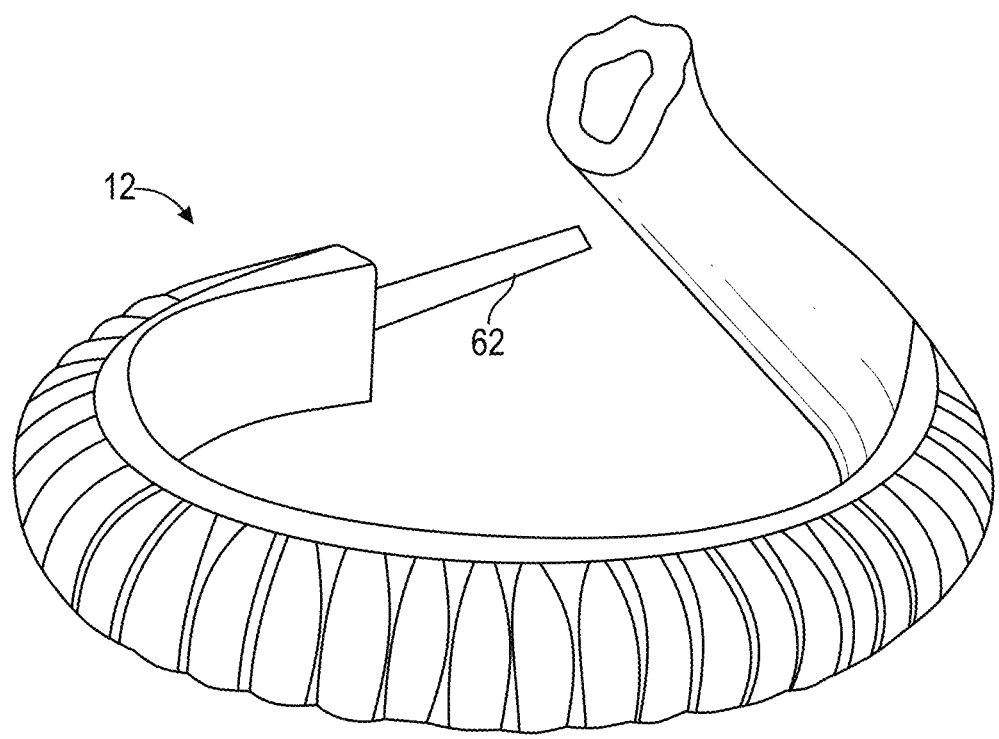
FIG. 13 is the multi-segment actuator 12 of FIG. 12 when pressurized (actuated).

These actuators 12 can be co-molded and can integrate multiple types of strain-limiting geometries, as described above, in series to enable the combination of bending, twisting, bending-twisting, extending (or contracting) and/or extending-twisting motions into a single fiber-reinforced soft actuator 12. For example, an actuator 12 can be made that bends along one segment, extends along another segment, and bend-twists along a third segment, as shown in the schematic illustration of FIG. 11 and in the image of the proof-of-concept design shown unpressurized in FIG. 12 and pressurized in FIG. 13.

Figure 14:
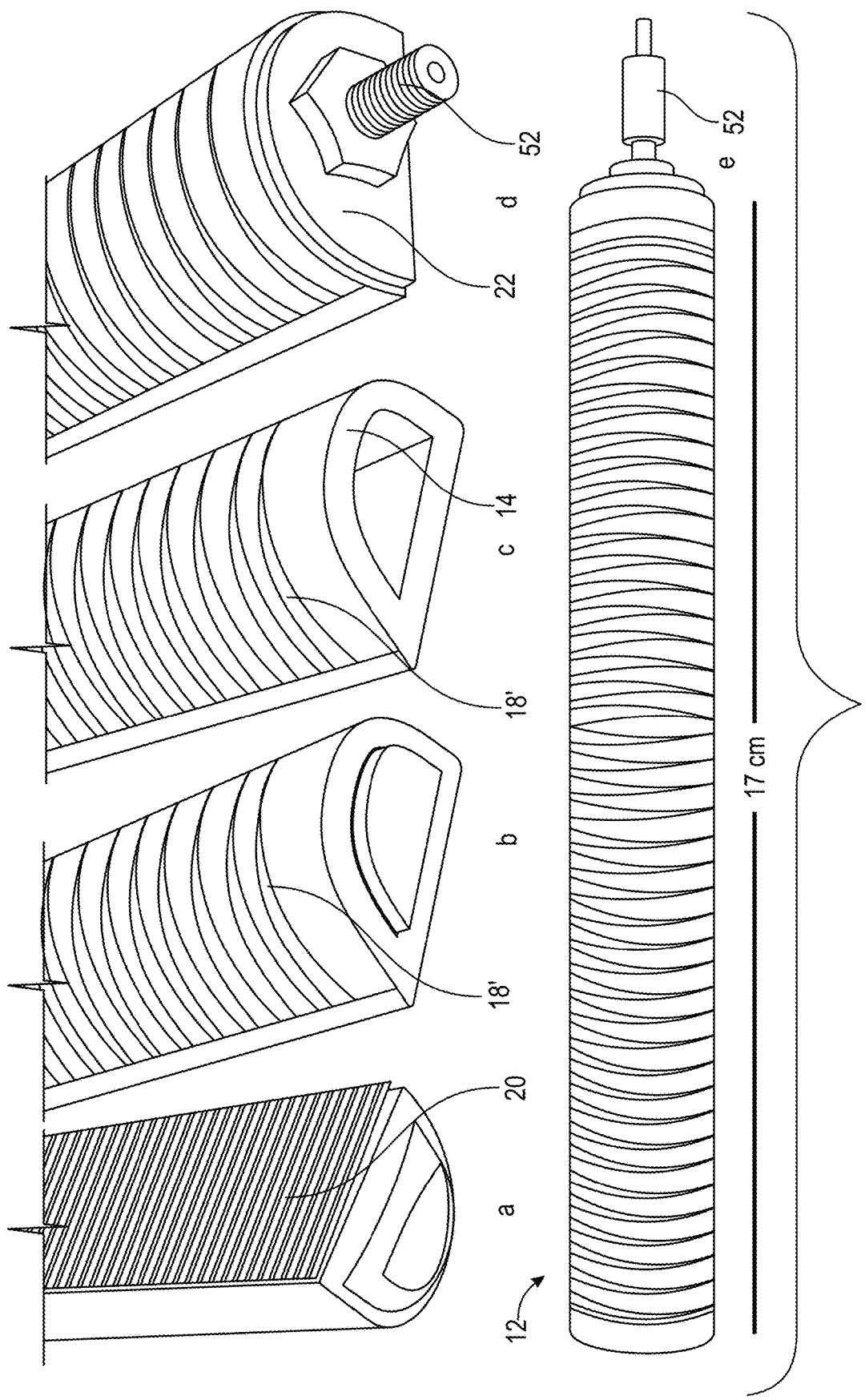
FIG. 14 provides images of several stages of a soft actuator fabrication process, showing the strain-limiting layer 20, fiber reinforcements 18', the end-cap fixture 22, and a connector 52 for the fluid line.

Either of the following two methods can be used to create multi-segment reinforced soft actuators 12. A first method uses a high-tensile-strength thread, such as Kevlar, and a strain-limiting layer 20 made of an inextensible (or at least less extensible than the remaining structure in the actuator 12) but flexible sheet material, such as woven fiberglass. The strain-limiting layer 20 is applied to sections where bending motions are desired, and the thread is wound along the length of the actuator 12 as radial fiber reinforcement 18'. Images at the different stages of the prototyping process for a bending actuator 12 are shown in FIG. 14. Consistent with the above discussion, the different combinations of thread winding patterns (e.g., clockwise and counter-clockwise) and the inclusion (or exclusion) of a strain-limiting layer 20 can generate a wide range of complex soft actuation motions.

In the fabrication process, after the first molding step to form the soft actuator body 14, a strain-limiting layer 20 (here, woven fiberglass) is glued to the flat face of the soft actuator body 14 to produce the composite structure shown in image (a) of FIG. 14. Fiber reinforcing thread 18' (here, Kevlar) is then hand wound along the entire length of the composite body to produce the structure shown in image (b) of FIG. 14. In a second molding step, the entire actuator 12 is encapsulated in a thin layer of silicone to anchor all fiber reinforcements to produce the structure shown in image (c) of FIG. 14. Both ends of the actuator are then capped with a fixture 22 at one end supporting a vented screw 50, as shown in image (d) of FIG. 14. Finally, a top view of the completed bending actuator 12 with a barbed tube fitting 52 threaded onto a vented screw as a connector 52 is provided in image (e) of FIG. 14.

Figure 15:
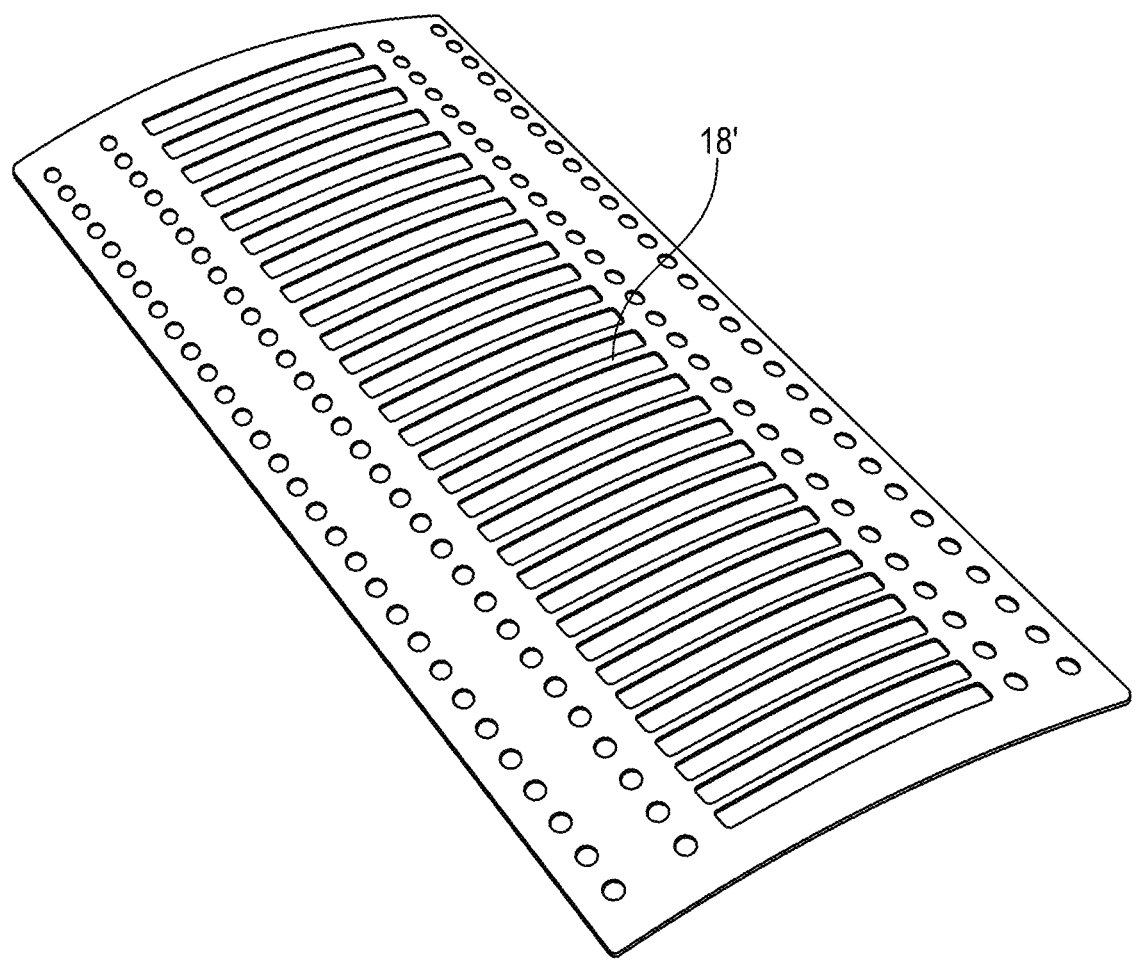
FIG. 15 is an image of a layer 18" formed of flash-spun high-density fibers (marketed commercially as TYVEK non-woven material by DuPont) with horizontal perforations.
Figure 16:
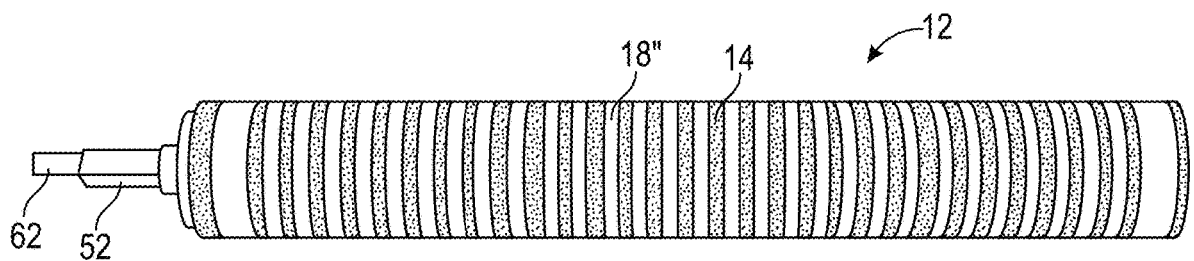
FIG. 16 is an image of a TYVEK layer 18", as shown in FIG. 15, applied to an actuator body 14.
Figure 17:
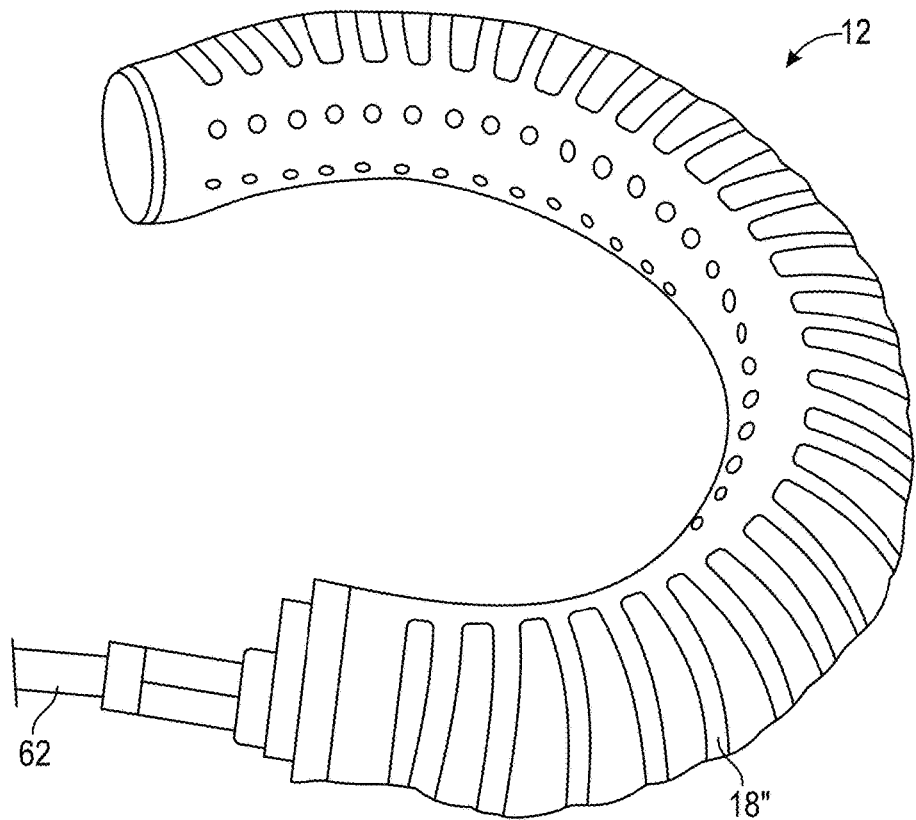
FIG. 17 shows the resulting bending of the soft actuator 12 when pressurized and demonstrating that the perforated TYVEK layer 18" can perform the following two functions: acting as a strain-limiting layer along the length of the actuator 12 to promote bending and acting as a radial strain-limiting layer to constrain radial swelling.
Figure 18:
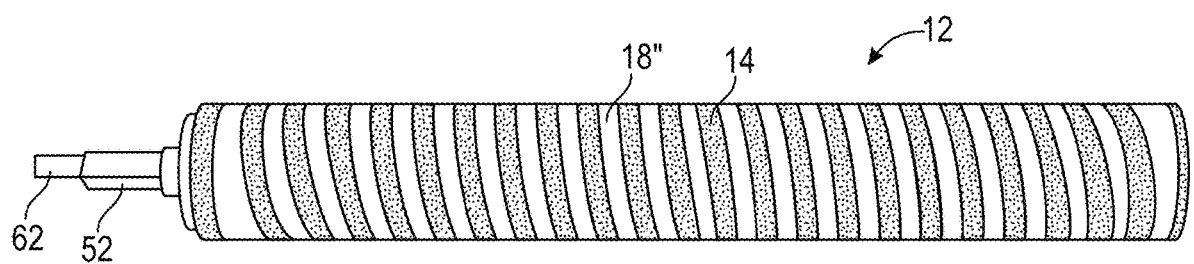
FIG. 18 is an image of a TYVEK layer 18" with angled perforations that is applied to an actuator body 14.
Figure 19:
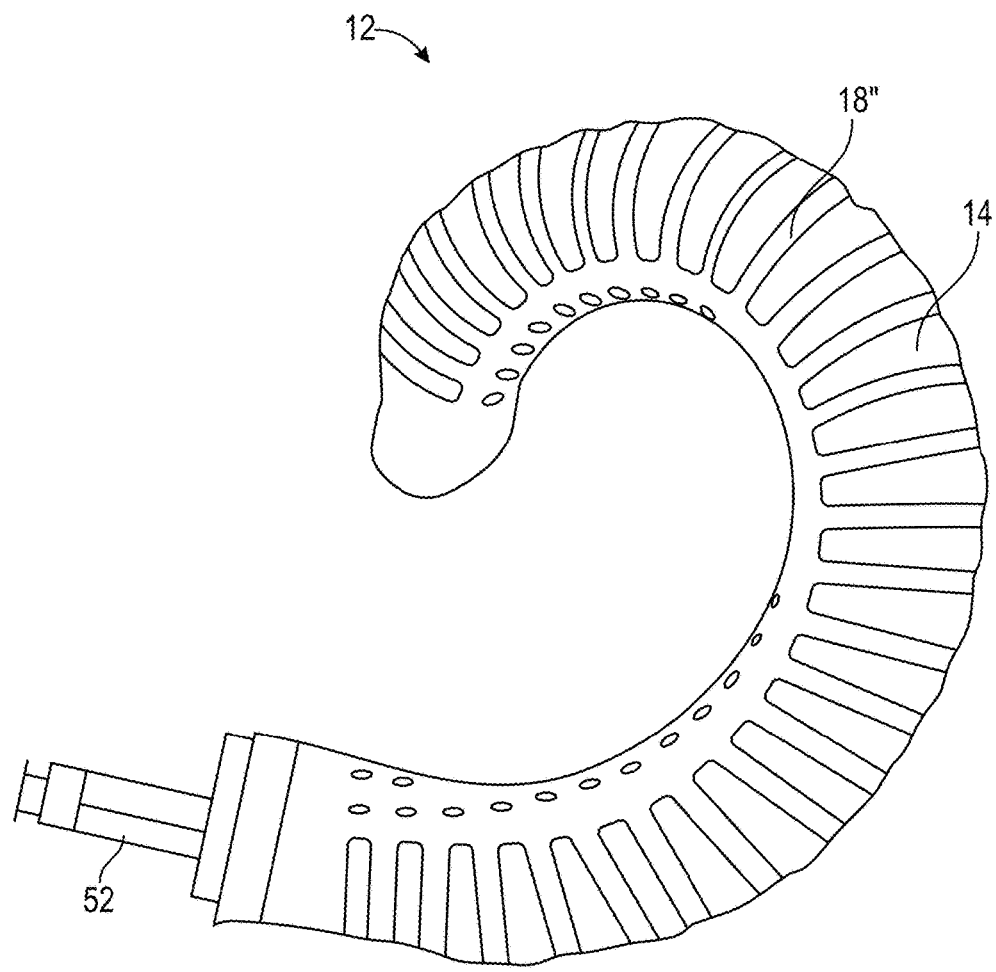
FIG. 19 is an image of the actuator 12 of FIG. 18 pressurized and demonstrating that the angled perforations can be used to create a bend-twist soft actuator.

A second method for creating a multi-segment reinforced soft actuator perforates a pattern onto a single sheet of material (i.e., woven or non-woven material) that is then applied around the actuator. For example, a sheet of non-woven fine fibers of high-density polyethylene 18" (available as TYVEK sheets from E. I. du Pont de Nemours and Company) with horizontal perforations, as shown in FIG. 15, can be applied to create a bending actuator 12, as shown in FIGS. 16 and 17. The horizontal perforations separate the intervening bands, which serve as an embodiment of the radial bands around the soft actuator body when the perforated sheet is wrapped around the soft actuator body; and the perforated pattern of the TYVEK sheet offers the combined effect of wound threads and the strain-limiting layer with a single material. This method also offers more control over fiber coverage. For example, the resulting width and angle of the perforated reinforcing layer can be adjusted almost arbitrarily; though, if thin widths are needed, thread/fiber may be a better solution. FIGS. 18 and 19 demonstrate that angling the perforations creates a bend-twist actuator 12. This approach also offers more design freedom in that the perforations do not need to be evenly spaced. There can be a gradient increase or decrease in the spacing or in the angle of the perforations. Furthermore, if no actuation is desired in certain sections, then those areas need not have any perforations.

Figure 20A:
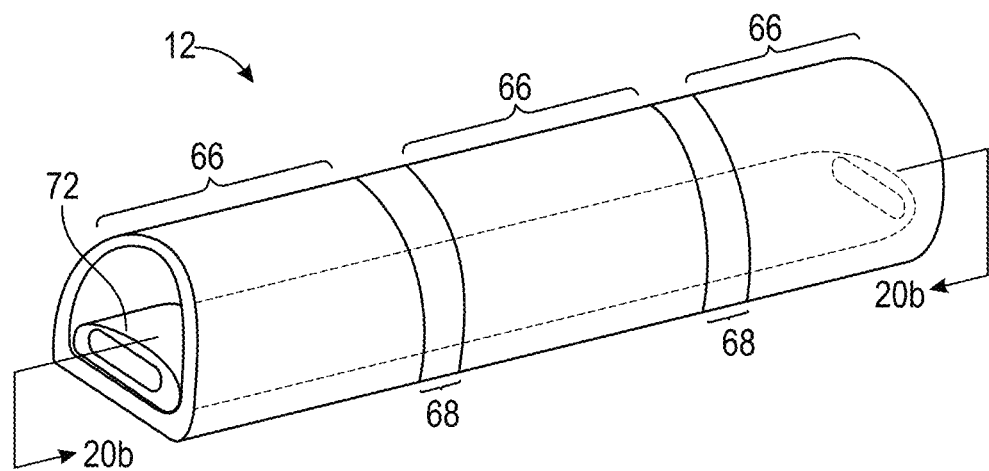
FIGS. 20a and 20b respectively present isometric and cross-sectional views of a multi-segment, multi-chamber soft actuator 12 with stiffening capabilities provided by an internal bladder 72 that defines a second chamber.
Figure 20B:
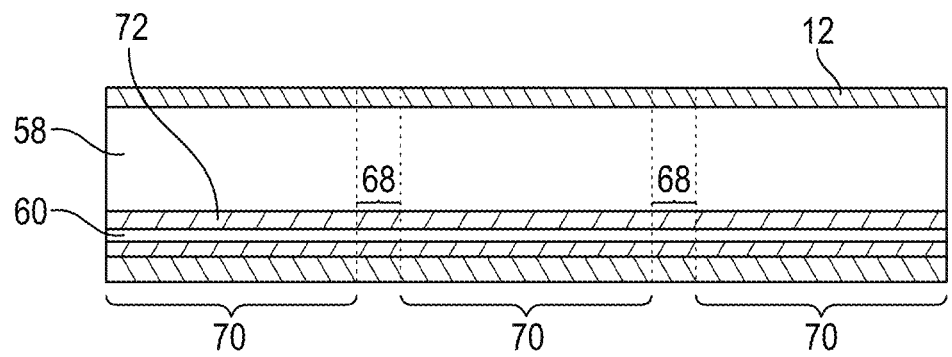
Figure 21:
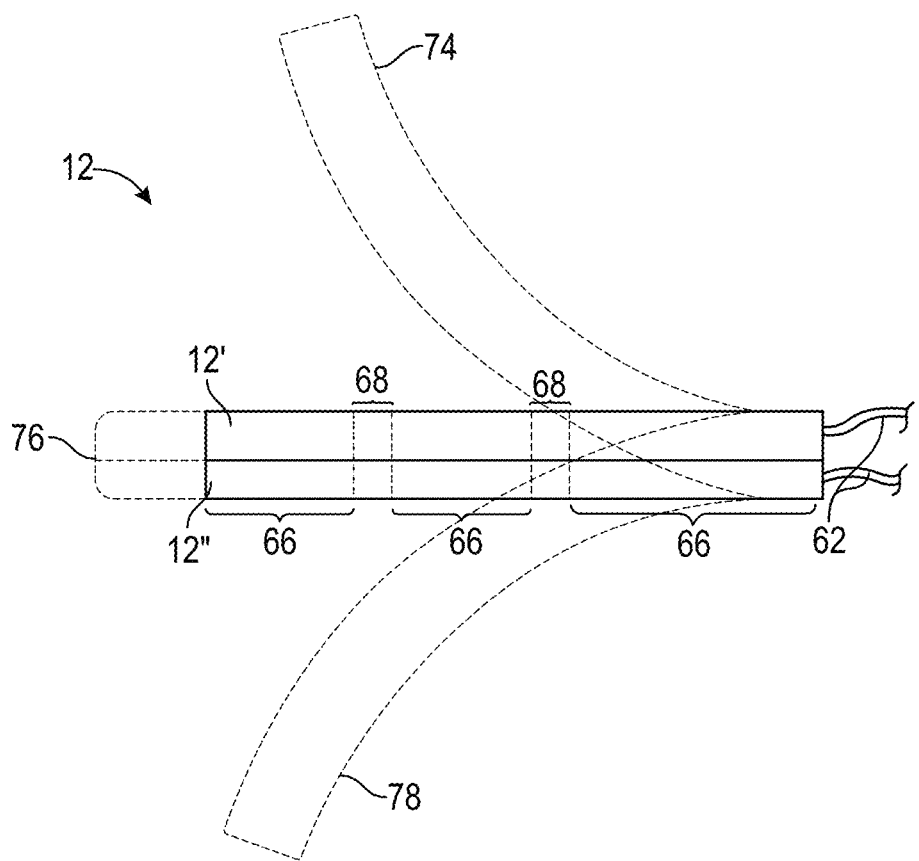
FIG. 21 presents a side view of another embodiment of a multi-segment, multi-chamber actuator device comprising a pair of bonded soft actuators 12' and 12".
Figure 22A:
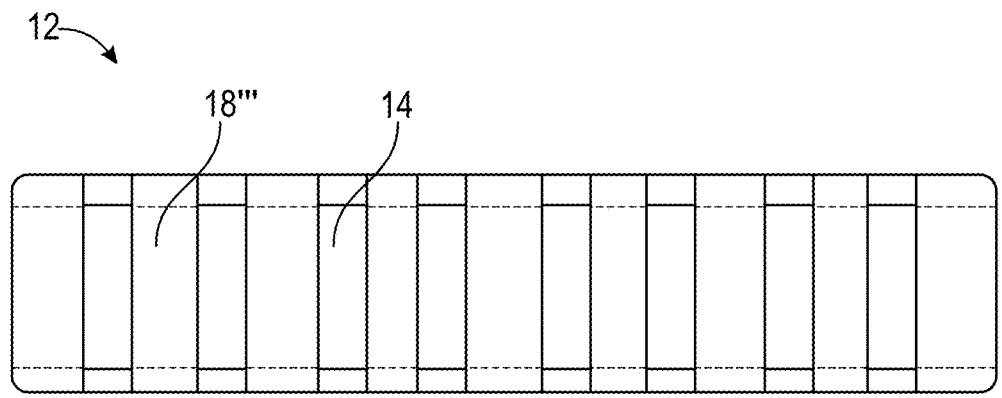
FIGS. 22a-d present orthographic and isometric views of an actuator 12 comprising a soft bending actuator body 14 contained in a higher-durometer rubber reinforcement 18'''.
Figure 22B:
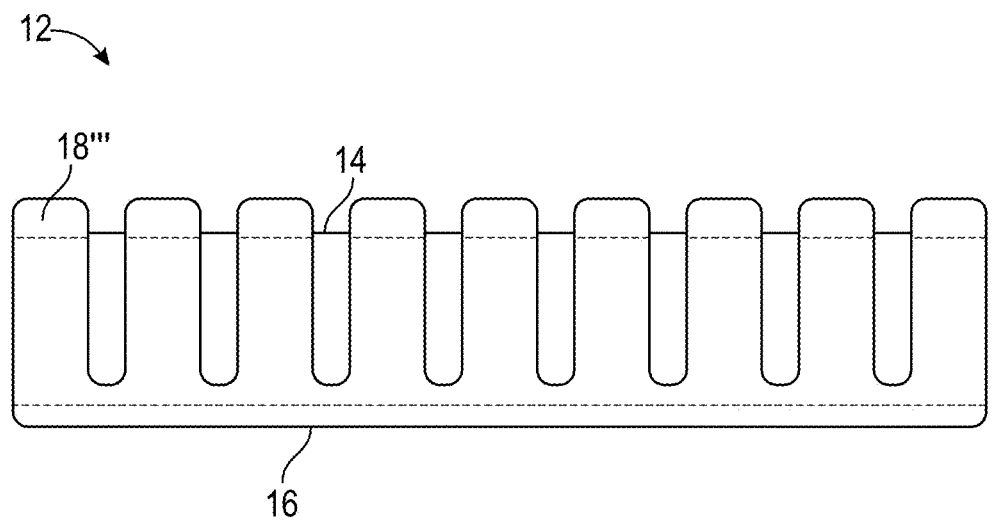
Figure 22C:
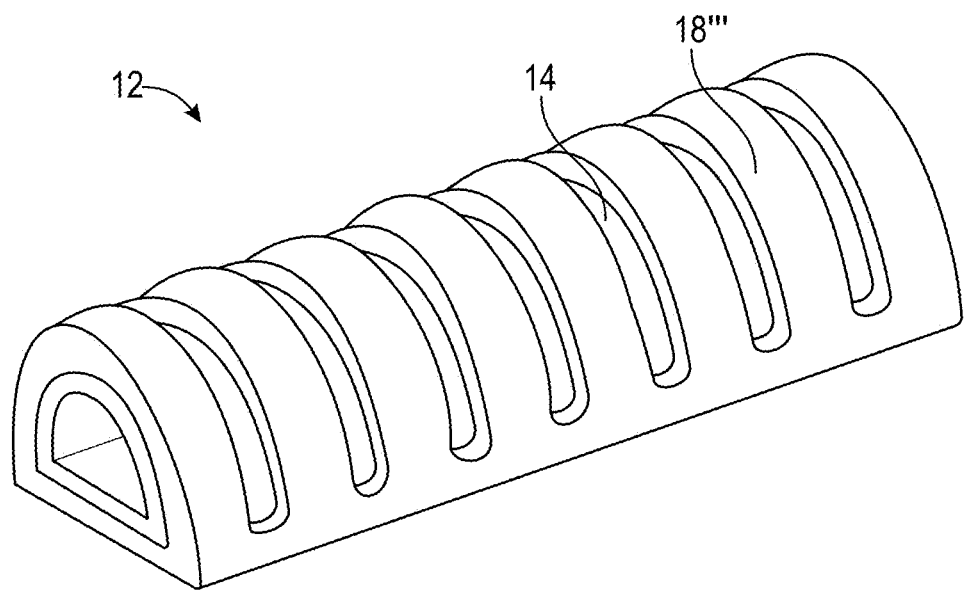
Figure 22D:
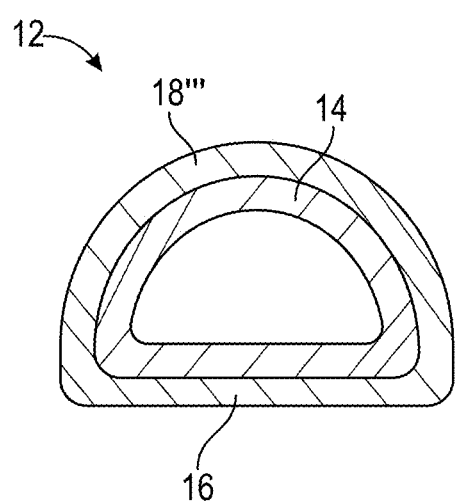

Multi-segment actuators can also be extended to include multiple chambers that can be used to increase the range of motion of the actuator 12 and to add different functionalities. FIGS. 20a and 20b present a multi-segment, multi-chamber actuator 12 where each chamber 58 and 60 has a different reinforcement strategy. In this particular example, when first chamber 58 is pressurized, the actuator 12 will bend (across bend sections 66) and extend (across extension sections 68). However, if only the second chamber 60, which is defined by a bladder 72, is pressurized, its stiffening sections 70 will promote stiffening (instead of bending) and extension (across extending sections 68). FIG. 21 presents another embodiment of a multi-chamber, multi-segment actuator device where two opposing "bending and extending" actuators 12' and 12" are combined. In this configuration, activation of one of the actuators 12' and 12" will cause the structure to bend in one direction and vice versa. Additionally, activation of both actuators 12' and 12" will cause the entire structure to extend.

Figure 23:
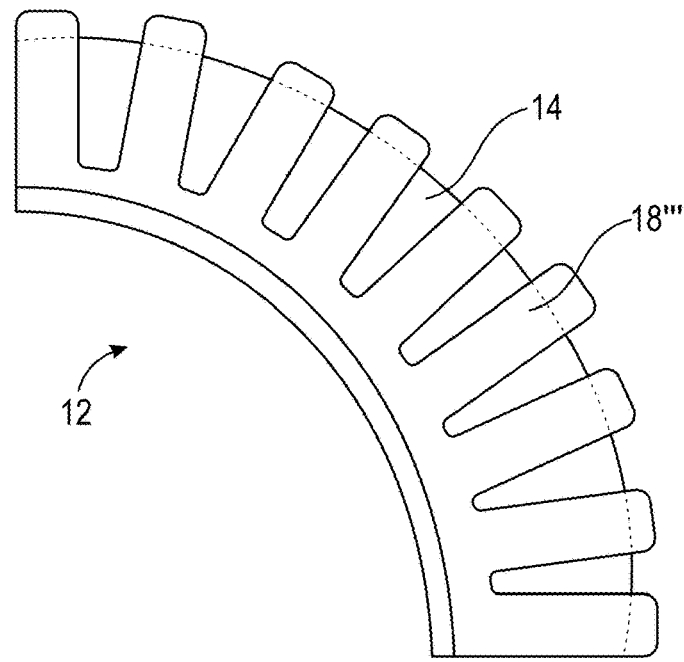
FIG. 23 shows the resulting bending soft actuator 12 of FIGS. 22a-d when pressurized.
Figure 24:
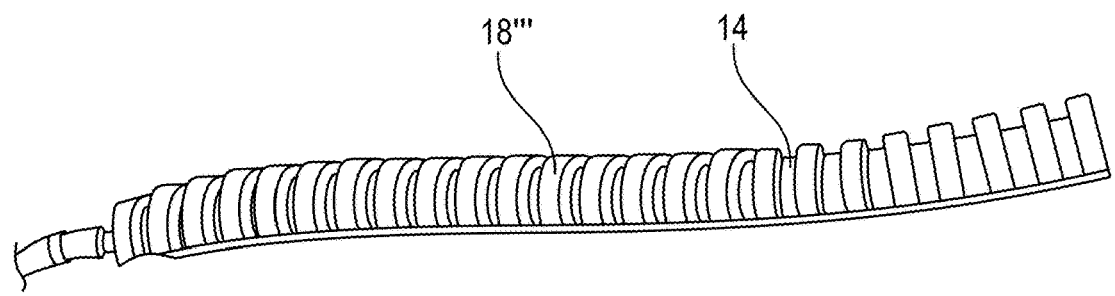
FIGS. 24 and 25 are images of a prototype rubber-reinforced soft bending actuator without and with fluid pressurization, respectively.
Figure 25:
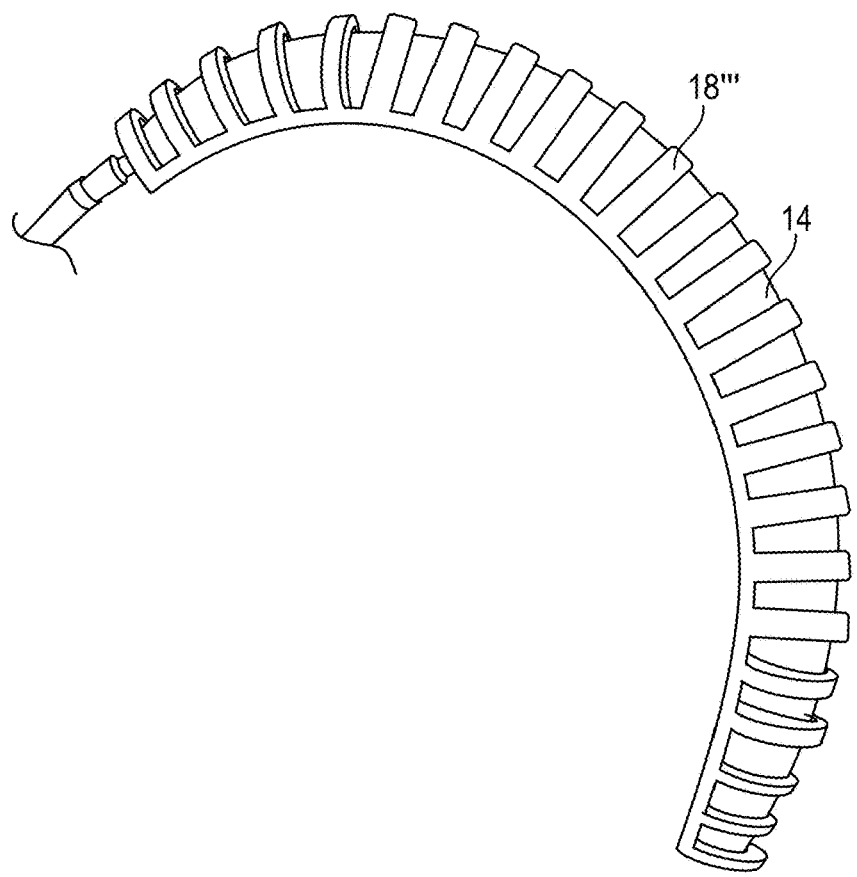

Another method for creating a multi-segment reinforced soft actuator 12 uses a higher-durometer material (e.g., with a durometer two to three times that of the soft actuator body 14), such as molded rubber, around the soft actuator body 14. In this method, the actuator does not need fiber-reinforcements 18'. Instead, the rubber reinforcements 18''' can be designed to radially (via a plurality of interconnected radial bands) and axially constrain any part of the soft actuator body 14. Note that increasing the wall thickness instead of using a higher-durometer material can produce a similar effect; however, this approach could require substantially thick geometries to produce the same effect that a smaller geometry with a stiffer material could achieve. FIGS. 22a-d give perspective views of a soft bending actuator 12 with rubber reinforcement 18''' where small cutouts expose portions of the soft actuator body 14 that are allowed to expand. Along the flat face 16 of this actuator is a solid sheet of the reinforcing material that acts as the strain-limiting layer 20. FIG. 23 shows a side view of the rubber-reinforced actuator 12 when it is pressurized. FIGS. 24 and 25 are drawings of a rubber-reinforced soft bending actuator 12 where the reinforcement layer 18''' is formed of 45 A shore hardness silicone rubber, and the silicone actuator body 14 is formed of 20 A shore hardness silicone rubber.

Figure 26:
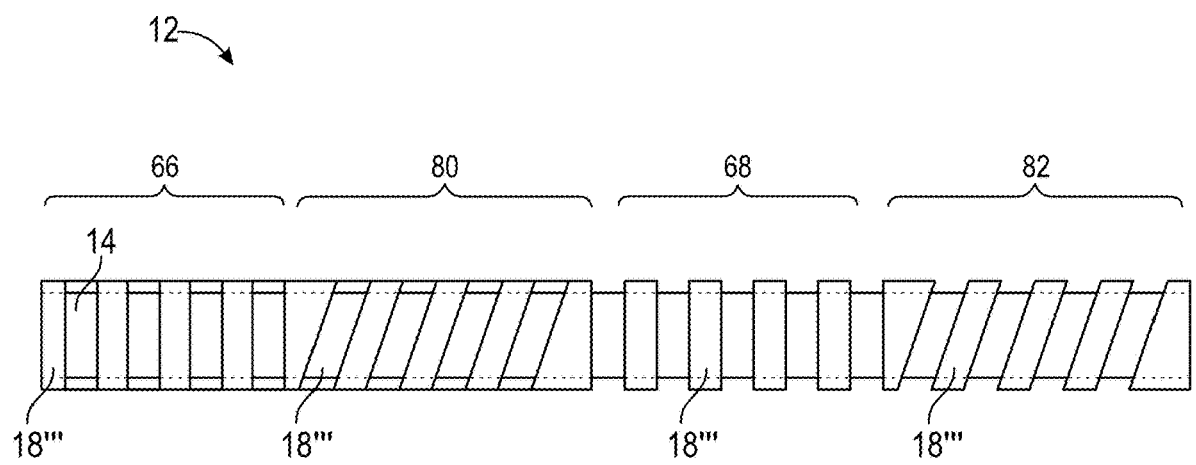
FIG. 26 presents a top view of a multi-segment rubber-reinforced actuator that contains multiple actuation motions, including a bending section 66, a bend-and-twist section 80, an extending section 68, and an extend-and-twist section 82.
Figure 27:
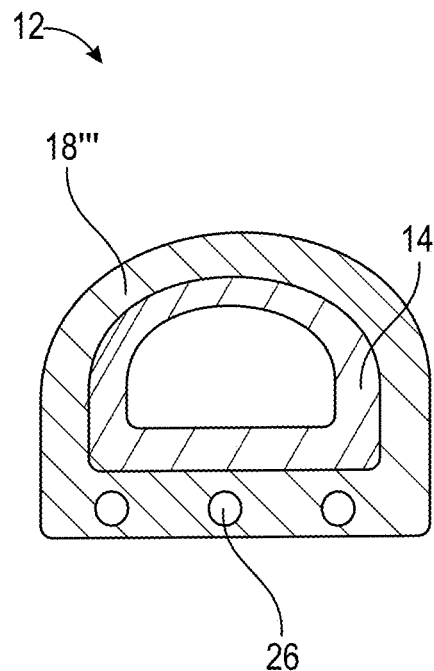
FIG. 27 shows a cross-section end view of a rubber-reinforced soft actuator with working channels 26.

Rubber reinforcements 18''' can be arranged to create the range of motions presented earlier. For example, FIG. 26 presents a top-view schematic of the rubber reinforcement 18''' with sections configured to produce bending 66, bending-and-twisting 80, extending 68, and extending-and-twisting 82 in a single actuator 12, wherein each section includes a plurality of radial bands and a different configuration of the overall reinforcement structure to produce the different motions. The rubber reinforcement 18''' can also enhance the functions of the actuator 12. For example, in FIG. 27, the rubber reinforcement 18''' can have a working channel 26 (e.g., passing fluids, guiding instruments) or can be made of a different material with light-transmitting capabilities, such as a light pipe.

Figure 28:
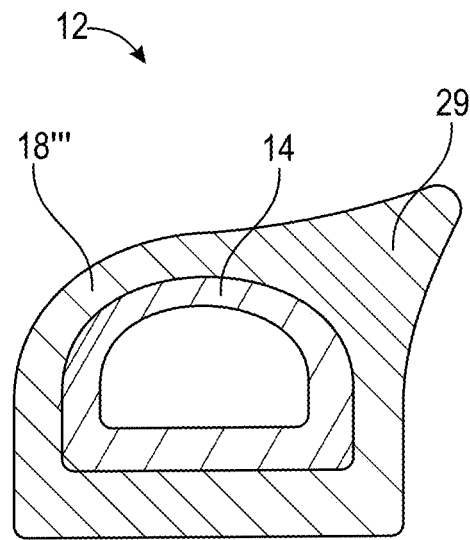
FIG. 28 shows a cross-section end view of a rubber-reinforced soft actuator where the reinforcing layer 18''' has other geometrical features 29.

In another example, FIG. 28 illustrates the rubber reinforcement 18''' with a geometrical feature 29 that can be used to enhance the capabilities of the actuator 12 for grabbing, conforming to a shape/object, positioning, and so on. Geometric features 29 can be over-molded on fiber-reinforced actuators as well. Mating features can also be molded into the reinforcement 18''' for mounting to an object or to another soft actuator 12. Mating features can be useful, for example, in situations where an actuator 12 must be passed through a small opening and assembled on the other side to achieve the task (e.g., laparoscopic surgery, search and rescue).

Figure 29:
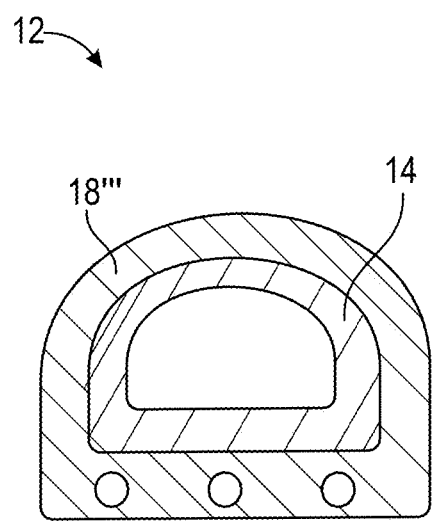
FIG. 29 shows a cross-section end view of a rubber-reinforced soft actuator where the lower-durometer rubber soft actuator body 14 does not need to have a closed cross-section.
Figure 30:
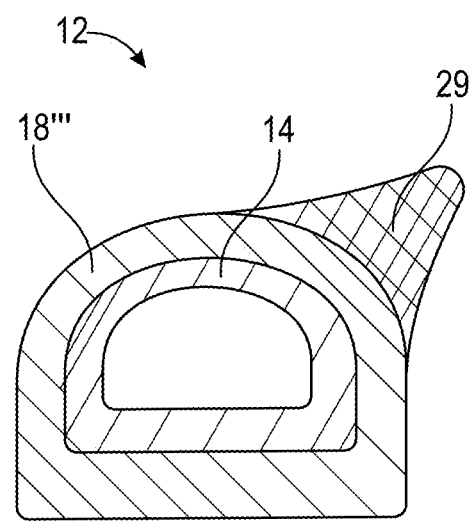
FIG. 30 shows a cross-section end view of a rubber-reinforced soft actuator where the geometrical feature 29 is made of a material that has a composition that differs from and that has at least one material property that differs from that of the reinforcing layer 18".

FIG. 29 illustrates that with the rubber reinforcement 18''', the lower-durometer rubber (i.e., the soft actuator body 14) does not need to have a closed cross-section, particularly if it has a good bond to the higher-durometer rubber. Use of an open cross-section can reduce the height of the actuator 12. In yet another example, FIG. 30 illustrates that the actuator 12 can be composed of more than two materials. For example, geometrical features can be created with a softer or harder material or with a material having a different color. In other embodiments, rigid parts can be co-molded into or to any of the actuators 12; such rigid parts can include electronics, light emitting components, sensors, cutting tools, pneumatic or hydraulic connections, etc.

Figure 31:
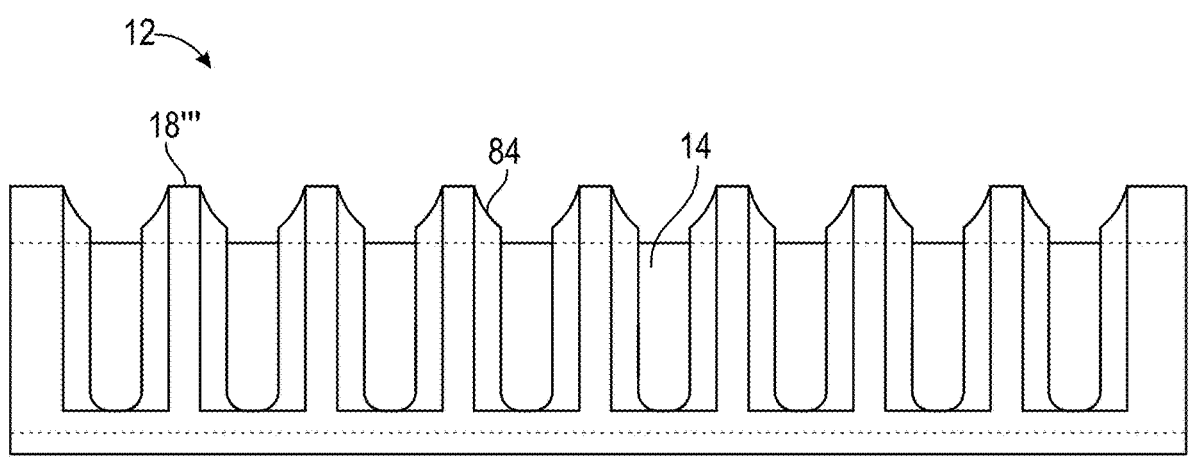
FIG. 31 shows a side view of a rubber-reinforced actuator where the reinforcement 18''' has a gradient profile 84 to spread stresses on a lower-durometer rubber soft-actuator body 14.
Figure 32A:
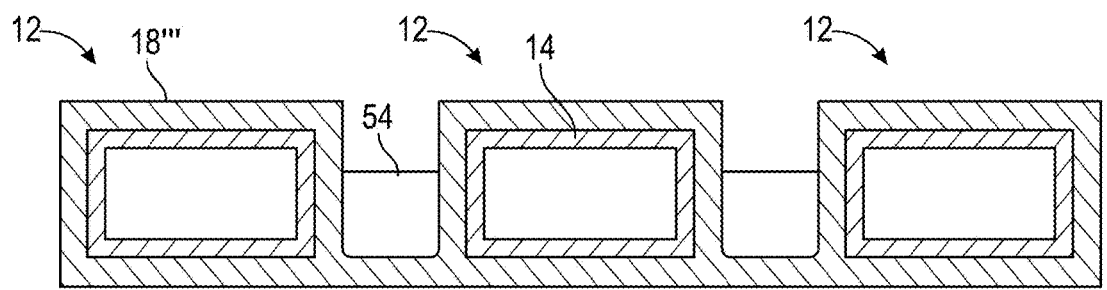
FIGS. 32a and 32b show perspective views of a rubber reinforcing layer 18''' joining multiple soft actuator bodies 14 into one structure.
Figure 32B:
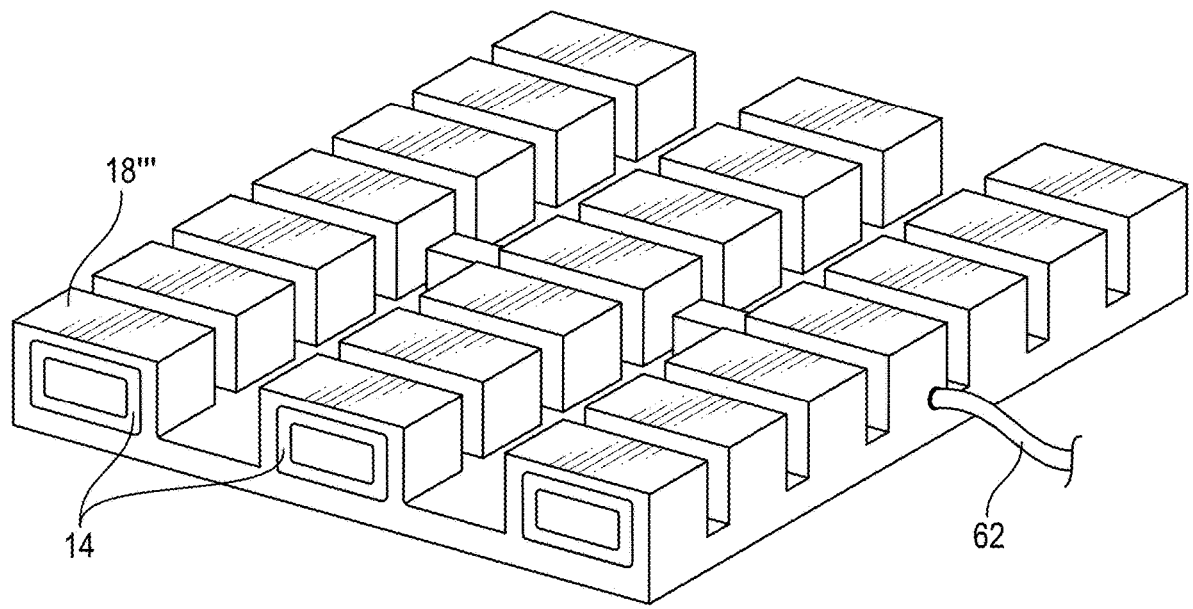

The reinforcing layer 18''' can also be molded into a range of shapes and profiles. For example, FIG. 31 illustrates the reinforcement 18''' with a gradient profile 84 to spread stresses on the lower-durometer rubber of the soft actuator body 14. The rubber reinforcement 18''' can also be used to join multiple actuators 12 and actuator types into one structure. FIGS. 32a and 32b illustrate this with cross-section and isometric views of three parallel rubber-reinforced bending actuators 12, each with a respective soft actuator body 14, all joined by a common pressurized fluid line 54.

Figure 33:
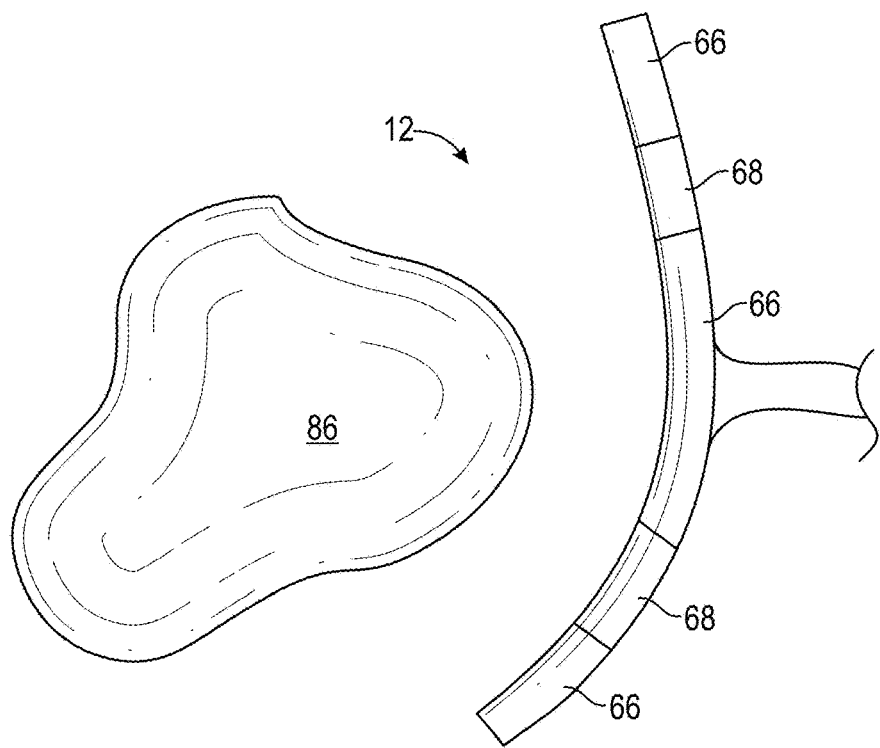
FIGS. 33 and 34 show a multi-segment actuator 12 designed to grab an object 86 by growing in size and curling around it.
Figure 34:
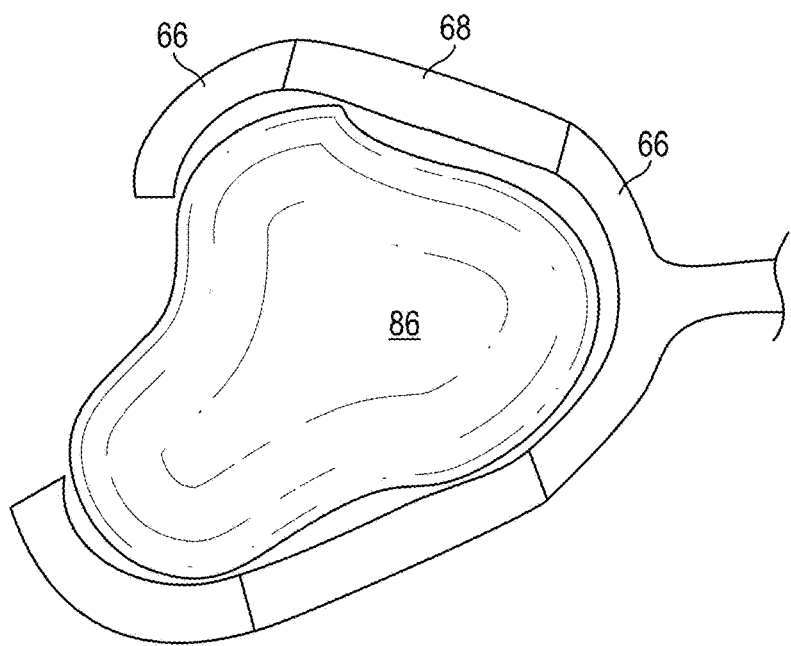

Soft actuators 12 are particularly well suited for handling delicate objects, such as soft tissue. The following examples demonstrate the strength of these actuators to grab, retract, and displace soft tissue. FIGS. 33 and 34 illustrate one application where a multi-segment soft actuator 12 is designed to grow in size and safely conform around an anatomical structure 86 for manipulation.

Figure 35:
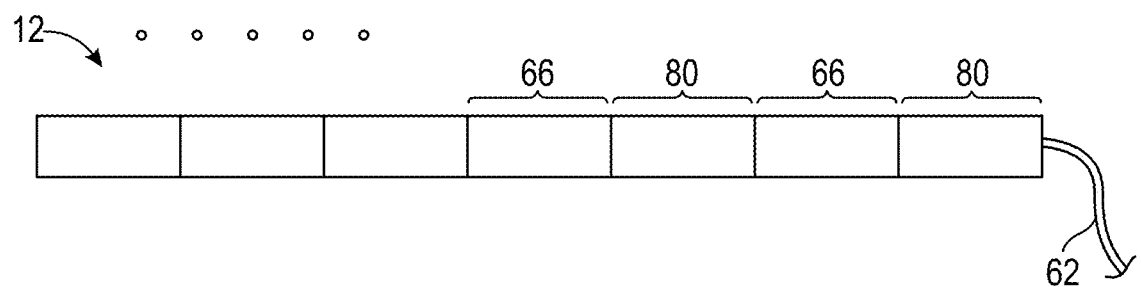
FIGS. 35 and 36 show a multi-segment actuator 12 designed to curl into a helical shape and grow in diameter under fluid pressurization.
Figure 36:
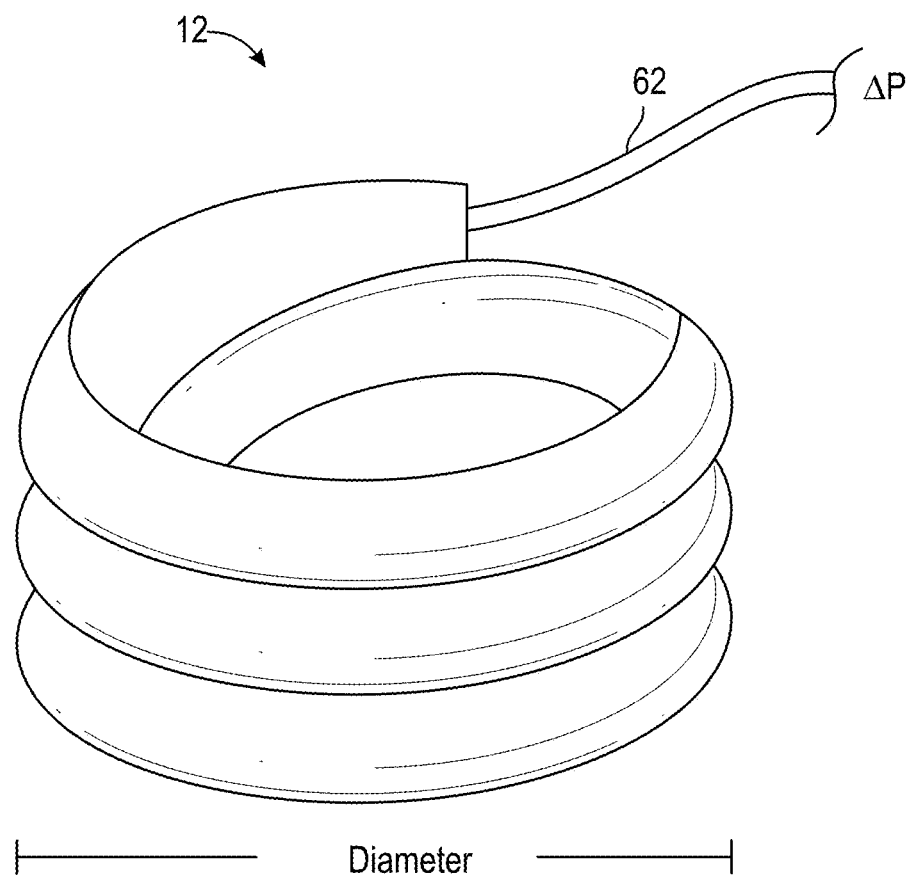
Figure 37:
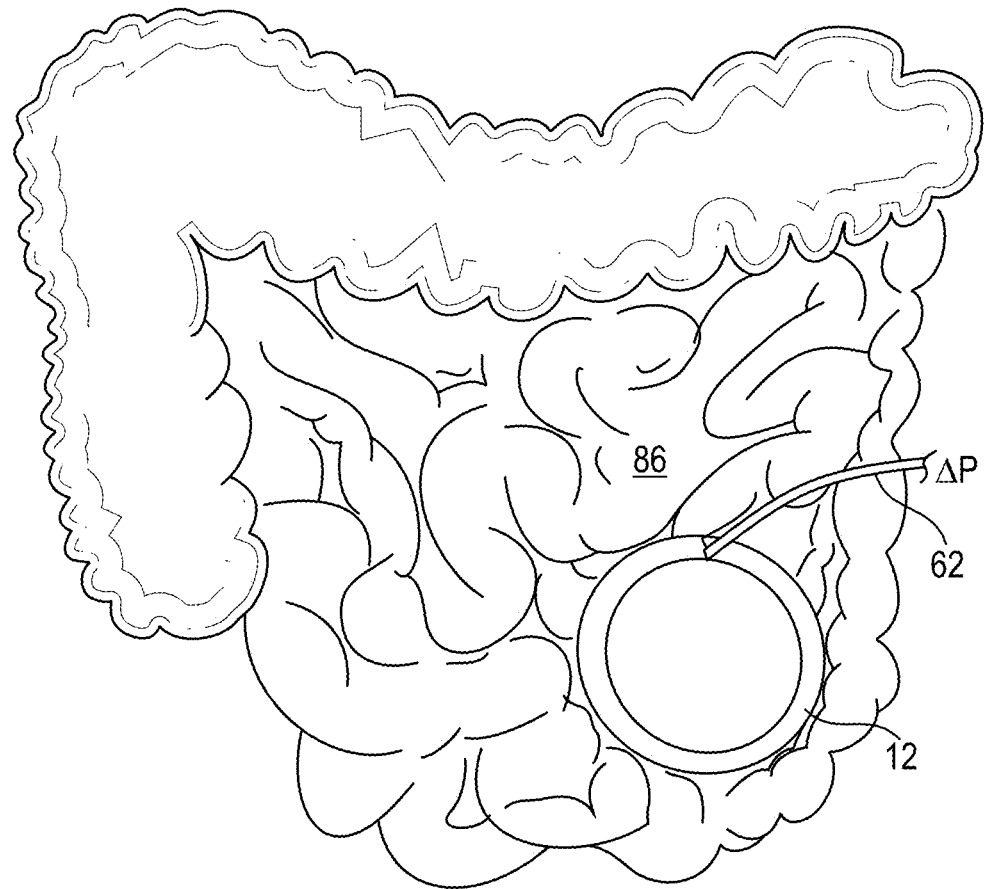
FIG. 37 shows the pressurized actuator 12 of FIG. 36 displacing anatomical structures 86.
Figure 38:
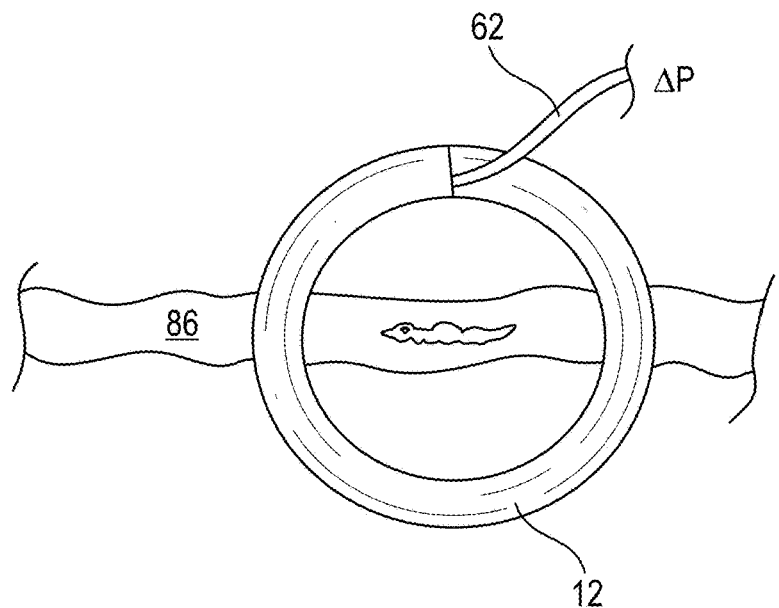
FIG. 38 shows a top view of the pressurized actuator 12 of FIG. 36 localizing and positioning a damaged soft tissue 86 (such as a vein or a section of intestine) for repair.
Figure 39:
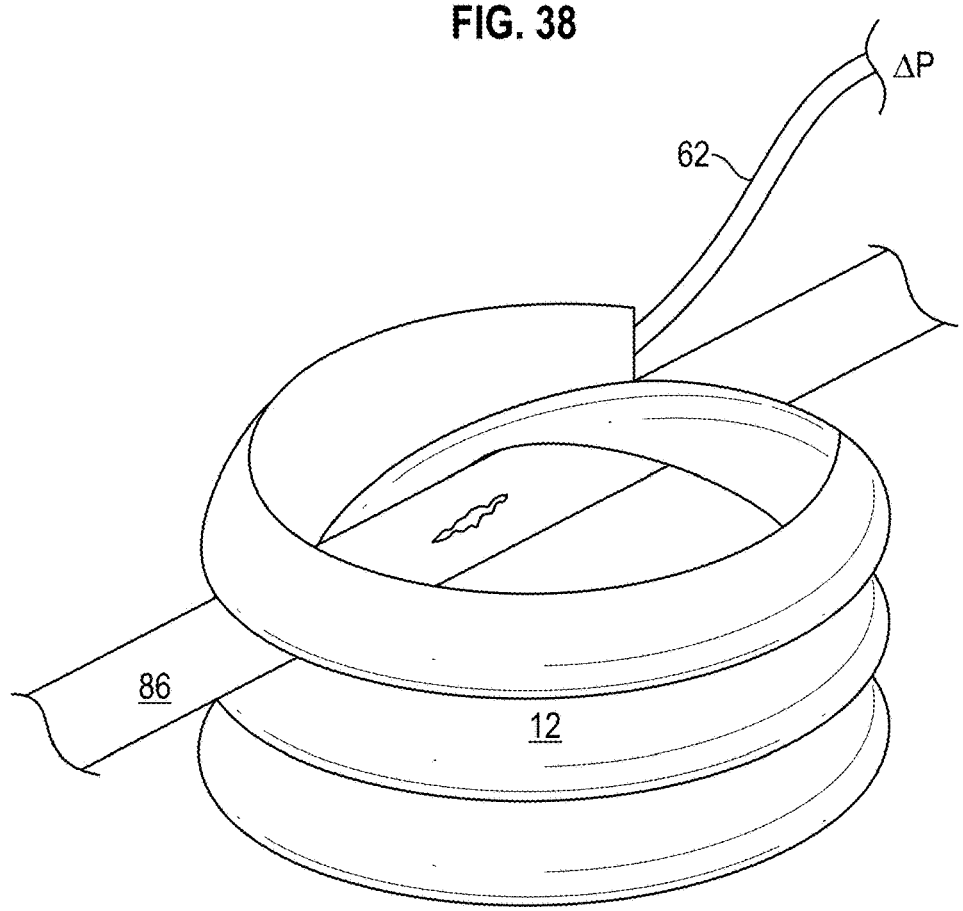
FIG. 39 shows an isometric view of the actuator 12 of FIG. 38.

FIGS. 35 and 36 illustrate a multi-segment soft actuator 12 composed of alternating "extending" segments 68 and "bending-and-twisting" segments 80 that, in their un-actuated state, can be passed through a small opening, such as a trocar, and in their actuated state, form a helical shape. The "bending-and-twisting" segments 80 cause the actuator 12 to assume a helical shape. The "extending" segments 68 can be used to control/program the diameter of the helix. In one application, the helical soft actuator 12 can be used to displace anatomical structures 86, such as the intestines, to create a clear operating zone (as shown in FIG. 37). In another application, the helical soft actuator 12 can be used to localize and position damaged soft tissue 86 (such as a vein or a section of intestine) for repair (as shown in FIGS. 38-39).

Figure 40:
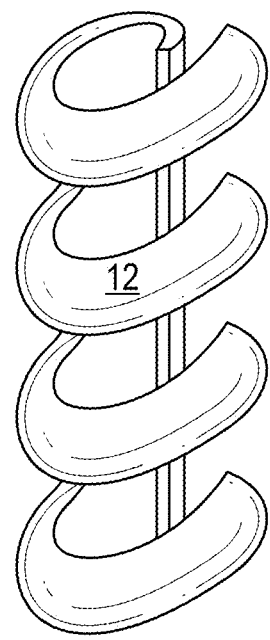
FIG. 40 illustrates a multi-fingered grabbing actuator 12.
Figure 41:
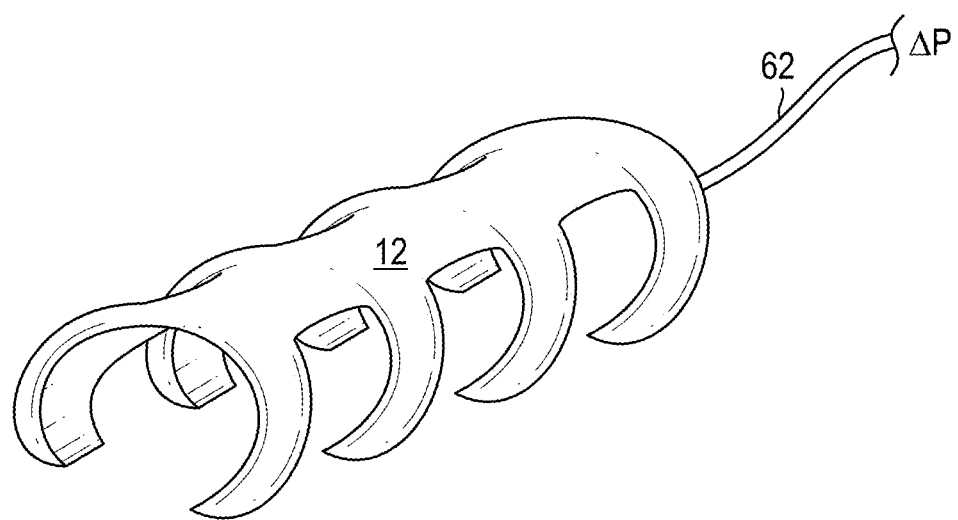
FIG. 41 illustrates a multi-fingered grabbing actuator 12 with opposing digits.
Figure 42:
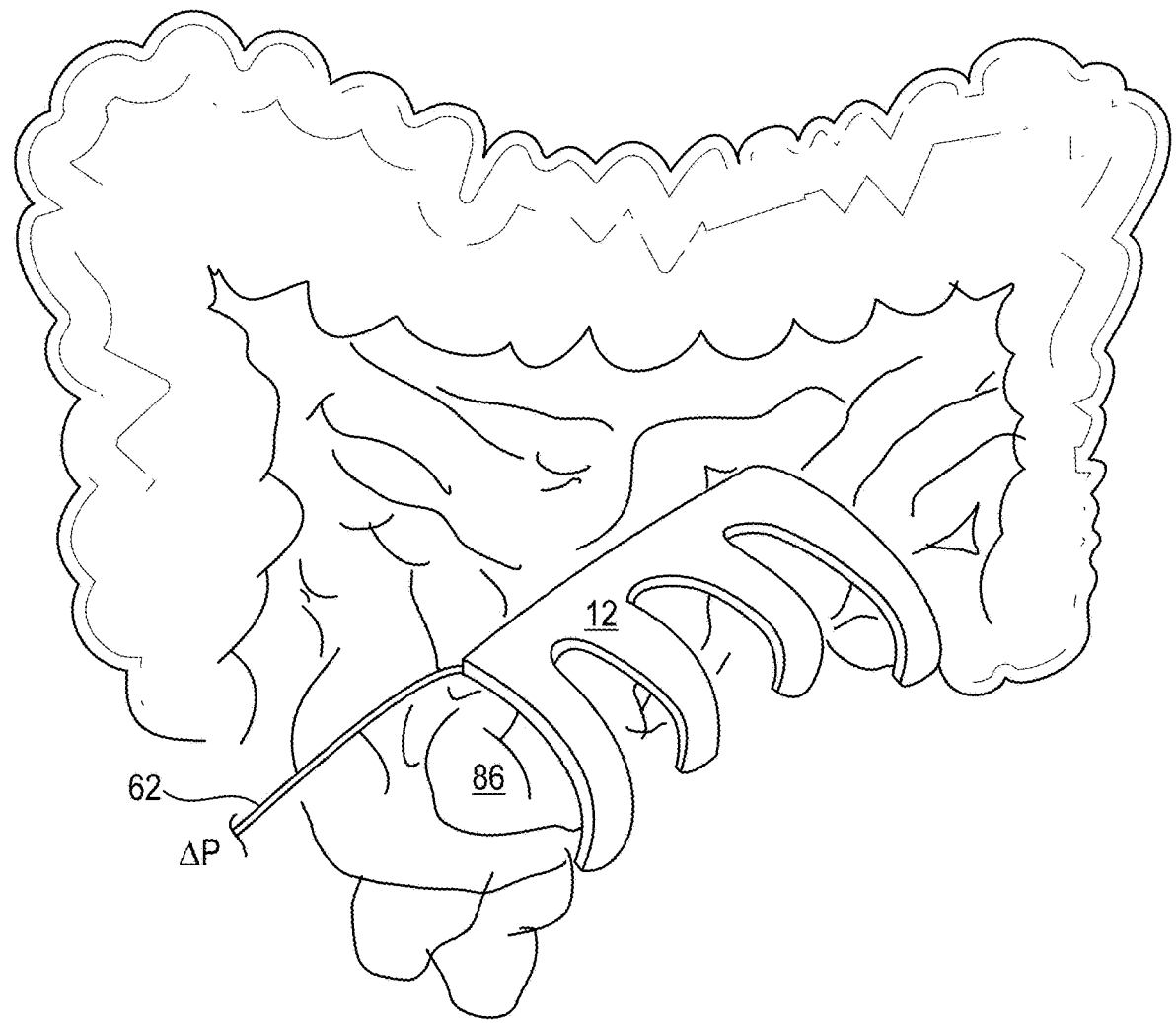
FIG. 42 illustrates the multi-fingered grabbing actuator 12 retracting intestines 86.

FIGS. 40 and 41 depict multi-segment, multi-chamber retractor devices that can be formed of one or more actuators 12 and that can be rolled up to a small cross-sectional profile; but when actuated, the devices can grab onto material over a large area. The digits can be composed of bending and extending segments. In one application, the retractor device can be rolled up, passed through a trocar, and pressurized to safely retract intestines for laparoscopic surgery (as shown in FIG. 42); this retractor device can also be used in open surgery.

Figure 43:
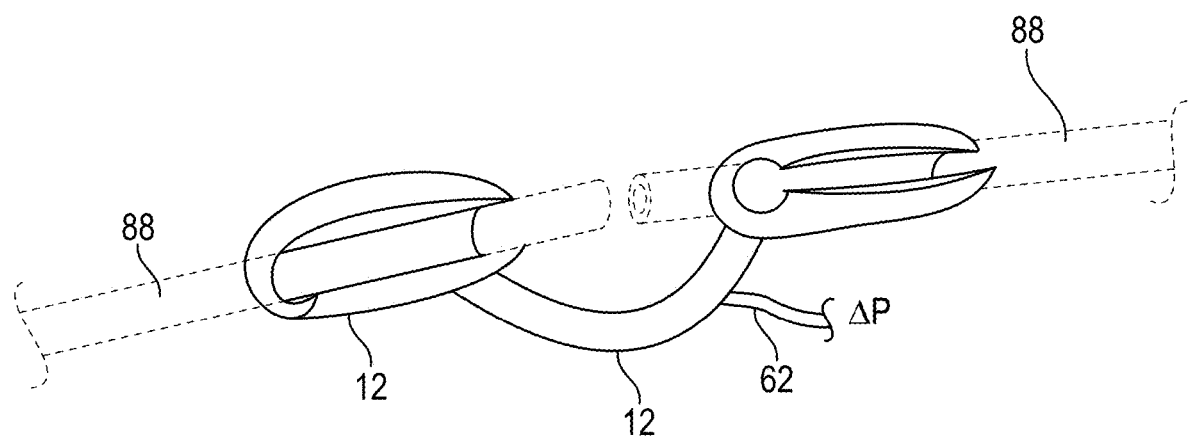
FIGS. 43 and 44 illustrate multi-segment soft actuators 12 designed to bring the ends of two tubes 88 together for joining.
Figure 44:
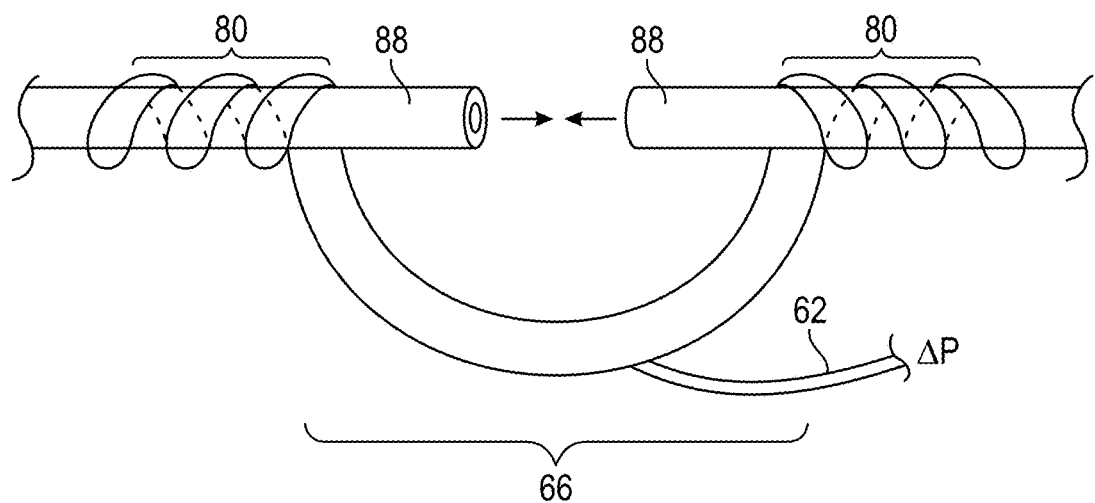
Figure 45:
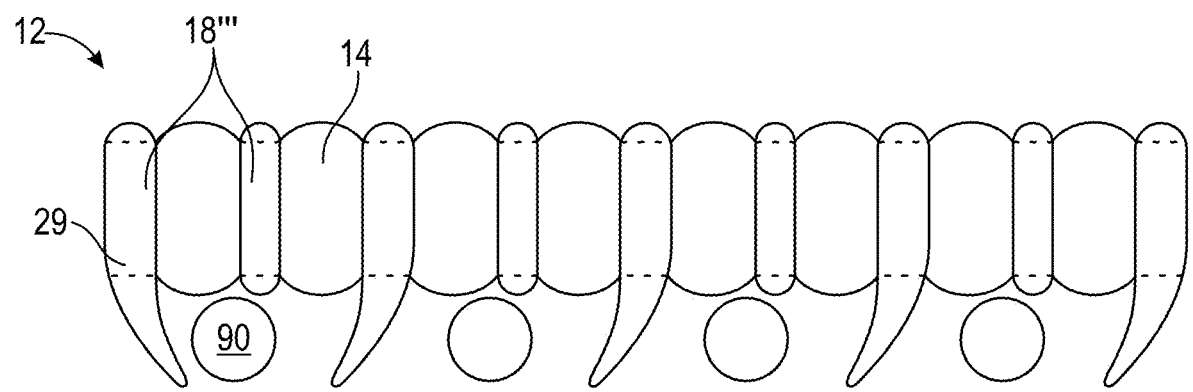
FIGS. 45 and 46 demonstrate a rubber-reinforced linear-extending soft actuator 12 with geometrical features 29 designed to gather objects 90 upon depressurization.
Figure 46:
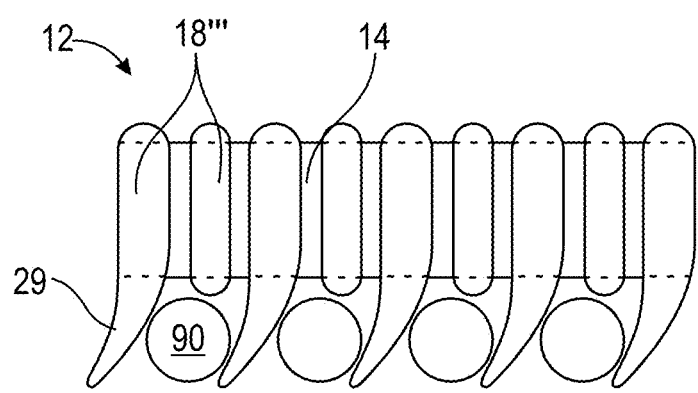

FIGS. 43 and 44 illustrate another application where multi-segment soft actuators 12 are designed to grab ends of tubes 88 and bring them close together for joining. This joining of tubes 88 is important, for example, during the anastomosis of damaged veins. Use of soft actuators 12 enable a large distribution of clamping pressure so as not to damage the vein. In another application, a geometrical feature 29 can be incorporated onto a linear actuator 12, as shown in FIGS. 45 and 46. When the actuator 12 is pressurized (as shown in FIG. 45), it can be draped over several objects 90 (such as intestines); after which, the pressure can be released, and the geometrical features 29 can be used to gather the objects 90 (as shown in FIG. 46).

Figure 47:
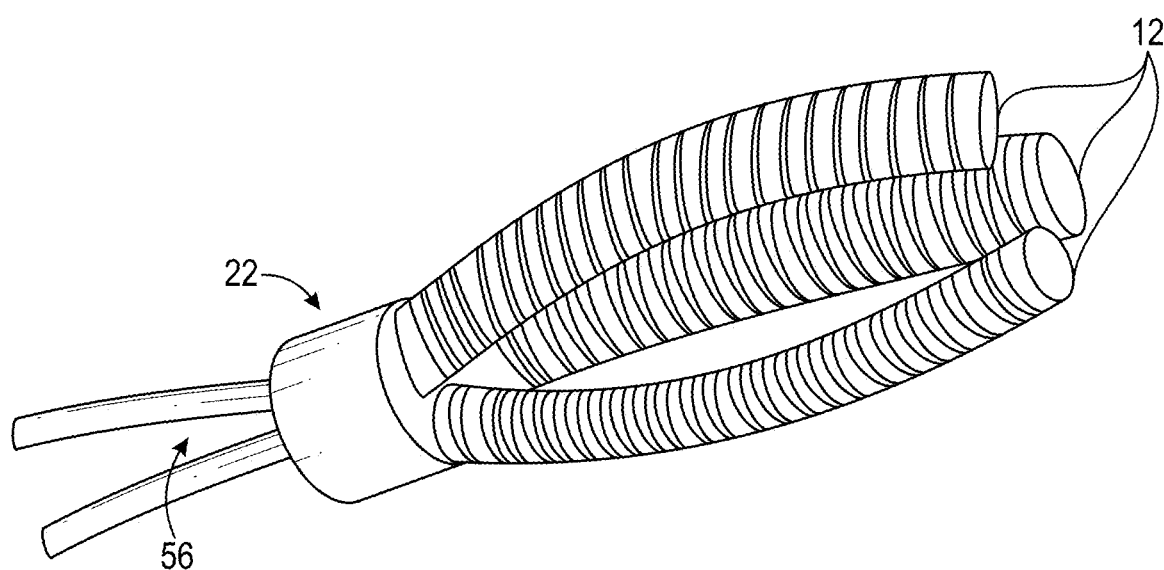
FIG. 47 is a drawing of a prototyped soft retractor, including multiple soft actuators 12 extending from a fixture 22.
Figure 48:
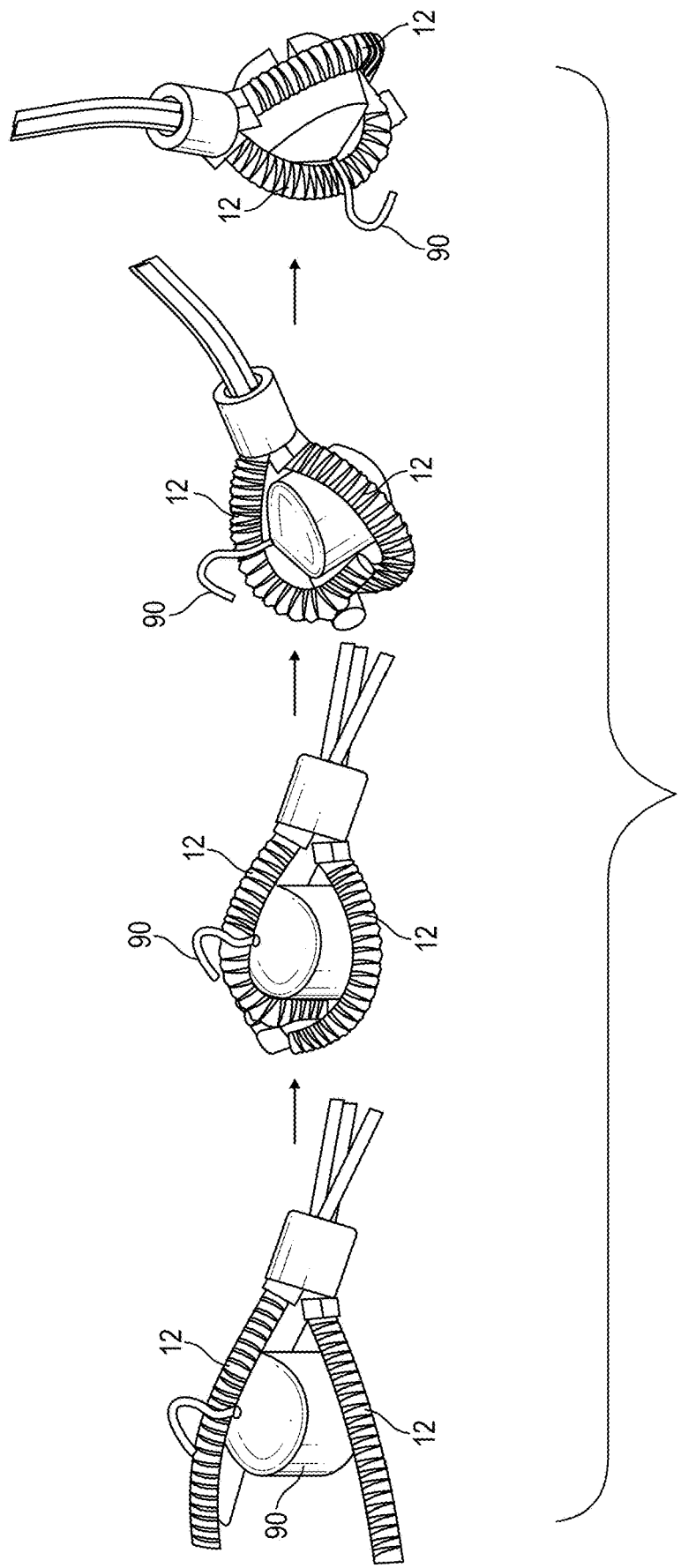
FIG. 48 presents a series of drawings demonstrating the operation of the soft retractor of FIG. 47 to grasp an object 90.

In another application, FIGS. 47 and 48 present the design and preliminary evaluation of a soft tissue/organ retractor 56 suitable for minimally invasive procedures. Minimally invasive procedures involve making small incisions in a patient's abdomen to gain access to internal organs with minimal trauma. Numerous medical disciplines have adopted these new procedures and have demonstrated that they can reduce hospital stays and improve recovery times while accomplishing the same results as in open surgeries. However, realization of these procedures requires the miniaturization of surgical tools and instruments. Due to size restrictions, these tools have usually been made of metallic materials that make them sharp, clunky, and increases the risk for intraoperative complications, as these tools are not suitable to be used as retracting and/or manipulating tools for organs and tissue.

The proposed retractor 56 (an embodiment of which is shown in FIG. 47) is composed of the following three main modules: a) the three manipulating fingers (segmented soft actuators 12), b) the base fixture 22 that acts as the handle for holding and positioning the retractor, and c) the lines 62 for pressurized fluid supply to the bending actuators 12.

This design features three compliant bending and extending actuators 12 as fingers and can be deployed into the patient's abdomen through a trocar port. Inside the abdomen, the surgeon can use existing laparoscopic instruments to hold the retractor 56 from its base fixture 22 and to position the retractor 56 on top of the area of interest for retraction. There, the three actuators 12 can be pressurized by means of a pressurized fluid (water or air) to conform around the organ's geometry. Thus, the retractor 56 relies on geometric trapping to manipulate tissue, rather than friction or pinching. In this way, stable and safe means for manipulation are provided.

Utilizing the soft and compliant nature of the actuators 12, a large contact surface area over complex soft tissue geometries can be achieved. The device can be extended to also include a twisting ability using or more twisting actuator segments for even more compliant grasping of soft tissue. Once pressurized, a quick-release connector can be used to detach the retractor 56 from the pressure supply line 62, allowing it to be used without requiring an additional incision for a trocar port. A preliminary test is presented in FIG. 48, where the developed prototype retractor 56 demonstrates a stable grasping and subsequent lifting of an object 90 that weighs 200 grams. Such a device can potentially reduce the risk of tissue damage and intraoperative hemorrhage by providing the surgeon with a soft, compliant interface between delicate soft tissue structures and the sharp laparoscopic forceps and graspers that are currently used to manipulate and retract.

This and other retractor 56 designs that incorporate the soft actuators 12 of this disclosure can also be advantageously used in a variety of other contexts. For example, the retractor can be incorporated into a robot to provide the robot with a human-like soft manipulation appendage. In additional applications, the retractor can be utilized in environments that are hazardous or otherwise unsuitable for humans; for example the retractor can be used on a deep-sea submersible vessel where it can be used to manipulate objects (e.g., on the ocean floor) at depths that humans can not readily achieve via standard scuba equipment.

In another application, the soft actuator technology can be used to prevent and rehabilitate musculoskeletal injuries. On average, a quarter of all adults will suffer a musculoskeletal injury (e.g., inflammation and pain, joint derangement, joint derangement with neurological involvement, stress fracture, sprain/strain/rupture, dislocations and so forth) during a 12-month period with the knee joint being the most likely affected, accounting for 23.2% and 22.3% of all musculoskeletal injuries among men and women, respectively. Within the military, musculoskeletal injury statistics are worse due to intense training and supporting pack loads up to 45 kg. In fact, in a study of the 743,547 musculoskeletal injuries reported among the U.S. armed forces, 67% were classified as resulting from overuse and 75% of all injuries were lower extremity overuse injuries resulting from running, marching, and other load bearing activities. There are products on the market that are designed to prevent injuries, such as twisting hyperextension and (to a lesser degree) impact forces; but we know of none of that are designed to prevent overuse injuries.

Figure 49:
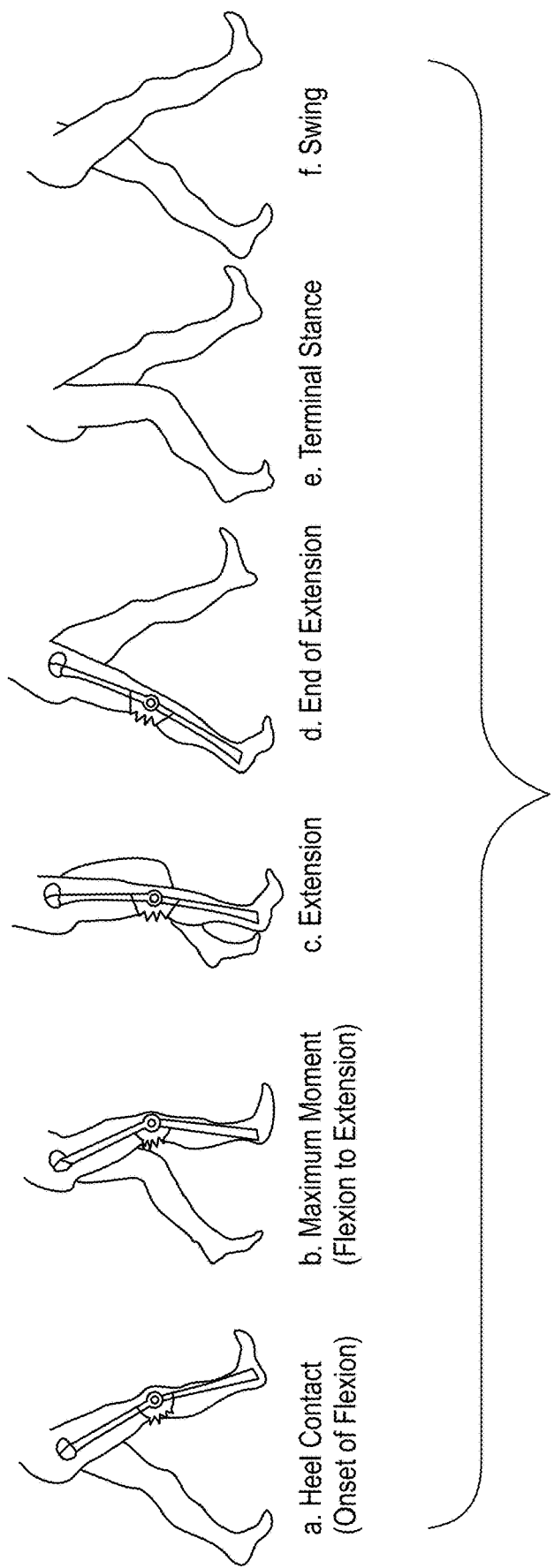
FIG. 49 presents an illustrated time-lapsed side view of a typical walking gait cycle of a human.

One approach for preventing overuse injuries is to relieve the stresses on the musculoskeletal system by supporting the joint (i.e., introducing forces) to reduce the mechanical forces the user must generate. In a normal walking gait cycle (as shown in FIG. 49) there are two main phases: the stance and swing phase. As shown in FIG. 49, during the stance phase, the foot is always in contact with the ground, whereas it is never in contact with the ground during the swing phase.

The stance phase consists of knee flexion and extension phases. During flexion, as the heel strikes the ground, as shown in image (a) of FIG. 49, the knee experiences high torques in order to decelerate and support the body. The angle of knee deflection increases during flexion until its maximum angle of deflection and, therefore, its maximum amount of torque is reached. The angle of maximum deflection depends on the physical characteristics of the walker and the load being supported by the user. The angle of maximum deflection increases as the load being supported increases. After flexion, the angle of knee deflection decreases during the extension phase, shown in image (c) of FIG. 49 of the gait cycle. During extension, the knee exerts torque on the thigh and shin to straighten the knee and propel the walker to the next step. At the end of extension, as shown in image (d) of FIG. 49, stance is terminated, and the leg is allowed to swing freely until contact is made with the ground. Therefore, during flexion and extension, a device can provide needed support to prevent injury.

Figure 50:
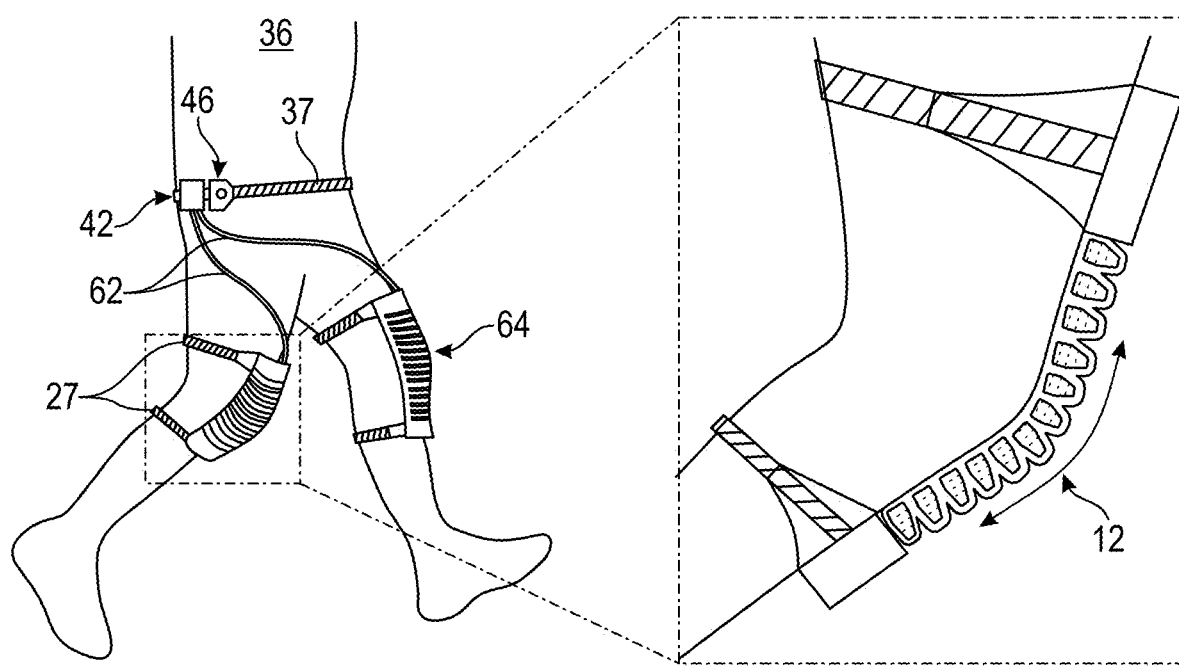
FIG. 50 is an illustration of an active knee orthosis device 64 that uses soft actuators 12, as shown in the magnified inset, to support knee bending during locomotion.

FIG. 50 presents a soft actuated, wearable assistive knee device 64 designed to reduce work required by the wearer's muscles. The proposed solution uses multi-segment fiber-reinforced elastomeric soft actuators 12 that conform to the knee and apply a supportive torque during the flexion and extension phases of the gait cycle. The device 64 can be secured around the leg of the wearer 36 with straps 27; and the wearer 36 can also wear a belt 37 on which the fluid pump 42 and microcontroller 46 for pumping fluid into the actuators 12 can be mounted. There are several other notable features of this actuation technology for wearable applications. For example, these actuators 12 are resilient to impacts due to their rubber construction; they have an extremely low fabrication cost; and they can be fabricated in various sizes and shapes to accommodate dimensioning of every possible human limb/joint (not just the knee). Furthermore, when the device 64 is not actuated, it is flexible and does not inhibit the knee during the swing phase of the gait cycle. The soft material construction also closely matches the compliance of soft tissue, which minimizes complications caused by pressure points (typically a problem with rigid solutions).

This soft knee orthosis 64 has applications beyond preventing overuse injuries. For example, it can be used in rehabilitation for individuals that have disabilities as a result of an injury or a medical condition. The soft knee orthosis 64 can be used to restore function through exercises and with continued usage to lead to motor memory that will train the user to use limbs again without the device 64. Among the elderly or those with muscular degenerative diseases, it can be a device to compensate for lost muscle mass. Furthermore, the device 64 can be designed to provide resistive forces rather than as an assistive part of rehabilitation or as part of strength training.

Figure 51:
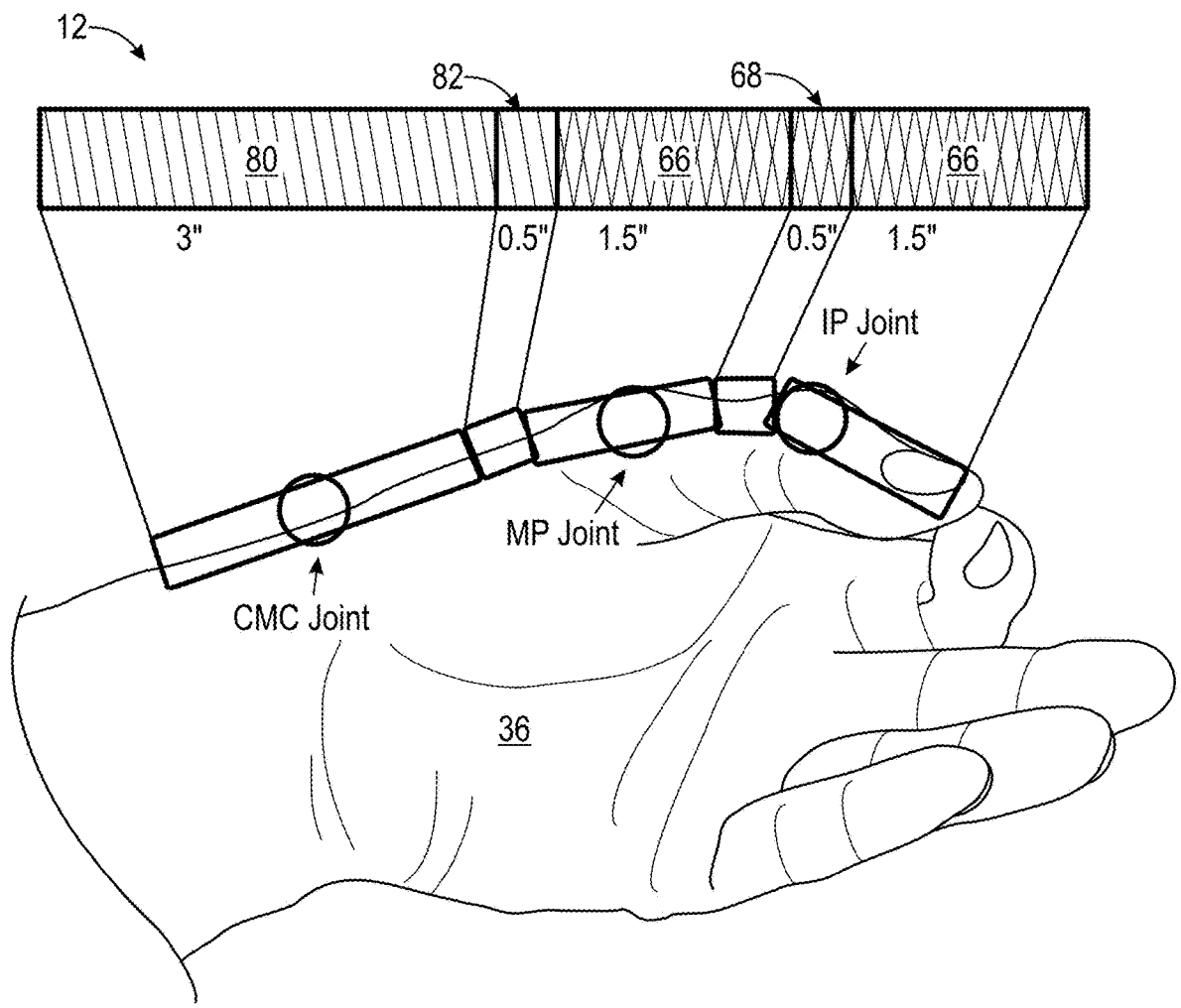
FIG. 51 is a combination image of a hand and wrist of a user 36 and an over-laid image of a segmented soft thumb actuator 12 specifying the joints in the thumb that each segment supports; the length of each segment (in inches) is also shown.

In another particular application, a multi-segment soft actuator 12 can be used to power assist the thumb, as shown in FIG. 51. The human thumb is integral in object grasping and happens to be the hardest digit to mechanically assist due to its unique range of motions (i.e., bending: 25°-75°; extension: 7.62 mm-12.7 mm; and twisting: 15°-25°). Presented herein is a soft-actuated solution to assist the thumb; this solution, however, can be readily extended to the remaining digits and, in additional embodiments, to other joints, such as the wrist.

Soft actuators 12 of this disclosure can be mechanically programmed during the manufacturing phase to achieve a wide range of motions, such as extension, contraction, twisting and bending. These actuators 12 can incorporate multiple motions into a single actuator 12 so that only one actuator 12 is required to replicate the motion of the thumb by using a multi-segment fiber-reinforced soft actuator 12 constructed from multiple types of strain-wrapping geometries along the length of a single actuator 12 to replicate the thumb's range of motion. This design offers the benefit of building complexity into the body of the actuator 12 and reducing control input complexity as well as mechanical complexity (e.g., no linkages, no rigid elements, no moving parts, etc.). Multi-segment actuators 12 are particularly well suited for actuating multi-degree-of-freedom joints, such as the human thumb, where concerted motion is desired. Each segment 80, 66, 82, 66, 68, and 66 can be designed to support specific joints [e.g., carpometacarpal (CMC) joint, metacarpophalangeal (MP) joint, and interphalangeal (IP) joint] in the thumb since each joint is responsible for a certain bending, twisting, and extension in oppositional grasping, as shown in FIG. 51. In this embodiment, the bend-and-twist section 80 at the CMC joint has a length of about 7-8 cm (3 inches); the adjacent extend-and-twist section 82 can have a length of about 1-1.5 cm (0.5 inches); next, the first bending section 66 can have a length of about 3.5 to 4 cm (1.5 inches); next, the extending section 68 can have a length of about 1-1.5 cm (0.5 inches); finally, the second bending section 66 can have a length of about 3.5 to 4 cm (1.5 inches).

Figure 52:
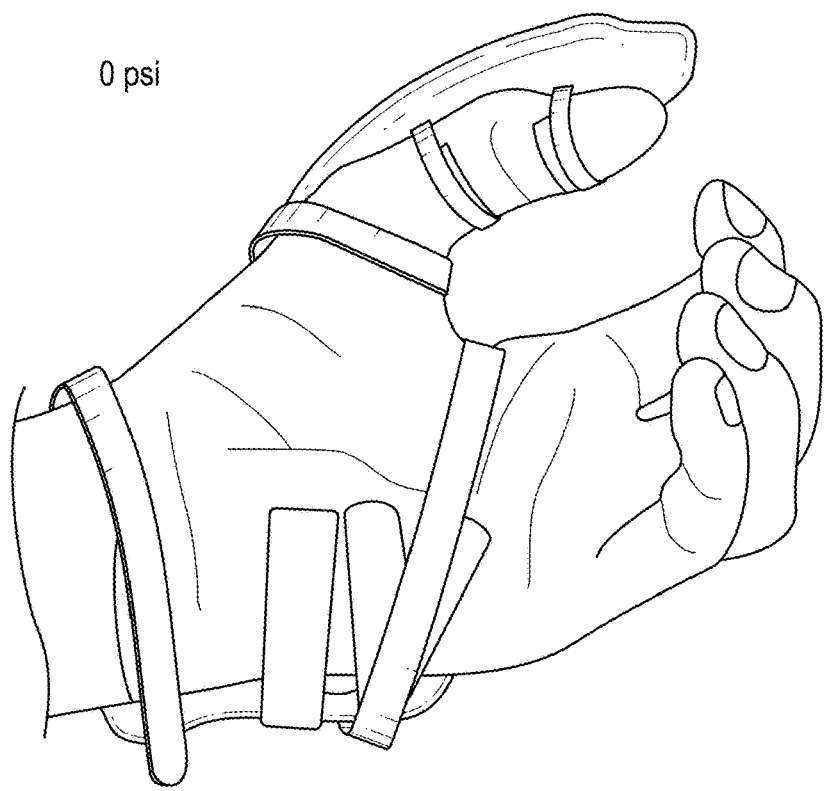
FIGS. 52 and 53 are images of a prototyped multi-segment fiber-reinforced soft-actuated thumb rehabilitation/assistive device worn on a user's hand and pressurized, respectively, at 0 psi and at 33 psi.
Figure 53:
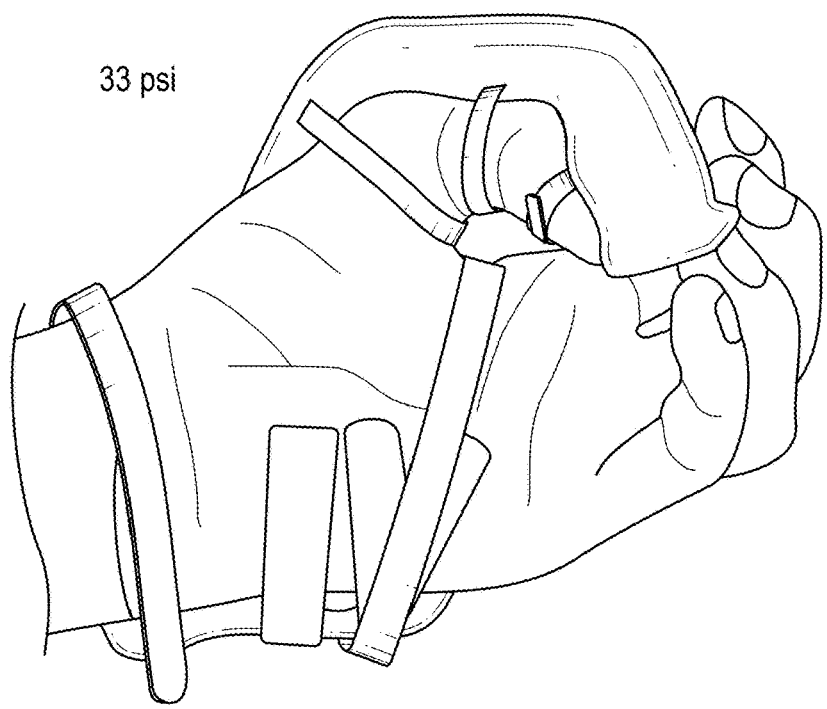
Figure 54:
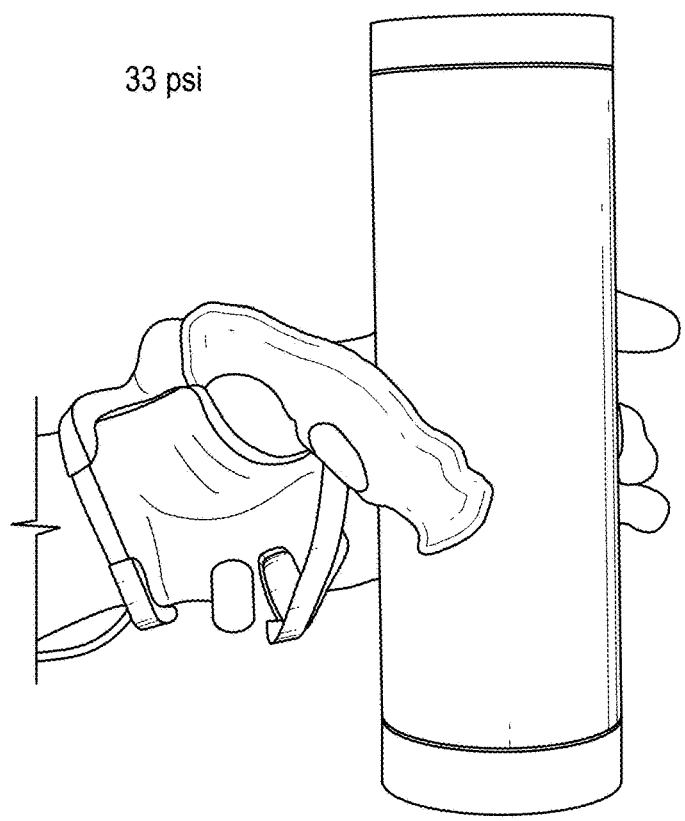
FIGS. 54-56 show the device of FIGS. 52 and 53 gripping various objects when actuated at a pressure of 33 psi.
Figure 55:
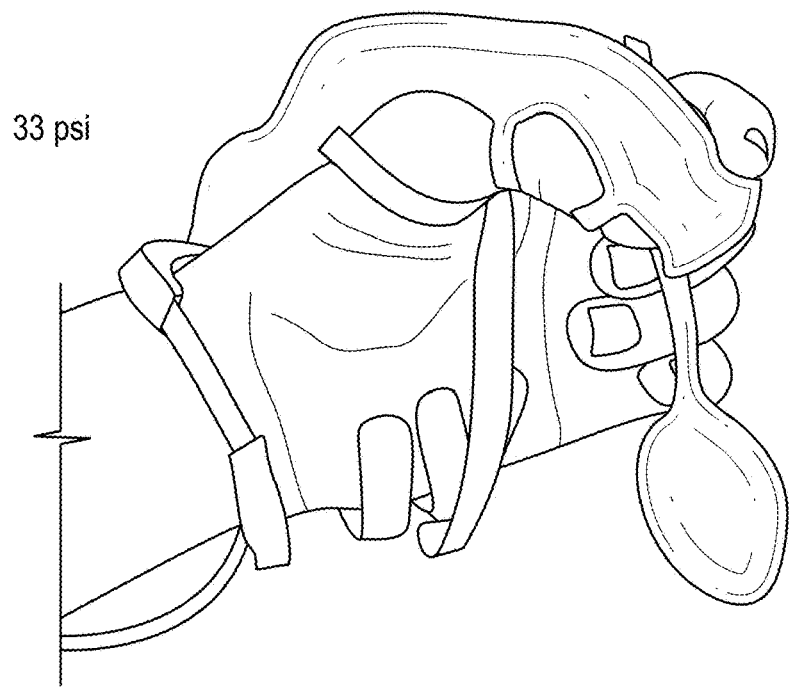
Figure 56:
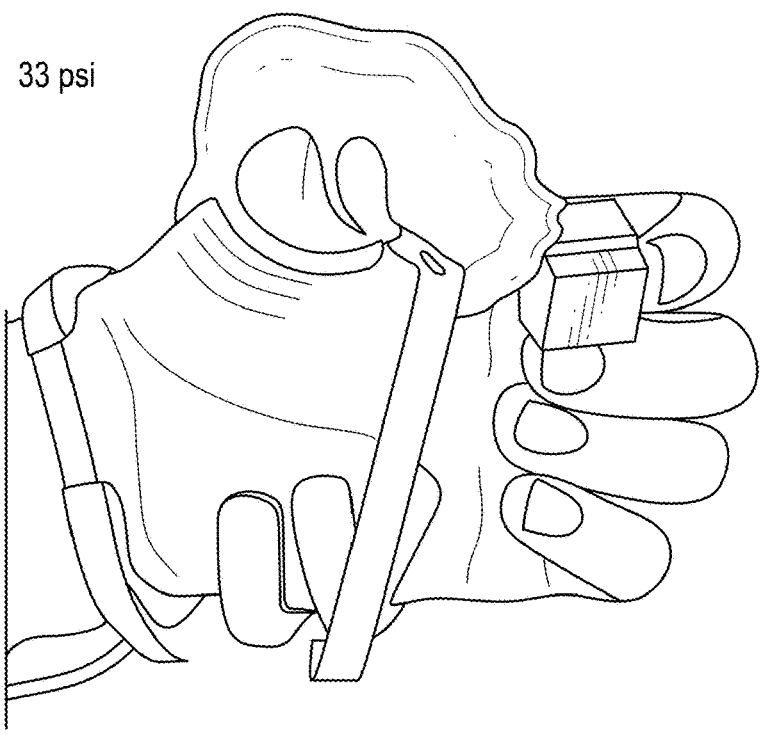
Figure 57:
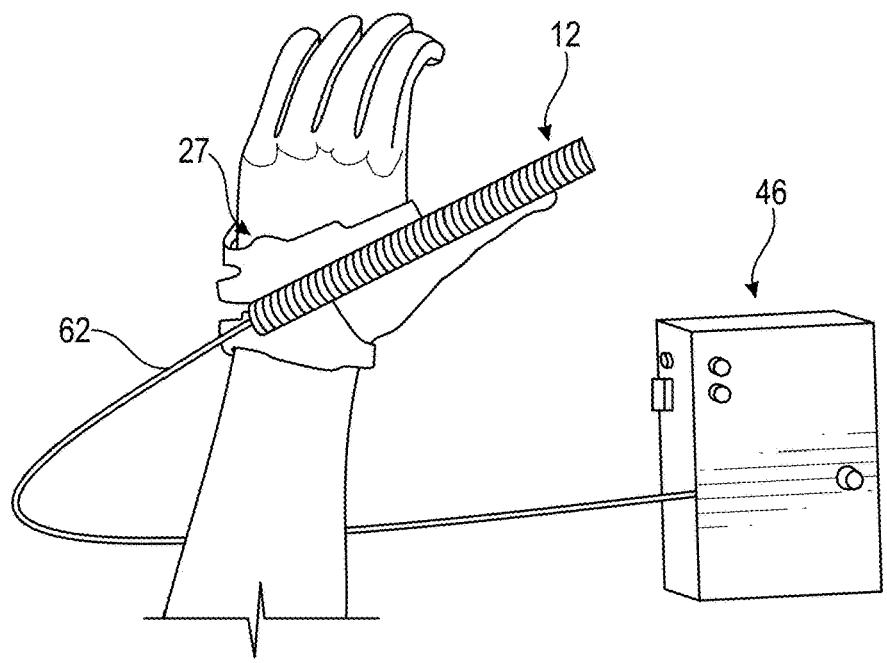
FIG. 57 illustrates a simplified embodiment of a system that includes an actuator 12 attached to the hand via an attachment structure 27 and a control system 46 with a pneumatic or hydraulic pump, batteries, valves, a microcompressor, pressure sensors, etc.

One embodiment of this thumb rehabilitative/assistive device is presented in FIGS. 52 and 53, where the multi-segment actuator has been designed to support the natural motion path of the thumb and for grasping objects, as shown in FIGS. 54-56. A simplified embodiment of an entire actuation system is shown in FIG. 57, where the actuator(s) is/are attached to the hand via an attachment mechanism 27, and wherein the actuator(s) is/are governed by a control system 28 including a pneumatic or hydraulic pump, batteries, valves, microcompressor, pressure sensors, etc.

Figure 58:
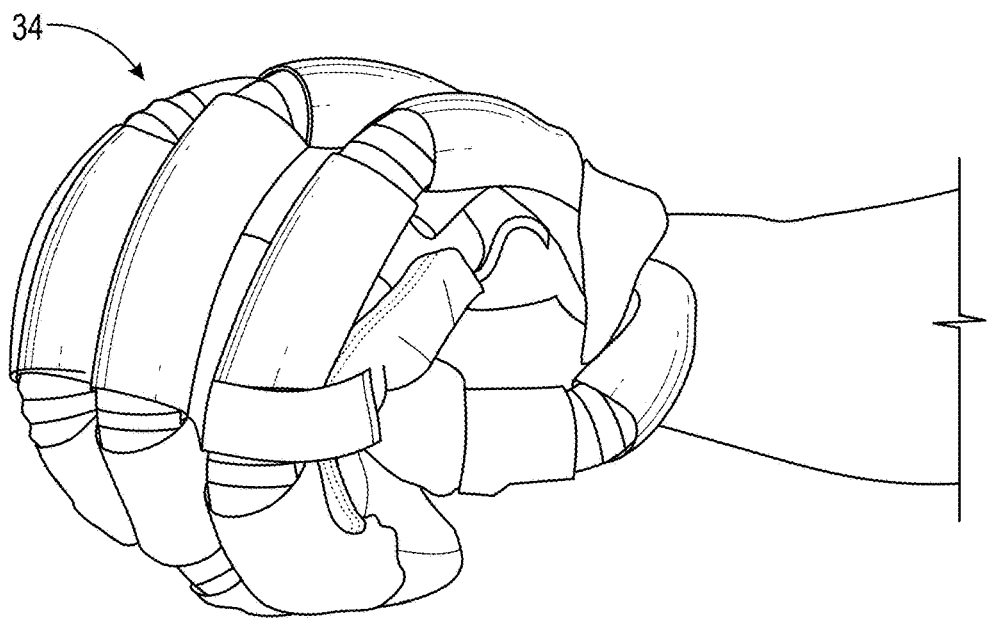
FIGS. 58 and 59 are images showing a proof-of-concept prototype of a glove 34 including multi-segment soft actuators 12 applied to all of the fingers to support the hand in closing a fist.
Figure 59:
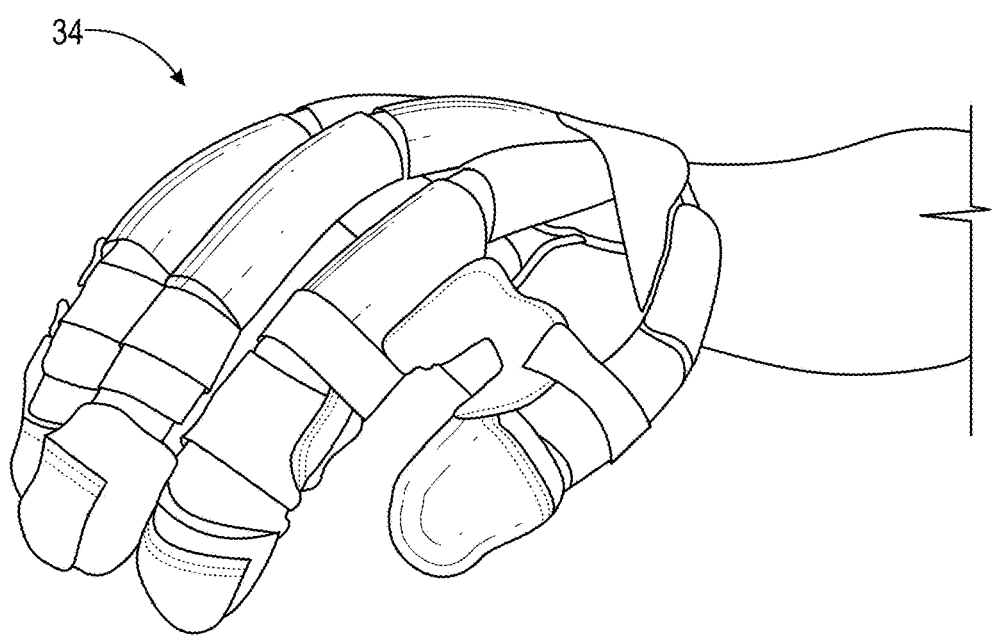
Figure 60A:
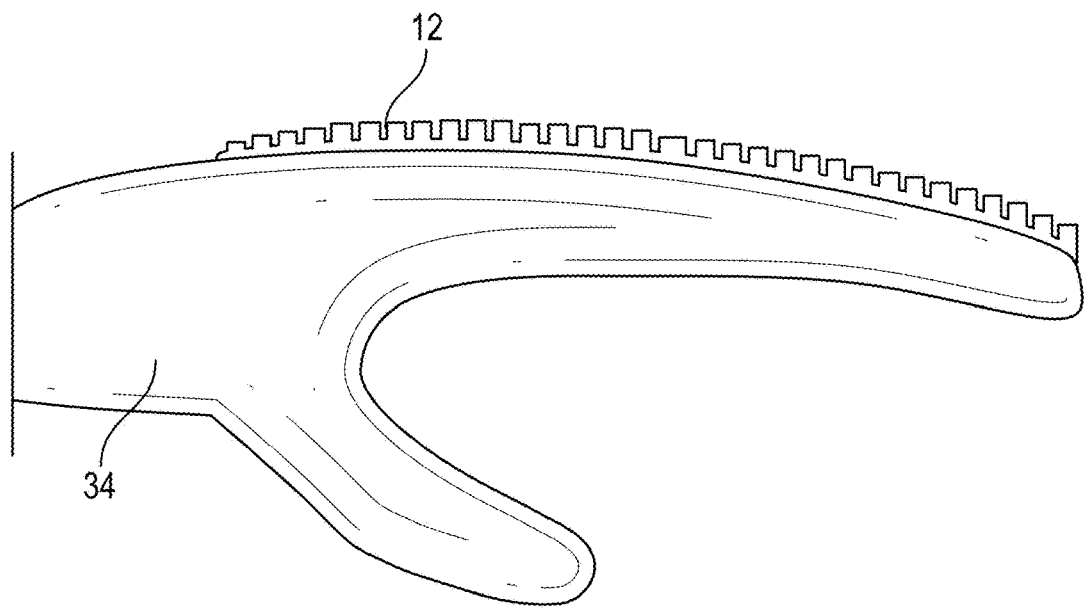
FIGS. 60a and 60b are side-view illustrations showing the support that a soft actuator 12 can provide in closing a hand, with the soft actuator 12 un-pressurized in FIG. 60a and pressurized in FIG. 60b.
Figure 60B:
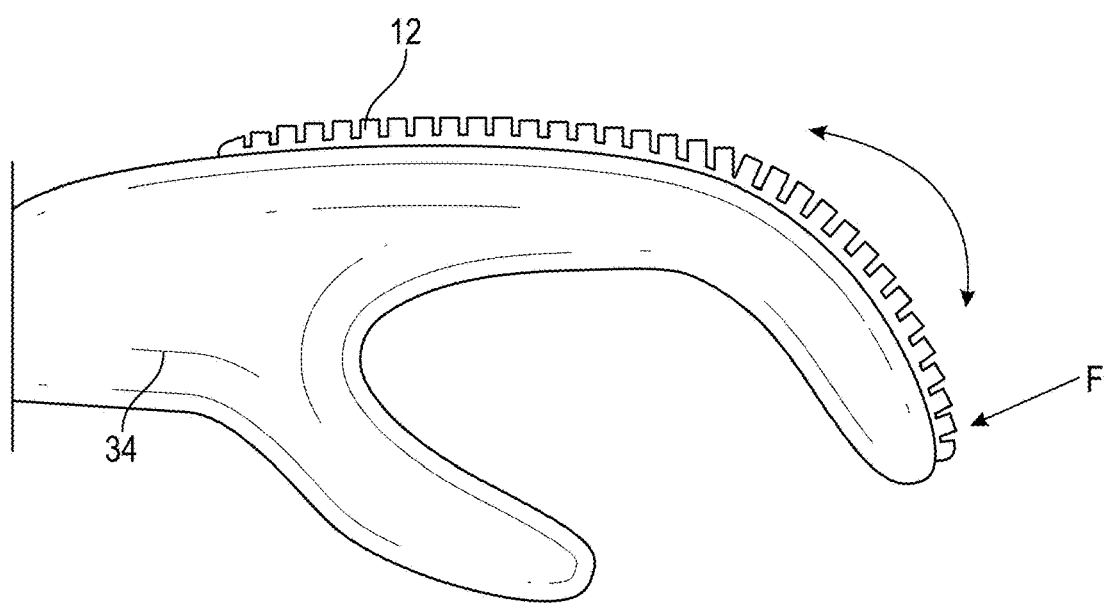

The soft actuated thumb-assistive device can also be extended to support the natural motion of the other digits of the hand, where a multi-segment actuator combines bending and extending motions to help close the hand, as shown in an early prototype glove 34 depicted in FIGS. 58 and 59 and in the illustrations of FIGS. 60*a* and 60*b*. Loss of the ability to move the fingers, whether partial or complete, can greatly inhibit activities of daily living and can considerably reduce one's quality of life. Though actuator segments are shown corresponding with each digit/joint of the fingers, the actuators 12 can alternatively be designed to cover and actuate some but not all of the joints of a thumb or other fingers (e.g., actuation may optionally not be provided for the most remote joint of a finger). Physical therapy can be effective in regaining controlled hand movement for a variety of disabling conditions, such as physical injuries, diseases, overuse syndromes and neurological damages.

Often rehabilitation for improving hand function requires the patient to perform repetitive task practice (RTP), which involves breaking a task down into individual movements and practicing these exercises to improve hand strength, accuracy, and range of motion. These methods, however, are labor intensive and costly due to the required long hours of training with a physical therapist. A system where patients can carry out exercises on their own, either at home or in clinic, would make physical therapy more accessible and therefore would be beneficial for patients. Studies indicate that stroke patients who have robotic assistance when performing intense repetitive movements can attribute significant improvement in hand motor functions to this assistance. The main challenge associated with developing a hand rehabilitation device is that traditional robotic devices use actuators that are less compliant than the joints themselves. These devices tend to be cumbersome and difficult to operate, mitigating the use of these devices by patients—particularly in a personal setting. To address these challenges, the design of a soft wearable robotic glove 34 for hand rehabilitation can lead to greater advances for assistive or augmented activity in the home by providing safer human-robotic interactions and reducing cost.

Figure 61A:
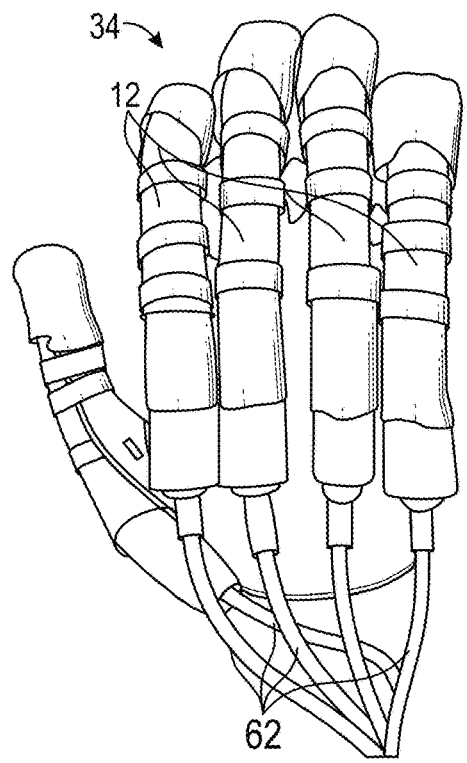
FIGS. 61a and 61b are dorsal and palmar views of the assistive glove 34 showing segmented soft actuators 12, attachment pieces with Velcro adhesives and straps, fabric pockets for mounting actuators and finger tips, and tubing.
Figure 61B:
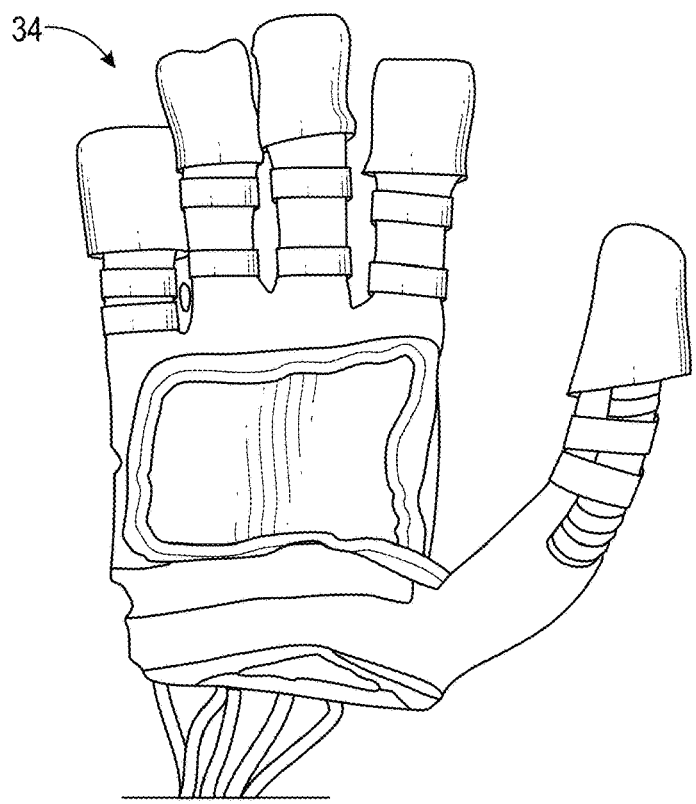

The design of the glove 34 shown in FIGS. 61*a* and 61*b* follows an open palm configuration to ensure quick, easy and safe fitting to the human hand. The main component of the glove 34, the wrist attachment piece, is made of soft material (e.g., flexible rubber foam) in a parallelogram shape. The glove 34 is placed on the dorsal side of the hand, and it serves as the anchoring and adjusting piece for the soft actuators using hook-and-loop attachment fabric (e.g., VELCRO fabric). The glove 34 can also be secured with a strap around the wrist to allow maximum conformability, ease of mounting/dismounting of the overall glove 34 and to realize an open palm device. On top of the wrist attachment, an elastic fabric (e.g., neoprene) is mounted and is used to create flexible finger and actuator attachments. The elastic fabric is cut in a shape that follows the outline of the fingers. This fabric outline is then further cut in two separate pieces—one for the thumb and another for the remaining four fingers. The fabric outlines of the fingers can have VELCRO attachments at the palm side (top and bottom side) to allow connection with the VELCRO attachments located at the wrist attachment piece (bottom side). At the distal ends of each fabric outline, two small pockets are also fabricated that (i) can hug (surround) the human fingertips from one side and (ii) can surround the distal part of the soft actuators 12 from the other side. Thus, five soft segmented actuators 12 can be mounted on the glove 34 device using (a) from their proximal side, the Velcro attachment located on the top side of the fabric outline and (b) from the distal side, the top fabric pocket.

Additionally, elastic bands are placed along the length of the actuator 12 to further secure them with the fabric outline piece. The fluid lines (tubing) 62 are located at the proximal end of each of the soft actuators. In addition, the maximum profile of the glove 34 does not exceed 1.5 cm; and its total weight, including the actuators 12, is around 240 grams (without the actuation fluid). The actuators 12 mimic the curving function of fingers utilizing the bending and extending ability of the segmented actuator design. A distribution of force, generated by the pressurized actuators 12, over the entire length of the fingers, minimizes concentrated pressure points and hence discomfort.

Figure 62A:
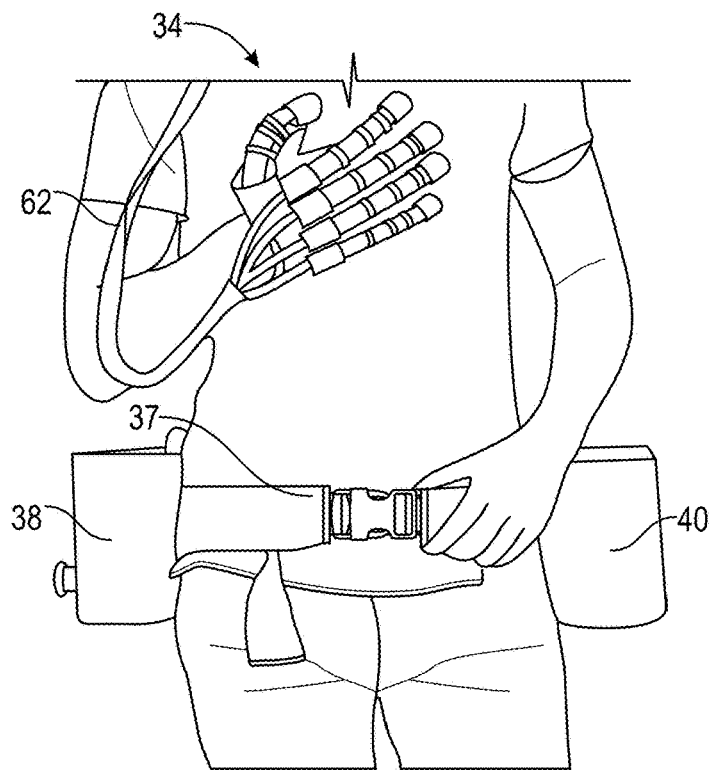
FIGS. 62a and 62b are drawings of the assistive glove 34 being worn by a user who is also wearing the portable power supply 38, pump 42, and other components to actuate the glove 34.
Figure 62B:
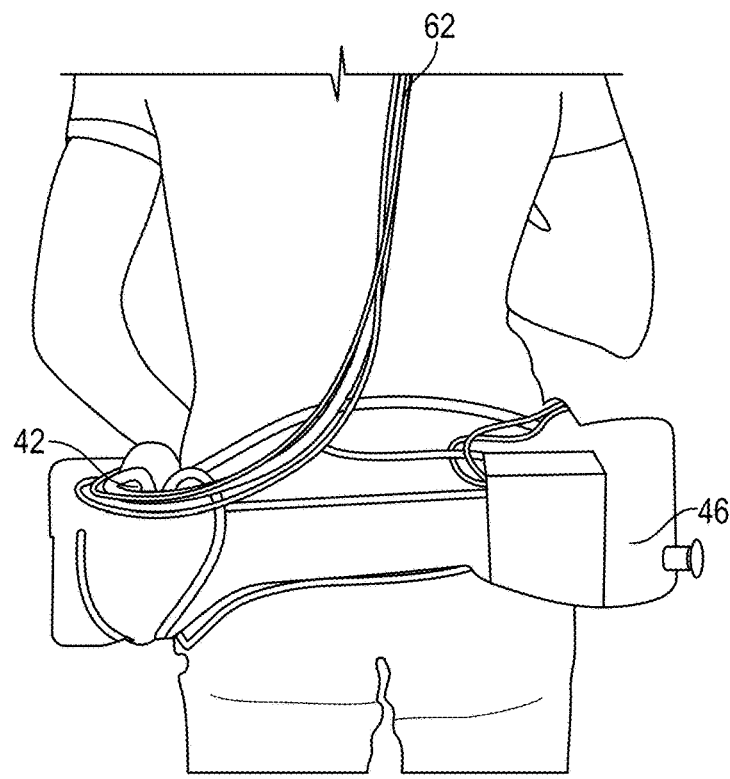
Figure 63:
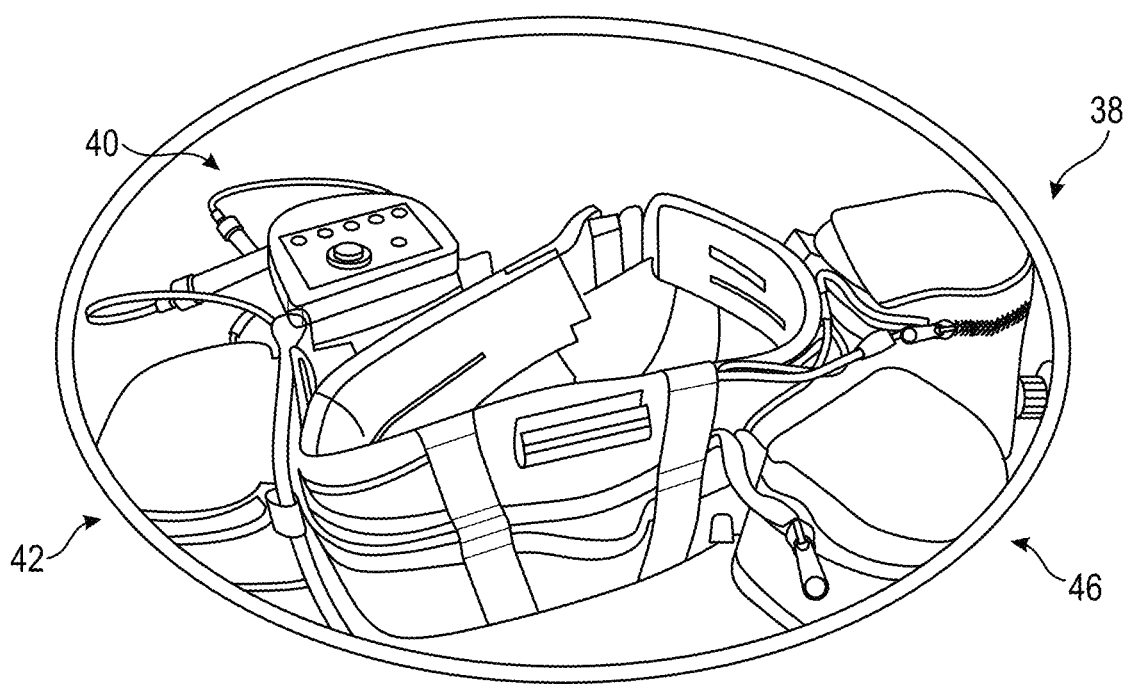
FIG. 63 is a detailed close-up drawing of the portable power supply 38 and other components carried on the user's belt.
Figure 64A:
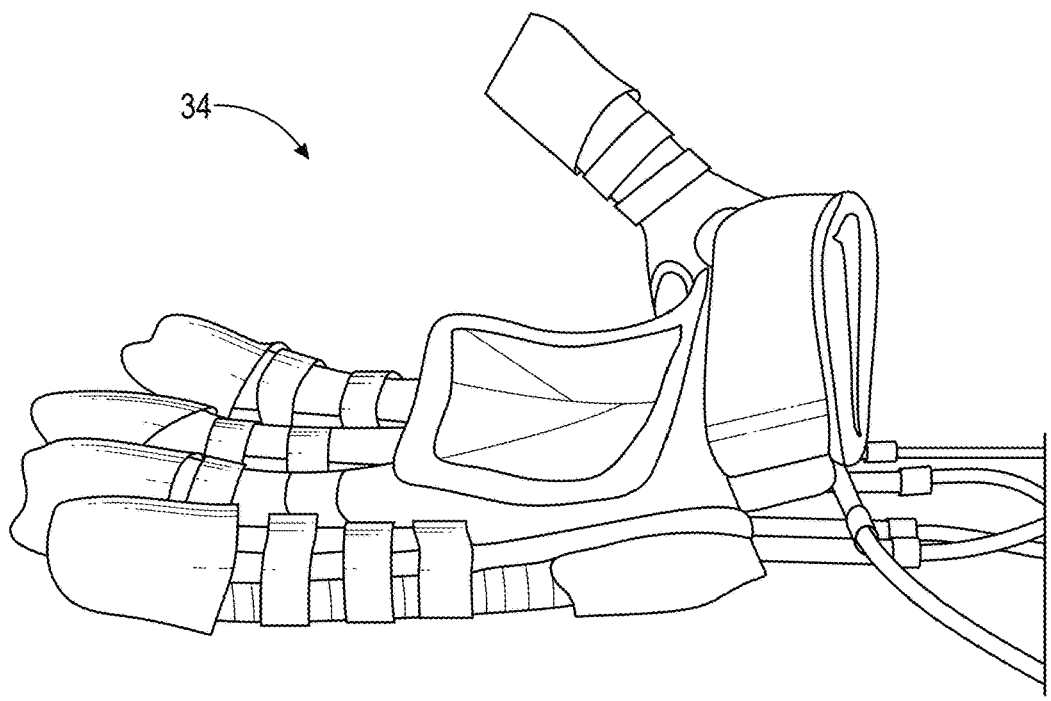
FIGS. 64a-d present a sequence of drawings of the assistive glove 34 closing as fluid pressure is increased.
Figure 64B:
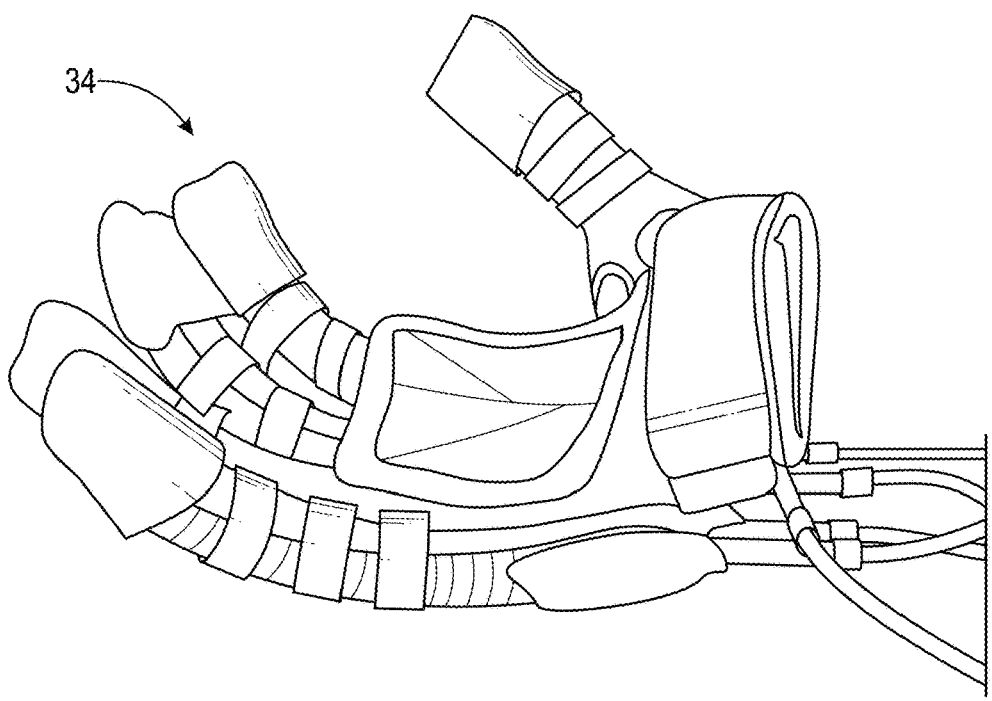
Figure 64C:
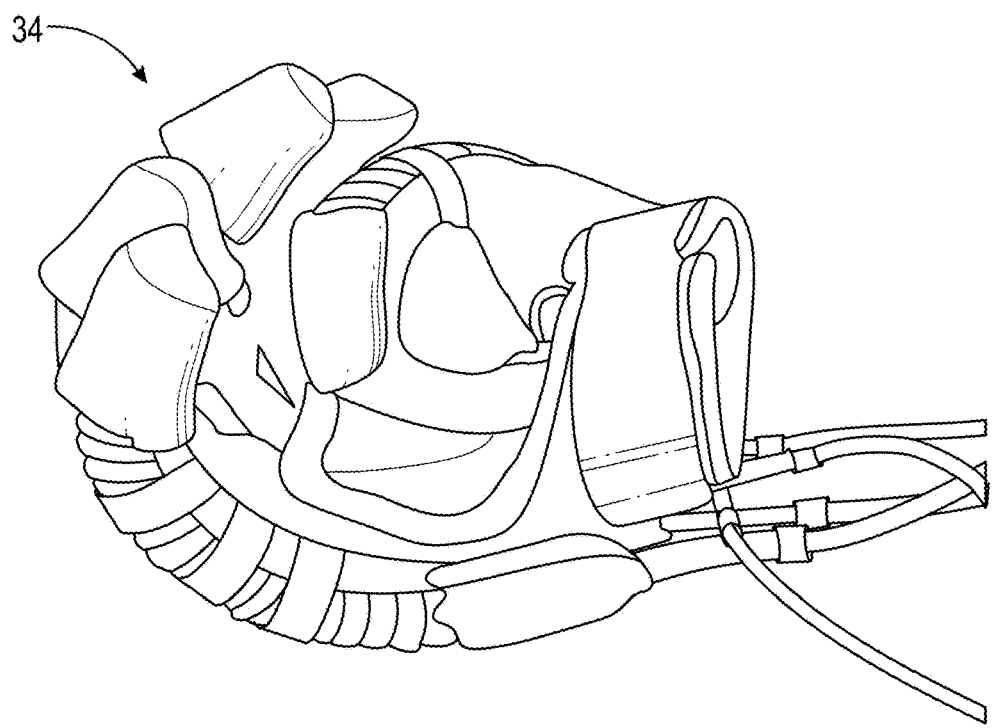
Figure 64D:
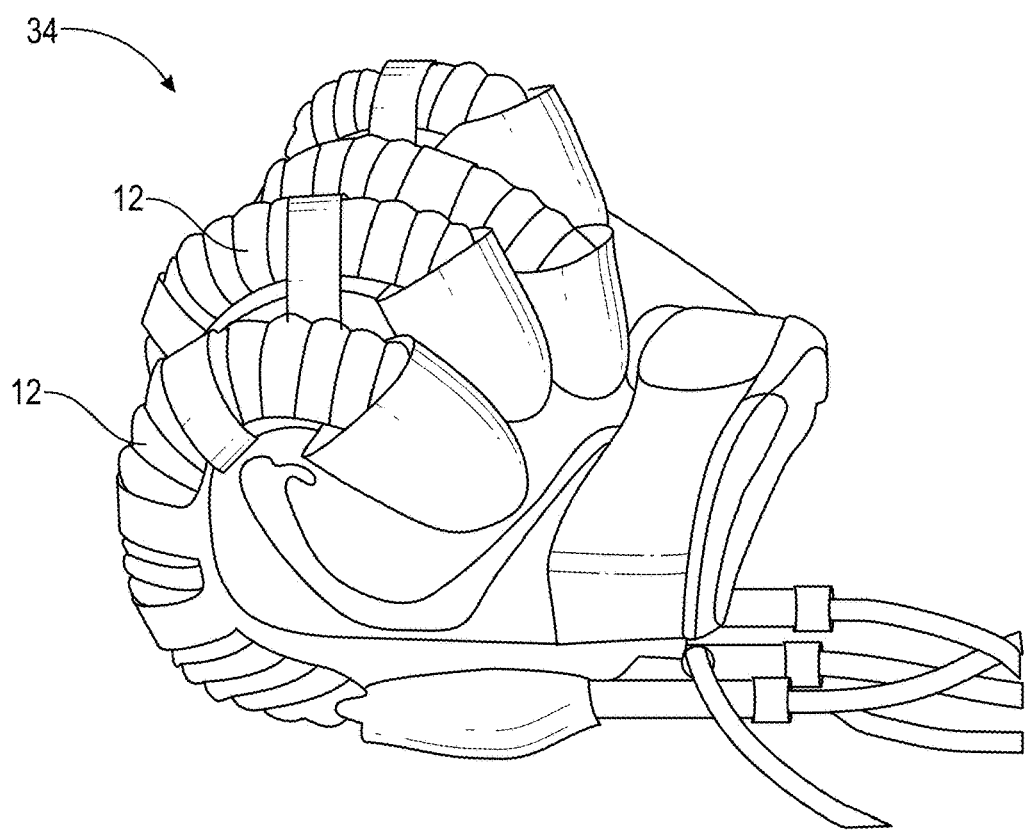
Figure 65A:
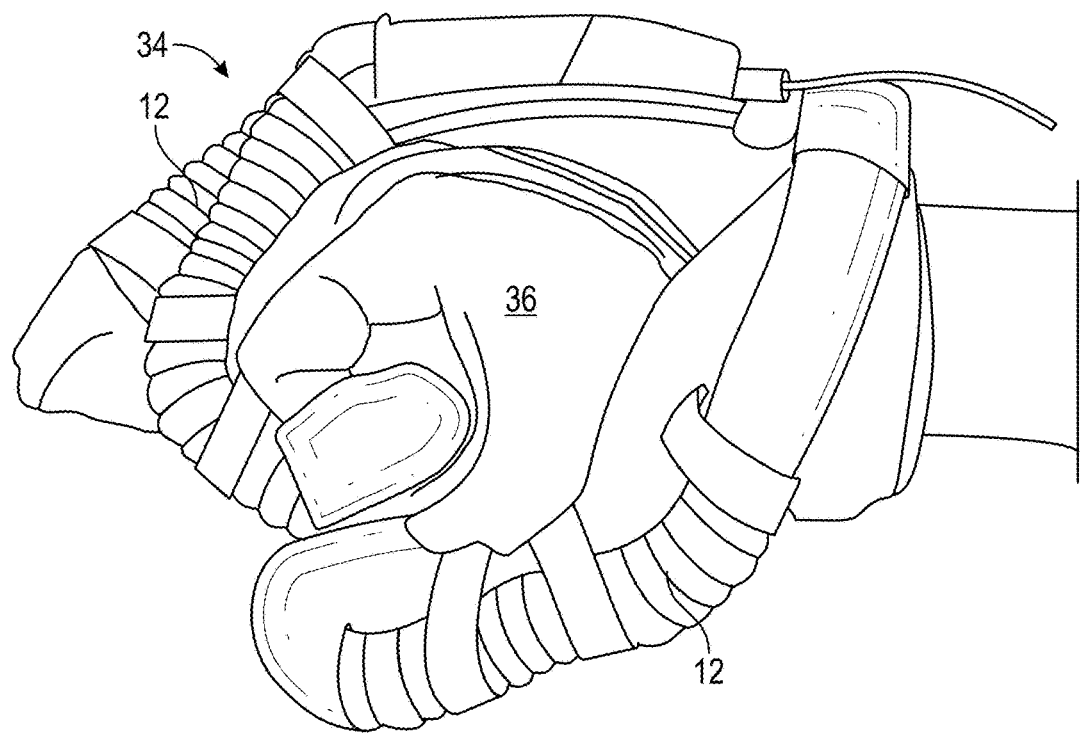
FIGS. 65a-d present the gross and precise motions that can be achieved with the assist glove 34 when worn on the hand of a user 36.
Figure 65B:
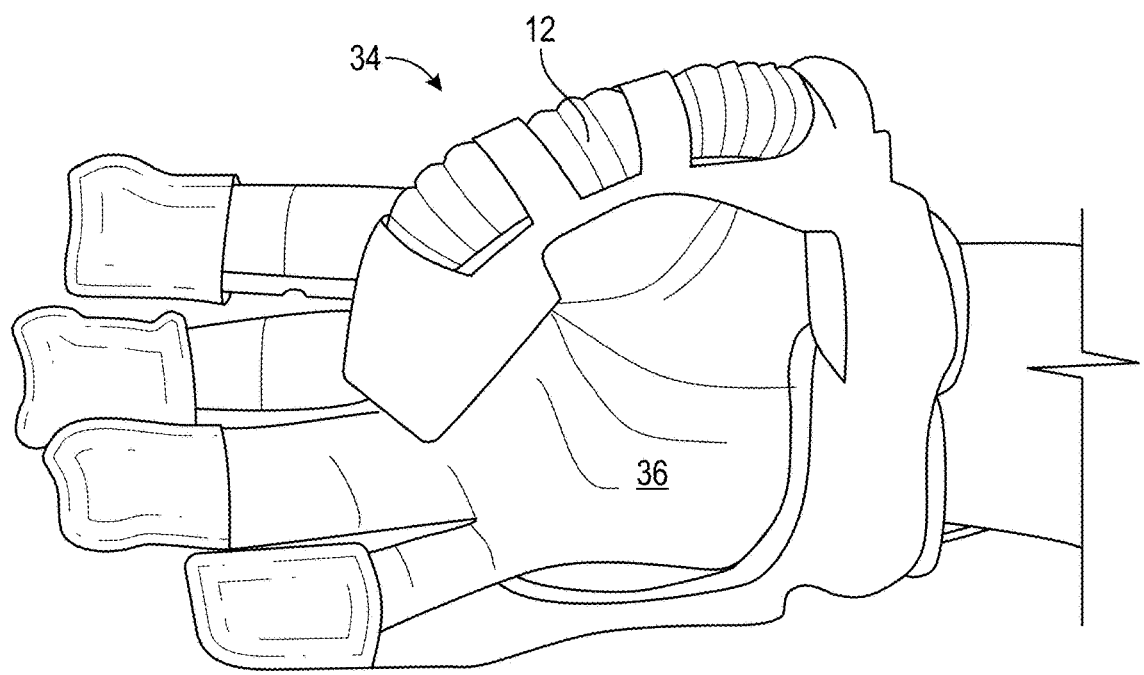
Figure 65C:
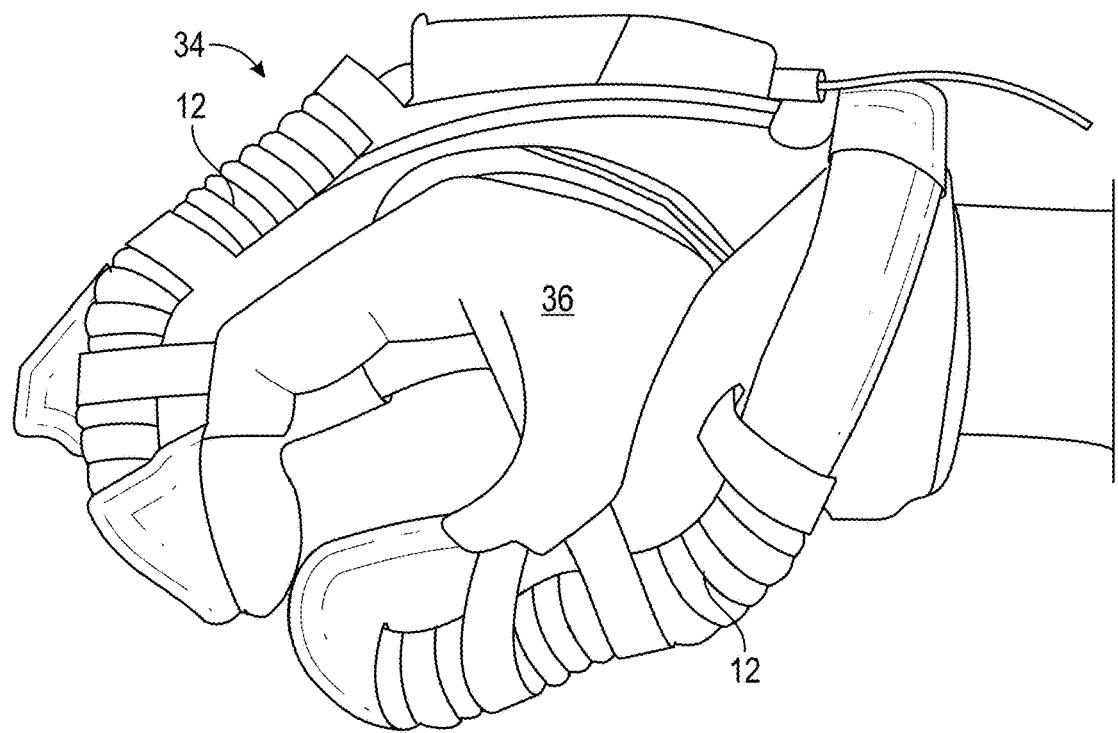
Figure 65D:
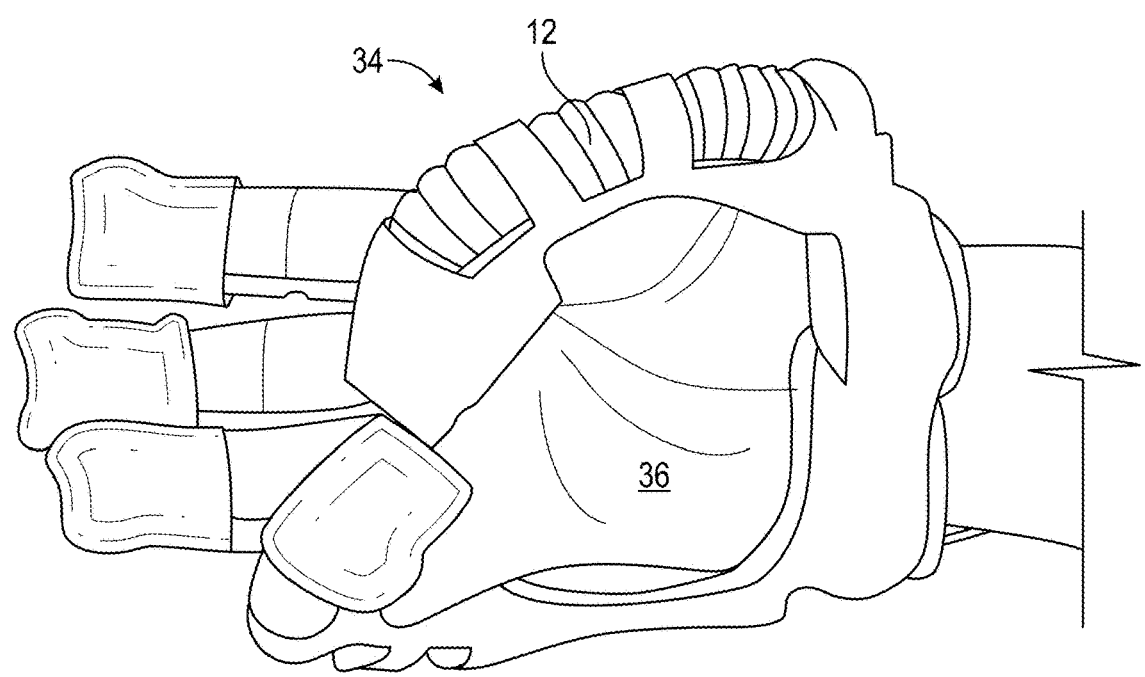

The actuators 12 are hydraulically actuated with the aid of a waist belt pack that incorporates all of the components (e.g., hydraulic pump and reservoir 42, valves and tubing 40, microcontroller 46, batteries and power regulation unit 44, etc.) that the system utilizes while operating untethered for around 4 hours (the portable assistive glove 34 example is shown in FIGS. 62a and 62b, with details of the waist belt pack in FIG. 63). The actuation of the current prototype can take place through the use of manual switches located on the belt or via pre-programmed sequences delivered by the integrated microcontroller. In other embodiments, sensing schemes can be implemented that can operate the device by sensing the intention of the wearer 36 to flex/extend the fingers.

In FIGS. 64a-d, the assistive glove 34 is pressurized to achieve free-space bending and gross and precise motions. The glove 34 has the ability to flex the human fingers entirely creating a closed first (as shown in FIGS. 65a-d). Higher pressurization of the actuators 12 can realize stronger closure of the fist. The actuator 12 coupled with each finger can be operated independently of the others; and, due to the complex motion (bend-twist-extend) that the thumb actuator can achieve precise finger motions (as shown in FIGS. 65a-d). The particular embodiment supports hand closing, though the actuators 12 can be designed to offer other modes of assistance. For example, with the multi-segment, multi-chamber actuator in FIGS. 20a and 20b, the stiffening elements can be used to help straighten fingers while the bending elements can support hand closing. Alternatively, the actuator design presented in FIG. 21 can support hand closing and opening and can hold the hand in a stiffened open position by activating both chambers.

As is further described, below, sensing schemes can be implemented (i) to enable intuitive control by the user and can make the glove operational without the need of manual user input (e.g., switches) or (ii) to have rehabilitation or physical therapy schemes programmed by a clinician. By adding sensing capabilities to the device, patient compliance can be monitored and recovery rates measured that can potentially be linked with the clinician. This capability can lead to a teletherapy platform that can revolutionize physical rehabilitation. The glove system can adopt a hierarchical control framework that permits assistance provided by the actuators to be adapted longitudinally by the therapist, with embedded machine learning methods for task-specific activities. The embedded data collection and data fusion systems can enable monitoring of therapy and accurate quantification of performance. Additionally, by making use of broadband internet, the data collected can be uploaded during the day from the system, for analysis and visualization by a therapist.

The glove 34 can be worn continuously to provide assistance with activities of daily living (ADL) in the home, but can also be used for specific rehabilitation activities. This permits the user to perform essential self-care tasks in a timely manner, while making available tunable behaviors that are controlled by the therapist for providing more-challenging tasks. Long-term use of the system can generate copious quantities of data, including environmental interactions measured by the sensors in the device. This large data set can provide the opportunity to therapists to remotely and efficiently characterize user capabilities and deficiencies with improved accuracy and resolution compared to current clinical practice.

Figure 66:
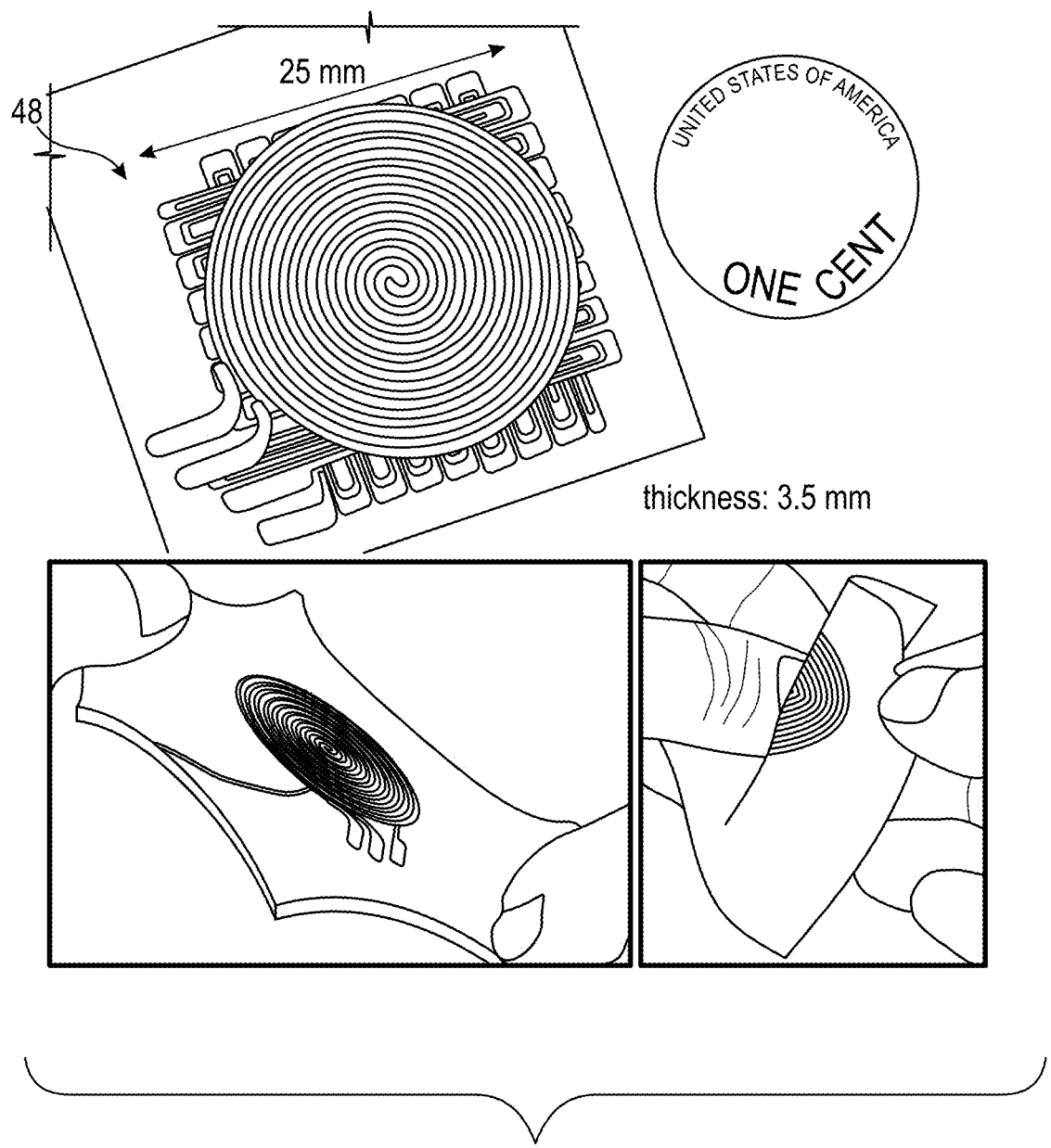
FIG. 66 presents a previous approach for hyper-elastic strain and pressure sensors 48.

One potential sensor solution is a hyper-elastic strain and pressure sensor 48 (as shown in FIG. 66), which was developed by Y-L. Park (U.S. Pat. No. 8,316,719). These sensors are as thin as a film, very soft and flexible since they are made of silicone materials. Inside these sensors, patterns of embedded micro-channels are fabricated. Their sensing technology relies on the change of resistivity of a liquid metal [e.g., eutectic gallium-indium (eGaIn)], which is injected in the embedded channels.

Figure 67:
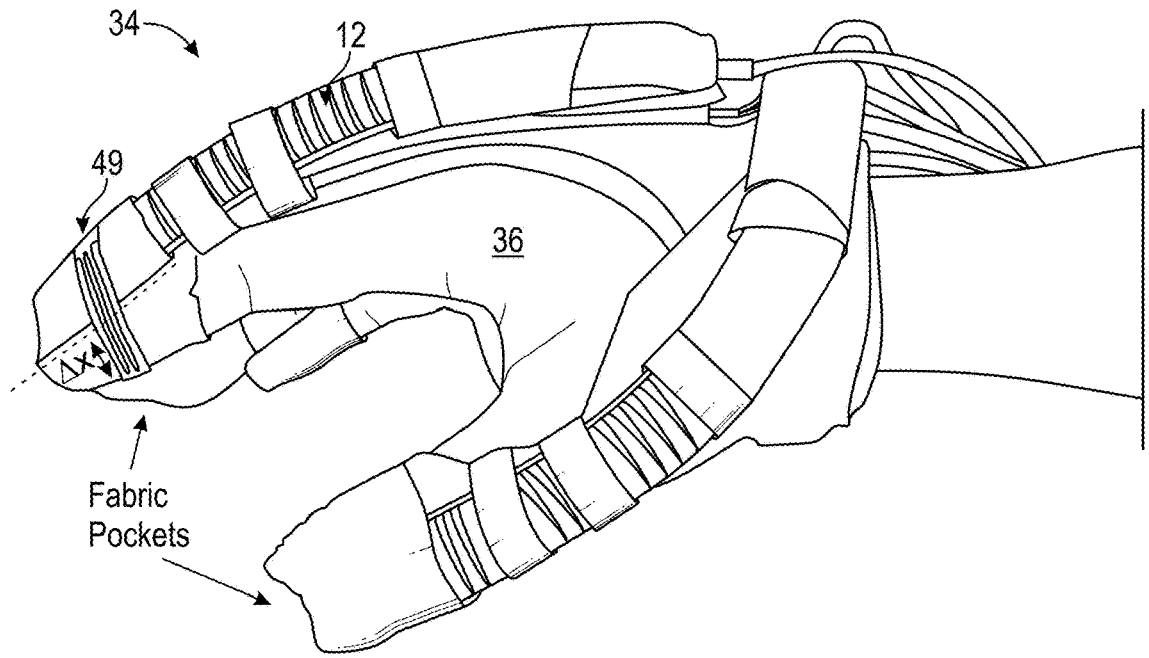
FIG. 67 presents a prototype assistive glove 34 with a hyper-elastic strain sensor band 49 around the fingertip and the actuator distal end that is used to sense the intention of the wearer to control hand closing and opening.

One such hyper-elastic strain sensor 48 can be placed around the fingertip and the actuator distal end in a form of a thin and small silicone band (as shown in FIG. 67). When the partially impaired person wants to flex a finger, the intent (e.g., the small force they produce) can be sensed by the strain sensor 48 as the distance between the actuator 12 and the finger will increase (e.g., the actuator 12 is at a non-active state, but the finger moves slightly in relation to it). Hence, the intention of the user 36 is captured, and a microcontroller interprets that strain signal and amplifies that motion by activating the pump to pressurize the actuator 12.

A sensor 48 can also be placed around or between the fingertip and the actuator 12 to act as a signal indicator when an object is interacting with the finger. When the actuator 12 is being pressurized and an object is sensed by the contact pressure generated in the sensor 48, a control signal can be generated to control the level of applied assistance. When the patient signals intent to release (e.g., by trying to open his/her hand) the sensor 48 sends a signal to the microcontroller 46; and the microcontroller 46, in turn, releases the pressure from the actuator 12 allowing the finger to return to an open state.

Another strain sensor 48 in the form of a thin strip can also be placed on top of at least one of the fingers, which are inserted into fabric pockets in the glove 34, to sense the changing bending angle of the joints (knuckles). Similar sensors can be attached to the functioning hand, to all fingers or to a single digit (e.g., a small finger), or even to the wrist to command through gestures or to replicate motion of the actuator 12 to that of the impaired body part using the assistive device. Furthermore, joint-level control can be achieved based on sensing of the patient's intended motions by surface electromyography (sEMG) signal detection, a non-invasive method of sensing electrical muscle activity. In this scenario, an embedded controller is in charge, reading the sEMG and other joint angle and force/contact data. The signals can be obtained from the muscles in the forearm that actuate the wrist, fingers, and thumb. However, the signal quality is user-dependent and related to injury or pathology.

Minute contact pressure readings can be detected using a completely different sensing method that is realized by small barometer sensors. In this sensing scheme of the glove, two small tactile pressure sensors (e.g., from TakkTile LLC, Cambridge, Massachusetts) are mounted in a thin but rigid frame (e.g., a ring-like frame). This frame is placed inside the fingertip fabric pocket of the glove 34 to allow the two sensors to sit always parallel, above and below the finger. The frame provides enough room for the fingertip to freely move inside it. Thus, small fingertip movements exert some pressure to either the top or lower sensor; and these signals are used to flex or extend the fingers respectively by pressurizing/depressurizing the soft-segmented actuators 12.

In additional embodiments, the actuator 12 can be operated by voice command by providing a microphone or other voice input device and connecting it with controller. The controller can be programmed to respond to communications from the voice input device generated by its detection of voice commands to send an instruction to the pump 42 to deliver pressurized fluid into or out of the actuator 12 to generate the displacements that the actuator 12 is engineered to produce.

Another sensing scheme involves using electrical brain stimuli to interpret the intentions of the wearer to use the hand and fingers. In this scheme, a cap with electrodes can be worn to interact with the surface of the human skull and to capture signals related hand and finger motion. The captured signals can be then interpreted by a controller that can effectively send commands to the assistive device to generate movement in accord with the signals.

A fusion of signals from all of the sensors can be used in various control schemes to allow the glove 34 to interpret correctly the intention of the wearer 36 and to interact more accurately with the unknown environment. However, calibrations are utilized to relate sensor readings to actual joint configurations. In soft systems, this relationship varies with a number of factors, some that are identifiable each time a user 36 puts on the system (e.g., positioning the device on the user's hand) and some that change during use (e.g., joint coupling and actuator and task force distortion of the compliant structure). Preliminary work suggests that close envelopment of the fingers and forearm by the wearable device greatly constrains the relationship to the user's joints. Therefore, by parameterizing the geometric relationship between the hand and wearable device, calibrations can be achieved. Specific parameter values can then be identified using data acquired during an initial calibration routine performed by the user 36.

In some applications, the actuators 12 can be disposable (e.g., discarded after a specified period of use, such as after one month of use) and replaced, while the pump 42 can be retained for longer-term reuse.

Additional images of simulations showing the extension, expansion, twisting and contraction of actuators with pressurization are described, below, and shown in FIGS. 68-72. Where a fiber is used as the actuator reinforcement, a pitch, $\alpha$, of $0°$ (representing to circumferential fibers) constrains motion to the axial/longitudinal direction along the length of the fiber. As a is increased from $0°$, radial expansion increases and axial extension decreases until finally, at $\alpha=90°$ (axial fibers), we have maximum radial expansion and no axial extension. Interestingly, we see that for fiber angles in the $50°$ to $90°$ range, the axial stretch is non-monotonic, as the length of the actuator first decreases and then increases as pressure increases. Finally, by plotting twist per unit length as a function of pressure, we note that at $0°$ and $90°$, the fibers are arranged symmetrically, so there is no twist about the axis. We also see the unintuitive result that twist peaks around $\alpha=30°$.

Figure 68:
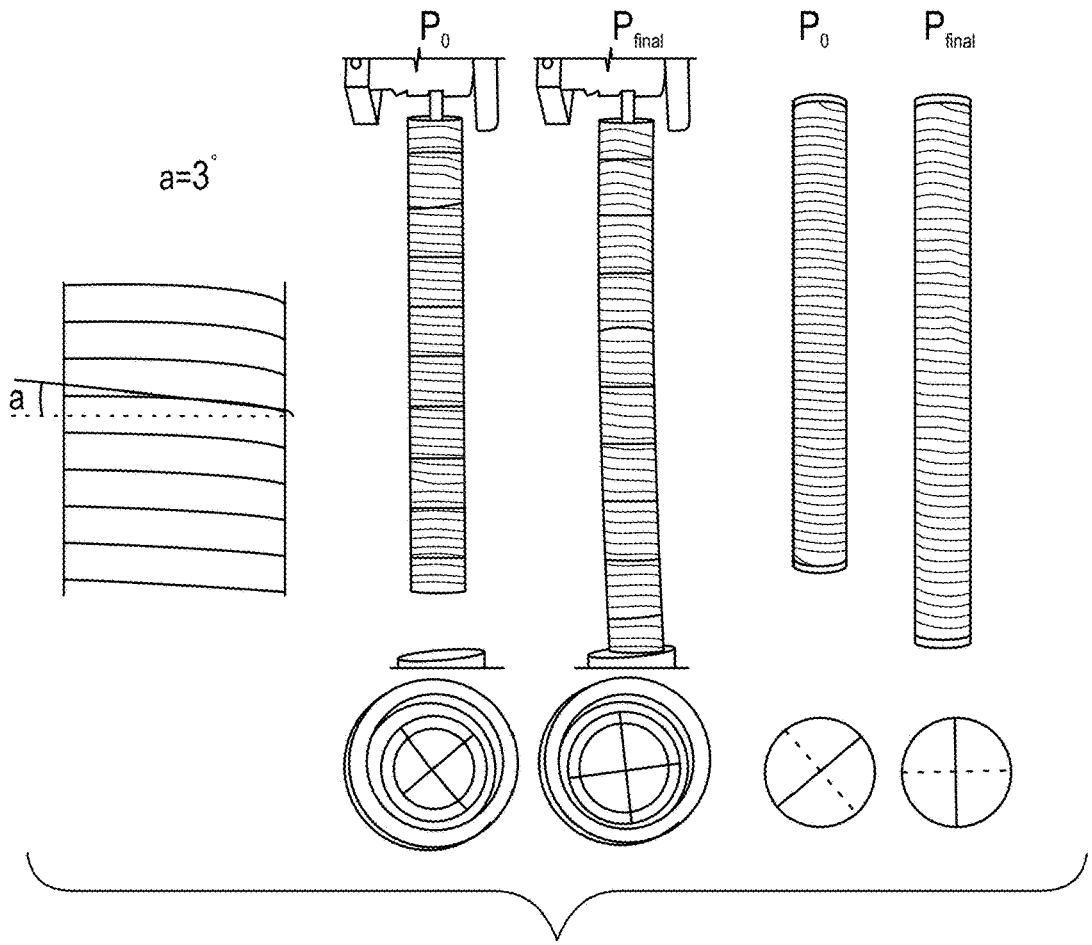
FIG. 68 shows the fiber configuration and the longitudinal extension and twisting of an actuator with fiber reinforcements wound with a pitch angle, a, of 3°.

An actuator with fiber reinforcements wound with a pitch angle, $\alpha$, of $3°$, is shown in FIG. 68. As shown at right, this actuator twists and extends (longitudinally) when actuated with a pressure increase from $P_0$ to $P_{final}$.

Figure 69:
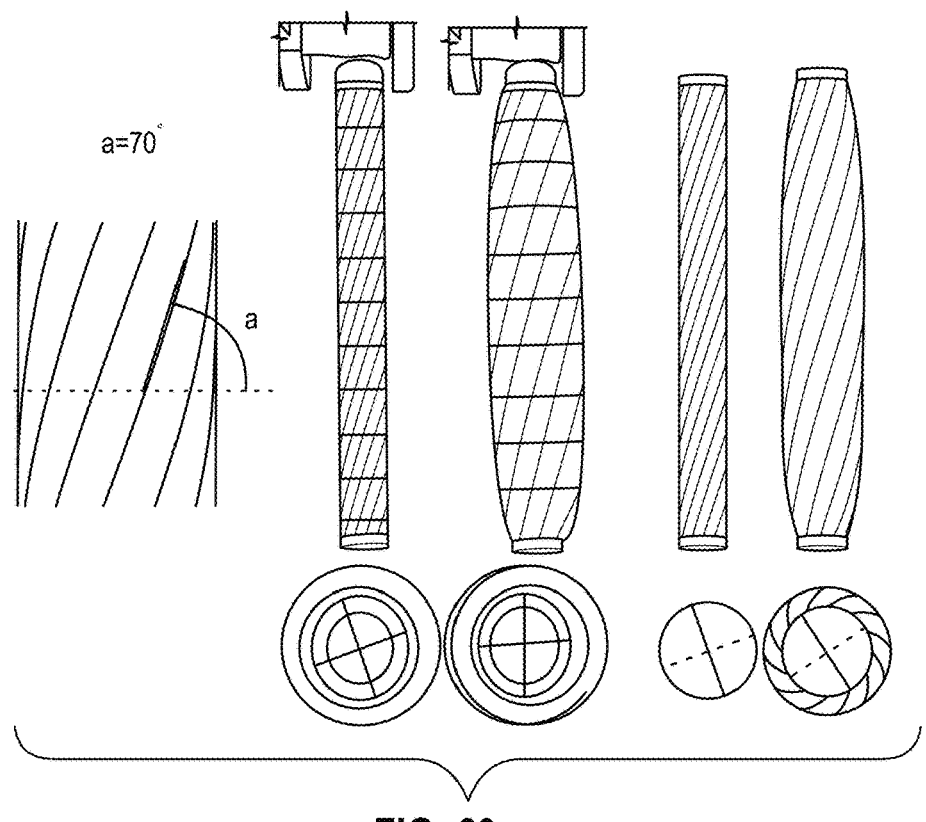
FIG. 69 shows the fiber configuration and the radial expansion and twisting of an actuator with fiber reinforcements wound with a pitch angle, a, of 70°.
Figure 70:
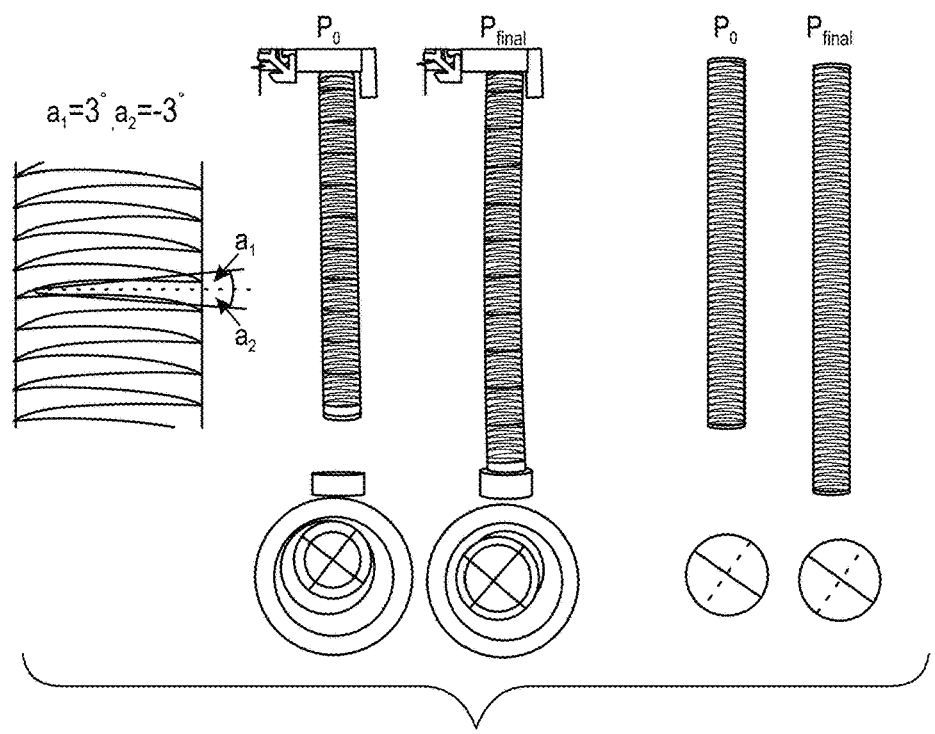
FIG. 70 shows the configuration of a pair of symmetrically wound fibers in an extending yet non-twisting actuator, where one fiber is wound with a pitch of 3° and the other is wound with an opposite pitch of −3°.

In contrast, an actuator with a much greater pitch (i.e., $\alpha=70°$ is shown in FIG. 69. As shown at right, this actuator twists and expands (radially) when actuated with a pressure increase from $P_0$ to $P_{final}$.

Where the actuator includes a pair of symmetrically wound fibers, where one family of fibers is wound with a pitch of $3°$ and the other family of fibers is wound with an opposite pitch of $-3°$, as shown in FIG. 70. In this embodiment, the opposite pitches cancel any twisting of the actuator, while allowing for its longitudinal extension and slight radial expansion (where extension and expansion were very similar to what was found with only a family of fibers) when actuated with a pressure increase from $P_0$ to $P_{final}$.

Figure 71:
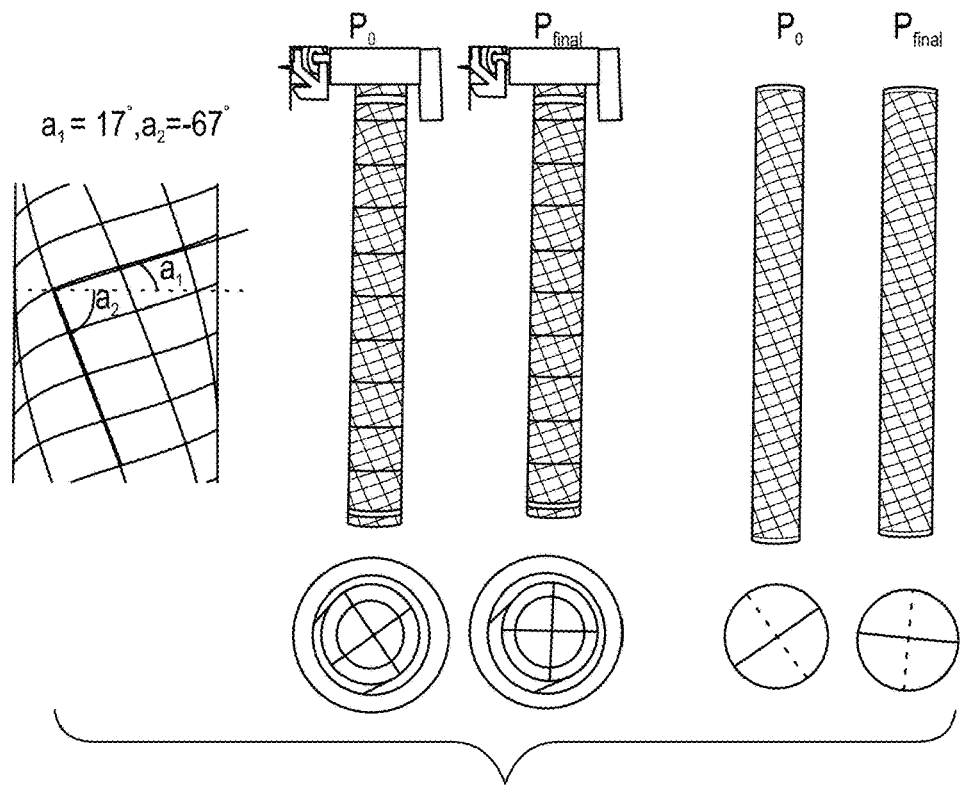
FIG. 71 shows the fiber configuration in an actuator with a pair of asymmetrically wound fibers (wound respectively at $\alpha_1=17°$ and at $\alpha_2=70°$); this actuator slightly contracts (and twists) when actuated.
Figure 72:
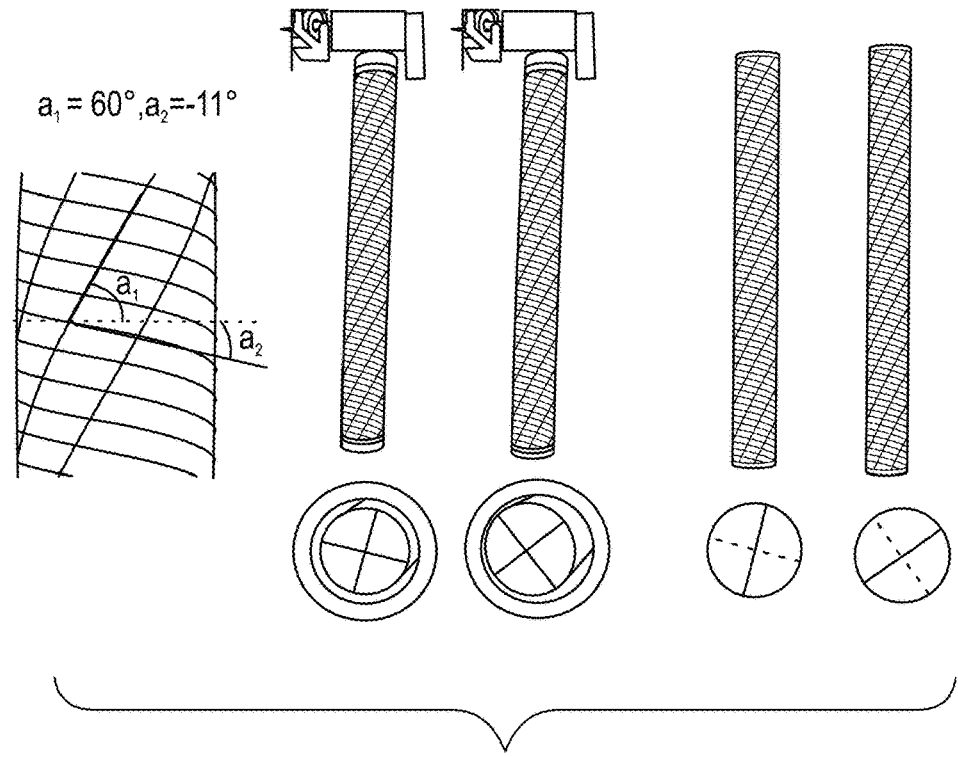
FIG. 72 shows the fiber configuration in an actuator with a pair of asymmetrically wound fibers (wound respectively at $\alpha_1=60°$ and at $\alpha_2=11°$); this actuator slightly extends (and twists) when actuated.

Finally, two embodiments of actuators with pairs of asymmetrically wound fibers are shown in FIGS. 71 and 72. The fibers in the actuator of FIG. 71 are wound respectively at $\alpha_1=17°$ and at $\alpha_2=70°$. As shown in the images at the right of FIG. 71, this actuator slightly contracts (and twists) when actuated with a pressure increase from $P_0$ to $P_{final}$. The fibers in the actuator of FIG. 72, meanwhile, are wound respectively at $\alpha_1=60°$ and at $\alpha_2=11°$. As shown in the images at the right of FIG. 72, this actuator slightly extends (and twists) when actuated with a pressure increase from $P_0$ to $P_{final}$. The actuators of FIGS. 71 and 71 have almost the same curve for twist, neither experienced much expansion in radius.

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties or other values are specified herein for embodiments of the invention, those parameters or values can be adjusted up or down by $1/100^{th}$, $1/50^{th}$, $1/20^{th}$, $1/10^{th}$, $1/5^{th}$, $1/3^{rd}$, $1/2$, $2/3^{rd}$, $3/4^{th}$, $4/5^{th}$, $9/10^{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety; and appropriate components, steps, and characterizations from these references may or may not be included in embodiments of this invention. Still further, the components and steps identified in the Background section are integral to this disclosure and can be used in conjunction with or substituted for components and steps described elsewhere in the disclosure within the scope of the invention. In method claims, where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. A device configured to be worn by a human including a sensor-actuated soft actuator, the device comprising:
    at least one soft actuator body defining a chamber, wherein the soft actuator body is incorporated into the device;
    a fluid connector positioned and configured to provide a path for fluid flow into and out of the chamber;
    a control system connected with the soft actuator body, wherein the control system comprises a pneumatic or hydraulic pump, valves, and a microcontroller and is configured to control fluid flow through the fluid connector into and out of the chamber to produce at least one actuation motion selected from bending, extending, stiffening, expansion, contraction, twisting, and combinations thereof in the soft actuator body; and
    at least one sensor, including a strain sensor, incorporated into the device and in communication with the microcontroller, wherein the microcontroller is configured to control the fluid flow based on communications from the at least one sensor, including the strain sensor, and to thereby control actuation of the soft actuator body.

2. A device configured to be worn by a human including a sensor-actuated soft actuator, the device comprising:
- at least one soft actuator body defining a chamber, wherein the soft actuator body is incorporated into the device;
- a fluid connector positioned and configured to provide a path for fluid flow into and out of the chamber;
- a control system connected with the soft actuator body, wherein the control system comprises a pneumatic or hydraulic pump, valves, and a microcontroller and is configured to control fluid flow through the fluid connector into and out of the chamber to produce at least one actuation motion selected from bending, extending, stiffening, expansion, contraction, twisting, and combinations thereof in the soft actuator body; and
- at least one sensor incorporated into the device and in communication with the microcontroller, wherein the microcontroller is configured to control the fluid flow based on communications from the sensor and to thereby control actuation of the soft actuator body,
- wherein the human suffers from a disability as a result of an injury or medical condition, and wherein the actuation motion, when performed in a rehabilitation exercise, treats the disability based on the at least one sensor sensing the action of the human, without claiming the human, and
- wherein the device is in communication with a teletherapy platform that provides for the rehabilitation exercise to be guided via teletherapy.

3. The device of claim 2, wherein the device is a glove.

4. The device of claim 2, wherein the sensor is configured to detect a force produced by the human wearing the garment and to communicate the detection of the force produced by the human to the control system, wherein the control system is programmed to generate an actuation in the soft actuator body that amplifies the force produced by the human.

5. The device of claim 4, wherein the sensor is configured to detect a release of the force produced by the human and to communicate the detection of the release of the force produced by the human to the control system, wherein the control system is programmed to release the actuation in the soft actuator body to remove the amplified force.

6. The device of claim 2, wherein the sensor is configured to detect a force produced as result of interaction between the garment and an external object and to communicate the detection to the control system to alter the degree of actuation in response to the interaction.

7. The device of claim 2, wherein the sensor is positioned in the device at a location where the sensor can detect bending of a joint of the human wearing the device.

8. The device of claim 2, wherein the sensor is configured for surface electromyography signal detection to sense the human's muscle activity.

9. The device of claim 2, wherein the sensor is a tactile pressure sensor.

10. The device of claim 2, wherein the sensor includes electrodes configured to measure electrical stimuli in the brain of the human.

11. The device of claim 2, wherein the at least one soft actuator body defines a plurality of chambers, wherein the chambers are configured such that the flow of fluid into different chambers produces different types of actuations.

12. The device of claim 11, wherein the chambers are opposing and are configured to produce bending or extending depending on at least one of (a) which of the chambers receives the flow of fluid or (b) whether one or a plurality of the chambers receive the flow of fluid.

13. A method for sensor-driven actuation of a soft actuator in a device of claim 2, the method comprising:
- donning the device of claim 2 on a human;
- sensing an action of the human or contact with an object using the sensor;
- pumping fluid into or out of the chamber in response to the sensed action or contact to produce an actuation motion in the soft actuator body selected from at least one of the following types: bending, extending, stiffening, expansion, contraction, twisting and combinations thereof; and
- using the actuation motion to cause or mechanically assist displacement of a body part of the human.

14. The method of claim 13, wherein the action is selected from motion, application of pressure, transmission of an electromyography signal, generation of a voice command, and transmission of electrical brain signals.

15. The method of claim 13, wherein the device is donned on a hand of the human, the method further comprising aligning the soft actuator body with a digit of the hand.

16. The method of claim 15, wherein the device is a glove.

17. The method of claim 16, wherein the actuator is attached to a dorsal side of the hand, wherein the glove is secured around a wrist of the human, and wherein the glove includes pockets that surround fingertips of the hand on a ventral side of the hand and the actuator on the dorsal side of the hand.

18. The device of claim 2, wherein the device is a glove worn on a human hand, wherein the soft actuator body is positioned to align with a digit of the human hand, and wherein the soft actuator body and the control system are configured for the actuation motion to cause or mechanically assist the digit to bend or straighten at a joint of the digit, without claiming the human hand, itself.

19. The device of claim 2, wherein the glove includes a plurality of the soft actuators, and wherein the soft actuator bodies and the control system a configured for the actuation motions in a plurality of the soft actuators to assist the human to open or close a plurality of digits of the human's hand, without claiming the human hand, itself.

20. The device of claim 2, wherein the device is configured to communicate the action or contact sensed by the sensor to a remote therapist for monitoring and analysis.

21. The device of claim 2, wherein the microcontroller is pre-programmed to provide automated control for performing the actuation motion to treat a disability in a human suffering from the disability as a result of an injury or medical condition, without claiming the human.

* * * * *